US008389764B2

(12) United States Patent
Kallus et al.

(10) Patent No.: US 8,389,764 B2
(45) Date of Patent: Mar. 5, 2013

(54) UREA AND SULFAMIDE DERIVATIVES AS INHIBITORS OF TAFIA

(75) Inventors: Christopher Kallus, Frankfurt am Main (DE); Mark Broenstrup, Frankfurt am Main (DE); Werngard Czechtizky, Frankfurt am Main (DE); Andreas Evers, Frankfurt am Main (DE); Markus Follmann, Wülfrath (DE); Nis Halland, Frankfurt am Main (DE); Herman Schreuder, Franfurt am Main (DE)

(73) Assignee: Sanofi, Paris (FR)

( * ) Notice: Subject to any disclaimer, the term of this patent is extended or adjusted under 35 U.S.C. 154(b) by 477 days.

(21) Appl. No.: 12/480,348

(22) Filed: Jun. 8, 2009

(65) Prior Publication Data

US 2010/0035930 A1 Feb. 11, 2010

Related U.S. Application Data

(63) Continuation of application No. PCT/EP2007/010101, filed on Nov. 22, 2007.

(30) Foreign Application Priority Data

Dec. 6, 2006 (DE) .......................... 10 2006 057 413

(51) Int. Cl.
*C07C 275/00* (2006.01)
*C07C 273/00* (2006.01)
*C07C 331/00* (2006.01)
*C07C 381/00* (2006.01)

(52) U.S. Cl. ............. 564/58; 564/79; 514/588; 514/600
(58) Field of Classification Search .................. 514/588, 514/600; 564/32, 79, 58
See application file for complete search history.

(56) References Cited

U.S. PATENT DOCUMENTS 6,214,851 B1 4/2001 Duncia et al.

FOREIGN PATENT DOCUMENTS

| EP | 0611776 | 8/1994 |
|---|---|---|
| EP | 0641779 | 3/1995 |
| WO | WO9911606 A | 3/1999 |
| WO | WO0044335 | 8/2000 |

OTHER PUBLICATIONS

Schlogl et. al., CAS STN Abstract, 1953.*
Majer et. al., Journal of Organic Chemistry, 1994, American Chemical Society, vol. 59, pp. 1937-1938.*
Slater, Martin J. et al., "Pyrrolidine-5, 5-translactams.4. Incorporation of a P3/P4 Urea Leads to Potent Intracellular Inhibitors of Hepatitis C Virus NS3/4 Protease" Organic Letters, vol. 5, No. 24, 2003, pp. 4627-4630, XP002515766.
Database CA [Online] Chemical Abstracts Service, Columbus Ohio, US; BECU, F. et al: "Synthetic approaches for thymopentin (TP-5) using the in situ silylation strategy with trimethylsilyl cyanide" XP002510046, found in STN Database accession No. 1991:144007.
Database CA [Online] Chemical Abstracts Service, Columbus Ohio, US; Tomatis, R. et al. "N-Terminal Leu-enkephalin rearrangements. I" XP002510047, found in STN Database accession No. 1977:536368.
Database CA [Online] Chemical Abstracts Service, Columbus Ohio, US; Savel'ev, E.P. et al., "Synthesis of tRNA unreido derivatives as substrates for the investigation of the ribosome peptidyl tranferase center" XP002510048, found in STN Database accession No. 1972:536369.
Database CA [Online] Chemical Abstracts Service, Columbus Ohio, US; Waki, Michinori, et al."Peptide antibiotics. XIII. Synthesis of retrogramicid in S" XP002510049, found in STN Database accession No. 1969:4580.
Database CA [Online] Chemical Abstracts Service, Columbus Ohio, US; Rushig, Heinrich, et al."New orally effective blood sugar reducing compounds" XP002510050, found in STN Database accession No. 1959:7010.
Database CA [Online] Chemical Abstracts Service, Columbus Ohio, US; Schlogl, K. et al. "Peptides. XI. Determination of structure peptides. 6. Lysyl peptides" CP002510051, found in STN Database accession No. 1954:60171.
Database CA [Online] Chemical Abstracts Service, Columbus Ohio, US; Broadbridge, R.J. et al., "Design and synthesis of novel Src homology-2 domain inhibitors" XP002510052, found in STN Databse accession No. 1999:578840.
Database CA [Online] Chemical Abstracts Service, Columbus Ohio, US; Shin-Watanabe T. et al., "The structure of .beta.-MAPI, a novel proteinase inhibitor" XP002510054, found in STN Database accession No. 1983:4767.
International Preliminary Report of Patentability related to PCT/EP2007/010101 dated Jul. 7, 2009.

* cited by examiner

*Primary Examiner* — Sreeni Padmanabhan
*Assistant Examiner* — Sarah Pihonak
(74) *Attorney, Agent, or Firm* — Scully, Scott, Murphy & Presser, P.C.

(57) ABSTRACT

The invention relates to compounds of the formula I (I)

$$R_1\text{-O-C(=O)-C(R_9)(R_2)-N(H)-X-N(H)-C(R_7)(R_3)-C(=O)-R_4}$$

as defined herein, which are inhibitors of activated thrombin-activatable fibrinolysis inhibitor. The compounds of the formula I are suitable for manufacturing medicaments for the prophylaxis, secondary prevention and therapy of one or more disorders which are associated with thromboses, embolisms, hypercoagulability or fibrotic changes.

7 Claims, No Drawings

UREA AND SULFAMIDE DERIVATIVES AS INHIBITORS OF TAFIA

FIELD OF THE INVENTION

The invention relates to novel compounds of the formula I which inhibit the enzyme TAFIa (activated thrombin-activatable fibrinolysis inhibitor), to process for their preparation and to the use thereof as medicaments.

BACKGROUND OF THE INVENTION

The enzyme TAFIa is produced for example through thrombin activation from the thrombin-activatable fibrinolysis inhibitor zymogen (TAFI). The enzyme TAFI is also referred to as plasma procarboxypeptidase B, procarboxypeptidase U or procarboxy-peptidase R and is a proenzyme similar to carboxypeptidase B (L. Bajzar, Arterioscler. Thromb. Vasc. Biol. 2000, pages 2511-2518).

During formation of a clot, thrombin is generated as the final product of the coagulation cascade and induces conversion of soluble plasma fibrinogen to an insoluble fibrin matrix. At the same time, thrombin activates the endogenous fibrinolysis inhibitor TAFI. Activated TAFI (TAFIa) is thus produced during thrombus formation and lysis from the zymogen TAFI through the action of thrombin; thrombomodulin in a complex with thrombin increases this effect about 1250-fold. TAFIa cleaves basic amino acids at the carboxy end of fibrin fragments. The loss of carboxy-terminal lysines as binding sites for plasminogen then leads to inhibition of fibrinolysis. Efficient inhibitors of TAFIa prevent the loss of these high-affinity lysine binding sites for plasminogen and, in this way, assist endogenous fibrinolysis by plasmin: TAFIa inhibitors have profibrinolytic effects.

In order to maintain hemostasis in the blood, mechanisms which lead to the clotting of blood and to the breaking up of clots have developed; these are in equilibrium. If a disturbed equilibrium favors coagulation, fibrin is produced in larger quantities, so that pathological processes of thrombus formation may lead to serious pathological states in humans.

Just like excessive coagulation may lead to serious pathological states caused by thrombosis, an antithrombotic treatment entails the risk of unwanted bleeding through disturbance of the formation of a necessary hemostatic plug. Inhibition of TAFIa increases endogenous fibrinolysis—without influencing coagulation and platelet aggregation—i.e. the disturbed equilibrium is shifted in favor of fibrinolysis. It is thus possible both to counter the buildup of a clinically relevant thrombus, and to increase the lysis of a pre-existing clot. On the other hand, buildup of a hemostatic plug is not impaired, so that a hemorrhagic diathesis is probably not to be expected (Bouma et al., J. Thrombosis and Haemostasis, 1, 2003, pages 1566-1574).

Inhibitors of TAFIa have previously been described in the international application WO2005/105781.

SUMMARY OF THE INVENTION

The invention relates to the use of a compound of formula I

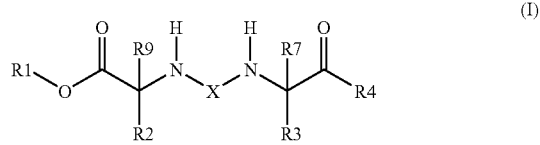

wherein
X is —C(O)— or —S(O)$_2$—,
R1 is 1) hydrogen atom,
   2) —(C$_1$-C$_6$)-alkyl,
   3) —(C$_0$-C$_4$)-alkylene-(C$_3$-C$_{12}$)-cycloalkyl or
   4) —(C$_1$-C$_6$)-alkylene-(C$_6$-C$_{14}$)-aryl,
R2 is the radical of the formula II $$-(A1)_m-A2 \qquad (II)$$

wherein
m is the integer zero or 1,
$A^1$ is 1) —(CH$_2$)$_n$— in which n is the integer zero, 1, 2 or 3,
   2) —NH—(CH$_2$)$_n$— in which n is the integer zero, 1, 2 or 3,
   3) —NH((C$_1$-C$_6$)-alkyl)-(CH$_2$)$_n$— in which n is the integer zero, 1, 2 or 3,
   4) —NH((C$_3$-C$_6$)-cycloalkyl)-(CH$_2$)$_n$— in which n is the integer zero, 1, 2 or 3,
   5) —O—(CH$_2$)$_n$— in which n is the integer zero, 1, 2 or 3 or
   6) —(CH$_2$)$_n$—SO$_x$— in which n is the integer zero, 1, 2 or 3, and x is the integer zero, 1 or 2,
A2 is 1) Het, which means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, and is unsubstituted or substituted independently of one another once, twice or three times by —(C$_1$-C$_3$)-alkyl, halogen, —NH$_2$, —CF$_3$ or —O—CF$_3$,
   2) —(C$_0$-C$_6$)-alkylene-NH$_2$,
   3) —(C$_1$-C$_6$)-alkylene-NH—C(═NH)—NH$_2$,
   4) —(C$_1$-C$_6$)-alkylene-NH—C(═NH)—(C$_1$-C$_4$)-alkyl,
   5) —(C$_0$-C$_4$)-alkylene-O—NH—C(═NH)—NH$_2$,
   6) —(C$_0$-C$_4$)-alkylene-NH—C(O)—(C$_1$-C$_6$)-alkyl,
   7) —(C$_1$-C$_6$)-alkylene-NH—C(O)—O—(C$_1$-C$_4$)-alkylene-(C6-C14)-aryl, where aryl is unsubstituted or substituted by —NH$_2$ or is substituted by —NH$_2$ and once, twice or three times by R15,
   8) —(C$_3$-C$_8$)-cycloalkyl-NH$_2$ or
   9) —(C$_0$-C$_4$)-alkylene-(C$_6$-C$_{14}$)-aryl, where aryl is unsubstituted or substituted by —NH$_2$ or is substituted by —NH$_2$ and once, twice or three times by R15,
R3 is 1) —(C$_1$-C$_6$)-alkyl,
   2) —(C$_0$-C$_4$)-alkylene-(C$_3$-C$_{12}$)-cycloalkyl,
   3) —(C$_1$-C$_6$)-alkylene-(C$_6$-C$_{14}$)-aryl, where aryl is substituted independently of one another once, twice or three times by R15,
   4) —(C$_0$-C$_8$)-alkylene-N(R5)-PG1,
   5) —(C$_1$-C$_6$)-alkylene-NH—C(O)—O—(C$_1$-C$_4$)-alkylene-(C6-C14)-aryl, where aryl is substituted independently of one another once, twice or three times by R15,
   6) —(C$_0$-C$_4$)-alkylene-(C$_6$-C$_{14}$)-aryl-(C$_0$-C$_4$)-alkylene-N(R5)-PG1, 7) —($C_0$-$C_8$)-alkylene-O-PG2,
8) —($C_0$-$C_4$)-alkylene-($C_6$-$C_{14}$)-aryl-($C_0$-$C_4$)-alkylene-O-PG2,
9) —($C_0$-$C_8$)-alkylene-C(O)—O-PG3,
10) —($C_0$-$C_4$)-alkylene-($C_6$-$C_{14}$)-aryl-($C_0$-$C_4$)-alkylene-C(O)—O-PG3 or
11) hydrogen atom,
R4 is —N(R6)$_2$,
where R6 are identical or different and are independently of one another
1) hydrogen atom,
2) —($C_1$-$C_6$)-alkyl,
3) —($C_0$-$C_4$)-alkylene-($C_3$-$C_{12}$)-cycloalkyl, where cycloalkyl is unsubstituted or substituted independently of one another once, twice, three or four times by R11, halogen, —C(O)—O—R11, —($C_1$-$C_4$)-alkyl-O—R11 or —O—($C_1$-$C_4$)-alkyl,
4) —($C_0$-$C_6$)-alkylene-(C6-C14)-aryl, where aryl and alkylene are unsubstituted or substituted independently of one another once, twice, three or four times by R11, halogen, —C(O)—O—R11, —($C_1$-$C_4$)-alkyl-O—R11, —C(O)—N(R8)$_2$ or —O—($C_1$-$C_4$)-alkyl,
5) —($C_0$-$C_8$)-alkylene-N(R5)-PG1,
6) —($C_0$-$C_4$)-alkylene-($C_6$-$C_{14}$)-aryl-($C_0$-$C_4$)-alkyl-N(R5)-PG1,
7) —($C_0$-$C_8$)-alkylene-O-PG2,
8) —($C_0$-$C_4$)-alkylene-($C_6$-$C_{14}$)-aryl-($C_0$-$C_4$)-alkyl-O-PG2,
9) —($C_0$-$C_8$)-alkylene-C(O)—O—R11,
10) —($C_0$-$C_4$)-alkylene-($C_6$-$C_{14}$)-aryl-($C_0$-$C_4$)-alkyl-C(O)—O-PG3,
11) —($C_0$-$C_4$)-alkylene-Het, which means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —($C_1$-$C_4$)-alkyl-O—R11 or —O—($C_1$-$C_4$)-alkyl,
12) —($C_1$-$C_3$)-fluoroalkyl,
13) —($C_0$-$C_4$)-alkylene-CH(R11)-C(O)—NH$_2$,
14) —($C_0$-$C_4$)-alkylene-CH(R11)-C(O)—NH—($C_1$-$C_4$)-alkyl,
15) —($C_0$-$C_4$)-alkylene-CH(R11)-C(O)—NH—CH(R12)-R13, or
16) amino acid, where the linkage of the amino acid takes place by a peptide linkage, and the carboxyl radical of the amino acid is unsubstituted or substituted by PG3 or by —N(R5)$_2$,
or the two R6 radicals taken together with the N atom to which they are bonded form a mono- or bicyclic ring having 4 to 9 ring atoms which is saturated, partly saturated or aromatic, where the ring is unsubstituted or substituted once or twice by —($C_1$-$C_4$)-alkyl, —C(O)—O—R11, halogen, —($C_1$-$C_4$)-alkyl-O—R11 or phenyl,
R5 is hydrogen atom or —($C_1$-$C_6$)-alkyl,
PG1 is protective group for the amino function,
PG2 is protective group for the hydroxy function,
PG3 is protective group for the carboxyl function,
R7 is hydrogen atom or —($C_1$-$C_6$)-alkyl,
R8 is hydrogen atom or —($C_1$-$C_6$)-alkyl,
R9 is hydrogen atom or —($C_1$-$C_6$)-alkyl,
R11 and R12 are identical or different and are independently of one another 1) hydrogen atom,
2) —($C_1$-$C_6$)-alkyl,
3) —($C_0$-$C_4$)-alkylene-phenyl, where phenyl is unsubstituted or substituted independently of one another once, twice or three times by halogen, —OH or —O—($C_1$-$C_4$)-alkyl,
4) —($C_0$-$C_4$)-alkylene-($C_3$-$C_{12}$)-cycloalkyl, where cycloalkyl is unsubstituted or substituted independently of one another once, twice, three or four times by R13, halogen, —C(O)—O—R13, —($C_1$-$C_4$)-alkyl-O—R13, —O—($C_1$-$C_4$)-alkyl or —($C_0$-$C_4$)-alkylene-phenyl,
5) —($C_0$-$C_4$)-alkylene-C(O)—N(R13)$_2$ or
6) —($C_0$-$C_4$)-alkylene-indolyl,
R13 is 1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14,
R14 is hydrogen atom, —($C_1$-$C_4$)-alkyl, —NH$_2$ or —OH, and
R15 is hydrogen atom, —($C_1$-$C_4$)-alkyl, —O—CF$_3$, —NH$_2$, —OH, —CF$_3$ or halogen, and/or of a stereoisomeric form of the compound of the formula I and/or mixture of these forms in any ratio, and/or a physiologically tolerated salt of the compound of the formula I.

The use of the compound of formula I of the invention which is suitable for a prophylactic and for a therapeutic use in a human suffering from one or more disorder(s) associated with thromboses, embolisms, hypercoagulability or fibrotic changes comprising administering the compound to the human in need thereof. They can be employed for secondary prevention and are suitable both for acute and for long-term therapy.

The compound of formula I is also useful for the manufacture of a medicament for the prophylaxis, secondary prevention and therapy of one or more disorders associated with thromboses, embolisms, hypercoagulability or fibrotic changes.

DETAILED DESCRIPTION OF THE INVENTION

Definitions

The term "($C_1$-$C_6$)-alkyl" means hydrocarbon radicals whose carbon chain is straight-chain or branched and comprises 1 to 6 carbon atoms, for example methyl, ethyl, propyl, isopropyl, butyl, isobutyl, tertiary butyl, pentyl, isopentyl, neopentyl, hexyl, 2,3-dimethylbutane or neohexyl.

The term "—($C_0$-$C_4$)-alkylene" means hydrocarbon radicals whose carbon chain is straight-chain or branched and comprises 1 to 4 carbon atoms, for example methylene, ethylene, propylene, isopropylene, isobutylene, butylene or tertiary butylene. "—$C_0$-Alkylene" is a covalent bond.

The term "—(CH$_2$)$_n$— in which n is the integer zero or 1" means the methylene radical in the case where n equals 1, and the radical has the meaning of a covalent bond in the case where n is the integer zero.

The term "—($C_1$-$C_4$)-alkylene" means hydrocarbon radicals whose carbon chain is straight-chain or branched and comprises 1 to 4 carbon atoms, for example methylene (—CH$_2$—), ethylene (—CH$_2$—CH$_2$—), propylene (—CH$_2$—CH$_2$—CH$_2$—), isopropylene, isobutylene, butylene or tertiary butylene.

The term "—(CH$_2$)$_n$— in which n is the integer zero, 1, 2 or 3" means radicals such as methylene, ethylene or propylene. In the case where n is the integer zero, the radical has the meaning of a covalent bond.

The term "(C$_3$-C$_{12}$)-cycloalkyl" means radicals such as compounds derived from 3- to 12-membered mono-, bi- or tricycles or bridged rings such as the monocycles cyclopropane, cyclobutane, cyclopentane, cyclohexane, cycloheptane or cyclooctane, derived from the bicycles bicyclo[4.2.0]octane, octahydroindene, decahydronaphthalene, decahydroazulene, decahydrobenzocycloheptene or dodecahydroheptalene, or from tricycles such as adamantine, or derived from the bridged rings such as spiro[2.5]octane, spiro[3.4]octane, spiro[3.5]nonane, bicyclo[3.1.1]heptane, bicyclo[2.2.1]heptane, bicyclo[2.2.2]octane or octahydro-4,7-methanindene.

The term "R6 form together with the N atom to which they are bonded a mono- or bicyclic ring having 4 to 9 ring atoms" means radicals such as compounds derived from 4- to 8-membered monocycles which may be saturated or wholly or partly aromatic, for example azetidine, dihydroazete, azete, diazetidine, diazete, pyrrolidine, dihydropyrrole, pyrrole, imidazolidine, dihydroimidazole, imidazole, pyrazoline, pyrazolidine, piperidine, dihydropyridine, tetrahydropyridine, pyridine, piperazine, dihydropyrazine, pyrazine, pyridazine, pyrimidine, oxazine, azepane, tetrahydroazepine, azepine, azocan, dihydroazocine, hexohydroazocine or azocine or bicyclic rings such as 2-azabicyclo[3.2.2]nonane or, 7-azabicyclo[2.2.1]heptane.

The term "—(C$_6$-C$_{14}$)-aryl" means aromatic carbon radicals having 6 to 14 carbon atoms in the ring. Examples of —(C$_6$-C$_{14}$)-aryl radicals are phenyl, naphthyl, for example 1-naphthyl, 2-naphthyl, 1,2,3,4-tetrahydronaphthalenyl, anthryl or fluorenyl. Naphthyl radicals and especially phenyl radicals are preferred aryl radicals.

The term "4- to 15-membered Het ring" or "Het" means ring systems having 4 to 15 carbon atoms which are present in one, two or three ring systems connected together and which comprise one, two, three or four identical or different heteroatoms selected from the group consisting of oxygen, nitrogen and sulfur. Examples of these ring systems are the radicals acridinyl, azepinyl, azetidinyl, aziridinyl, benzimidazalinyl, benzimidazolyl, benzo[1,3]dioxol, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadizinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl.

Preferred Het rings are the radicals isoxazolyl, benzo[1,3]dioxole and thiophenyl.

The term "halogen" means fluorine, chlorine, bromine or iodine, preferably fluorine, chlorine or bromine, especially chlorine or bromine.

The term "amino acid" means compounds such as naturally occurring α-amino acids glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid. Histidine, tryptophan, serine, threonine, cysteine, methionine, asparagine, glutamine, lysine, arginine, glutamic acid and aspartic acid are particularly preferred. Also included therewith are non-naturally occurring amino acids such as 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, phenylglycine, 3-(2-thienyl)alanine, 3-(3-thienyl)alanine, sarcosine, 2-(2-thienyl)glycine, 2-aminoheptanoic acid, pipecolic acid, hydroxylysine, N-methylisoleucine, 6-N-methyllysine, N-methylvaline, norvaline, norleucine, ornithine, allo-isoleucine, 4-hydroxyproline, allo-hydroxylysine, allo-threonine, 3-hydroxyproline, 3-(2-naphtyl)alanine, 3-(1-naphtylalanine), homophenylalanine, homocysteine, 2-amino-3-phenylaminoethylpropionic acid, homocysteic acid, homotryptophan, cysteic acid, 3-(2-pyridyl)alanine, 3-(3-pyridyl)alanine, 3-(4-pyridyl)alanine, phosphinothricin, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan or 2-amino-3-phenylaminopropionic acid.

The term "peptide linkage" means structures such as

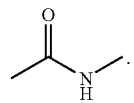

The term "protective group for the amino, carboxyl or for the hydroxy function" means protective groups such as suitable protective groups for amino functions, for example the t-butoxycarbonyl, the benzyloxycarbonyl or the phthalolyl group, and the trityl or tosyl protective group, suitable protective groups for the carboxyl function are for example, alkyl, aryl or arylalkyl esters and suitable protective groups for the hydroxy function are for example alkyl esters, t-butyl, benzyl or trityl groups. Protective groups can be introduced and removed by techniques which are well known or described herein (see Green, T. W., Wutz, P. G. M., Protective Groups in Organic Synthesis (1991), 2nd Ed., Wiley-Interscience, or Kocienski, P., Protecting Groups (1994), Thieme).

The term "—(C$_1$-C$_3$)-fluoroalkyl" means a partly or completely fluorinated alkyl radical derived for example from the following radicals —CF$_3$, —CHF$_2$, —CH$_2$F, —CHF—CF$_3$, —CHF—CHF$_2$, —CHF—CH$_2$F, —CH$_2$—CF$_3$, —CH$_2$—CHF$_2$, —CH$_2$—CH$_2$F, —CF$_2$—CF$_3$, —CF$_2$—CHF$_2$, —CF$_2$—CH$_2$F, —CH$_2$—CHF—CF$_3$, —CH$_2$—CHF—CHF$_2$, —CH$_2$—CHF—CH$_2$F, —CH$_2$—CH$_2$—CF$_3$, —CH$_2$—CH$_2$—CHF$_2$, —CH$_2$—CH$_2$—CH$_2$F, —CH$_2$—

$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—$S(O)_2$-" means a sulfonyl radical.
The term "—C(O)-" means a carbonyl radical.
Embodiments The invention also relates to the use of the compound of the formula I where X is —C(O)—.

The invention also relates to the use of the compound of the formula I where X is —$S(O)_2$—.

The invention also relates to the use of the compound of the formula I where X is —C(O)—, R1 is 1) hydrogen atom or
2) —($C_1$-$C_4$)-alkyl, R2 is 1) —($C_1$-$C_6$)-alkylene-$NH_2$,
2) —($C_0$-$C_4$)-alkylene-pyridyl-$NH_2$,
3) —($C_0$-$C_4$)-alkylene-piperidinyl-$NH_2$,
4) —($C_0$-$C_4$)-alkylene-thiazolyl-$NH_2$,
5) —($C_1$-$C_6$)-alkylene-NH—C(=NH)—$NH_2$,
6) —($C_0$-$C_4$)-alkylene-($C_3$-$C_8$)-cycloalkyl-$NH_2$,
7) —($C_1$-$C_6$)-alkylene-NH—C(=NH)—($C_1$-$C_4$)-alkyl,
8) —($C_0$-$C_4$)-alkylene-O—NH—C(=NH)—$NH_2$,
9) —($C_1$-$C_6$)-alkylene-NH—C(O)—O—($C_1$-$C_4$)-alkylene-($C_6$-$C_{14}$)-aryl, where aryl is unsubstituted or substituted by —$NH_2$ or is substituted by —$NH_2$ and once, twice or three times by R15,
10) —($C_0$-$C_4$)-alkylene-NH—C(O)—($C_1$-$C_4$)-alkyl,
11) —($C_0$-$C_4$)-alkylene-($C_6$-$C_{14}$)-aryl, where aryl is unsubstituted or substituted by —$NH_2$, or is substituted by —$NH_2$ and once, twice or three times by R15, or
12) —($C_1$-$C_4$)-alkylene—$SO_x$—($C_1$-$C_4$)-alkylene-$NH_2$ in which x is the integer zero, 1 or 2

R3 is 1) —($C_1$-$C_4$)-alkyl),
2) —($C_0$-$C_4$)-alkylene-($C_3$-$C_8$)-cycloalkyl,
3) —($C_1$-$C_6$)-alkylene-(C6-C14)-aryl, where aryl is substituted independently of one another once, twice or three times by R15,
4) —($C_1$-$C_6$)-alkylene-NH—C(O)—O—($C_1$-$C_4$)-alkylene-(C6-C14)-aryl, where aryl is substituted independently of one another once, twice or three times by R15,
5) —($C_1$-$C_6$)-alkylene-NH-PG1,
6) —($C_1$-$C_6$)-alkylene-O-PG2,
7) —($C_1$-$C_6$)-alkyl), or
8) hydrogen atom,
where PG1 is t-butyloxycarbonyl or benzyloxycarbonyl, and where PG2 is t-butyl-, t-butyloxycarbonyl or benzyloxycarbonyl, R4 is —$N(R6)_2$,
where R6 are identical or different and are independently of one another
1) hydrogen atom,
2) —($C_1$-$C_6$)-alkyl,
3) —($C_0$-$C_4$)-alkylene-($C_3$-$C_{12}$)-cycloalkyl, where cycloalkyl is unsubstituted or substituted independently of one another once, twice, three or four times by R11, halogen, —C(O)—O—R11, —($C_1$-$C_4$)-alkyl-O—R11 or —O—($C_1$-$C_4$)-alkyl,
4) —($C_0$-$C_4$)-alkylene-C(R11)(R12)-($C_3$-$C_{12}$)-cycloalkyl, where cycloalkyl is unsubstituted or substituted independently of one another once, twice or three times by R11, halogen, —C(O)—O—R11, —($C_1$-$C_4$)-alkyl-O—R11 or —O—($C_1$-$C_4$)-alkyl,
5) —($C_0$-$C_4$)-alkylene-Het, which means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —($C_1$-$C_4$)-alkyl-O—R11 or —O—($C_1$-$C_4$)-alkyl,
6) —($C_0$-$C_6$)-alkylene-(C6-C14)-aryl, where aryl or alkylene is unsubstituted or substituted independently of one another once, twice or three times by R11, halogen, —C(O)—O—R11, —($C_0$-$C_4$)-alkyl-O—R11 or —O—($C_1$-$C_4$)-alkyl,
7) —($C_0$-$C_4$)-alkylene-C(R11)(R12)-aryl, where aryl or alkylene is unsubstituted or substituted independently of one another once, twice or three times by R11, halogen, —C(O)—O—R11, —($C_0$-$C_4$)-alkyl-O—R11 or —O—($C_1$-$C_4$)-alkyl,
8) 1,2,3,4-tetrahydronaphthalenyl,
9) —($C_0$-$C_4$)-alkylene-CH(R11)-C(O)—$NH_2$,
10) —($C_0$-$C_4$)-alkylene-CH(R11)-C(O)—NH—($C_1$-$C_4$)-alkyl,
11) —($C_0$-$C_4$)-alkylene-CH(R11)-C(O)—NH—CH(R12)-R13,
12) —($C_0$-$C_6$)-alkylene-C(O)—O—R11, where alkylene is unsubstituted or substituted independently of one another once or twice by R11, halogen, —C(O)—O—R11, —($C_1$-$C_4$)-alkyl-O—R11 or —O—($C_1$-$C_4$)-alkyl,
13) —($C_0$-$C_4$)-alkylene-C(R11)(R12)-C(O)—O—R11, or
14) —($C_1$-$C_3$)-fluoroalkyl,
or the two R6 radicals taken together with the N atom to which they are bonded form a mono- or bicyclic ring having 4 to 9 ring atoms which is saturated, partly saturated or aromatic, where the ring is unsubstituted or substituted once or twice by —($C_1$-$C_4$)-alkyl, —C(O)—O—R11, halogen, —($C_1$-$C_4$)-alkyl-O—R11 or phenyl, R7 is hydrogen atom or —($C_1$-$C_4$)-alkyl,
R9 is hydrogen atom or —($C_1$-$C_4$)-alkyl,
R11 and R12 are identical or different and are independently of one another
1) hydrogen atom,
2) —($C_1$-$C_4$)-alkyl,
3) —($C_0$-$C_4$)-alkylene-phenyl, where phenyl is unsubstituted or substituted independently of one another once, twice or three times by halogen, —OH or —O—($C_1$-$C_4$)-alkyl,
4) —($C_0$-$C_4$)-alkylene-($C_3$-$C_{12}$)-cycloalkyl, where cycloalkyl is unsubstituted or substituted independently of one another once, twice, three or four times by R13, halogen, —C(O)—O—R13, —($C_1$-$C_4$)-alkyl-O—R13, —O—($C_1$-$C_4$)-alkyl or —($C_0$-$C_4$)-alkylene-phenyl,
5) —($C_0$-$C_4$)-alkylene-C(O)—$N(R13)_2$, or
6) —($C_0$-$C_4$)-alkylene-indolyl, R13 is 1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14, R14 is hydrogen atom, —($C_1$-$C_4$)-alkyl, —$NH_2$, or —OH, and R15 is hydrogen atom, —($C_1$-$C_4$)-alkyl, —O—$CF_3$, —$NH_2$, —OH, —$CF_3$, or halogen.

The invention also relates to the use of the compound of the formula I where

X is —C(O)—,

R1 is 1) hydrogen atom or
2) —($C_1$-$C_4$)-alkyl,

R2 is 1) —($C_1$-$C_6$)-alkylene-$NH_2$,
2) —($C_1$-$C_4$)-alkylene-pyridyl-$NH_2$,
3) —($C_1$-$C_4$)-alkylene-piperidinyl-$NH_2$,
4) —($C_1$-$C_6$)-alkylene-NH—C(=NH)—$NH_2$,
5) —($C_0$-$C_4$)-alkylene-($C_3$-$C_6$)-cycloalkyl-$NH_2$,
6) —($C_1$-$C_6$)-alkylene-NH—C(=NH)—($C_1$-$C_4$)-alkyl,
7) —($C_1$-$C_4$)-alkylene-O—NH—C(=NH)—$NH_2$,
8) —($C_1$-$C_6$)-alkylene-NH—C(O)—O—($C_1$-$C_4$)-alkylene-phenyl, where phenyl is unsubstituted or substituted independently of one another once, twice or three times by R15 is this properly dependent,
9) —($C_1$-$C_4$)-alkylene-NH—C(O)—($C_1$-$C_6$)-alkyl,
10) —($C_1$-$C_4$)-alkylene-phenyl, where phenyl is substituted independently of one another once, twice or three times by R15 is this properly dependent,
11) —($C_1$-$C_4$)-alkylene-$SO_2$—($C_1$-$C_4$)-alkylene-$NH_2$ or
12) —($C_1$-$C_4$ does not properly depend)-alkylene-S—($C_1$-$C_4$)-alkylene-$NH_2$, R3 is 1) —($C_1$-$C_4$)-alkyl,
2) —($C_1$-$C_4$)-alkylene-($C_3$-$C_6$)-cycloalkyl,
3) —($C_1$-$C_4$)-alkylene-phenyl, where phenyl is unsubstituted or substituted by —$NH_2$ or is substituted by —$NH_2$ and once, twice or three times by R15,
4) —($C_1$-$C_6$)-alkylene-NH—C(O)—O—($C_1$-$C_4$)-alkylene-phenyl, where phenyl is unsubstituted or substituted by —$NH_2$ or is substituted by —$NH_2$ and once, twice or three times by R15,
5) hydrogen atom, R4 is —N(R6)$_2$,
where R6 are identical or different and are independently of one another
1) hydrogen atom,
2) —($C_1$-$C_4$)-alkyl,
3) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, bicyclo[3.1.1]heptanyl, decahydronaphthalenyl, tetrahydro-naphthalenyl, octahydro-4,7-methanoindenyl or bicyclo[2.2.1]heptanyl, and which cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen,
4) —($C_0$-$C_4$)-alkylene-C(R11)(R12) is this properly dependent —($C_3$-$C_{12}$)-cycloalkyl, where cycloalkyl is selected from the group consisting of cyclohexyl, cyclopentyl, cyclobutyl, cyclopropyl, adamantanyl, bicyclo[3.1.1]heptanyl, decahydronaphthalenyl, tetrahydronaphthalenyl, octahydro-4,7-methanoindenyl or bicyclo[2.2.1]heptanyl and in which cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen,
5) —($C_0$-$C_4$)-alkylene-Het, which is selected from the group consisting of acridinyl, azepinyl, azetidinyl, aziridinyl, benzimidazalinyl, benzimidazolyl, benzo[1,3]dioxolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH is there any issue with this numerical designation-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl, where Het or alkylene is unsubstituted or substituted independently of one another once or twice by —($C_1$-$C_4$)-alkyl,
6) —($C_1$-$C_6$)-alkylene-phenyl, where phenyl or alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl,
7) —($C_0$-$C_4$)-alkylene-C(R11)(R12)-phenyl, where phenyl is unsubstituted or substituted independently of one another once, twice or three times by phenyl or fluorine,
8) 1,2,3,4-tetrahydronaphthalenyl,
9) —($C_0$-$C_4$)-alkylene-CH(R11)-C(O)—$NH_2$,
10) —($C_0$-$C_4$)-alkylene-CH(R11)-C(O)—NH—($C_1$-$C_4$)-alkyl,
11) —($C_0$-$C_4$)-alkylene-CH(R11)-C(O)—NH—CH(R12)-R13,
12) —($C_1$-$C_6$)-alkylene-C(O)—O—R11, where alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl,
13) —($C_0$-$C_4$)-alkylene-C(R11)(R12)-C(O)—O—R11, or
14) —($C_1$-$C_3$)-fluoroalkyl,
or the two R6 radicals taken together with the N atom to which they are bonded form a mono- or bicyclic ring selected from the group consisting of pyrrolidine, piperidine, 2-aza-bicyclo[3.2.2]nonane and 7-aza-bicyclo[2.2.1]heptane, where the ring is unsubstituted or substituted once or twice by —($C_1$-$C_4$)-alkyl, —C(O)—O—R11, —($C_1$-$C_4$)-alkyl-O—R11 or phenyl, R7 is hydrogen atom or —($C_1$-$C_4$)-alkyl,
R9 is hydrogen atom or —($C_1$-$C_4$)-alkyl,
R11 and R12 are identical or different and are independently of one another 1) hydrogen atom,
2) —(C$_1$-C$_4$)-alkyl,
3) —(C$_0$-C$_4$)-alkylene-phenyl, where phenyl is unsubstituted or substituted independently of one another once, twice or three times by —OH, halogen or —O—(C$_1$-C$_4$)-alkyl,
4) —(C$_0$-C$_4$)-alkylene-(C$_3$-C$_{12}$)-cycloalkyl, where cycloalkyl is selected from the group consisting of cyclohexyl, cyclopentyl, cyclobutyl, cyclopropyl, adamantanyl, bicyclo[3.1.1]heptanyl, octahydro-4,7-methanoindenyl and bicyclo[2.2.1]heptanyl and where cycloalkyl is unsubstituted or substituted independently of one another once, twice, three or four times by —(C$_1$-C$_4$)-alkyl, —C(O)—O—R13 or phenyl, or
5) —(C$_0$-C$_4$)-alkylene-indolyl,
R13 is 1) hydrogen atom,
2) —(C$_1$-C$_4$)-alkyl,
3) —(C$_0$-C$_4$)-alkylene-C(O)—O—R14,
4) —(C$_0$-C$_4$)-alkylene-C(O)—R14 or
5) —(C$_0$-C$_4$)-alkylene-O—R14, and
R14 is hydrogen atom, —(C$_1$-C$_4$)-alkyl, —NH$_2$ or —OH and
R15 is hydrogen atom, —(C$_1$-C$_4$)-alkyl, —O—CF$_3$, —NH$_2$, —OH, —CF$_3$ or halogen.

The invention also relates to the use of the compound of the formula I where
X is —C(O)—,
R1 is 1) hydrogen atom or
2) —(C$_1$-C$_4$)-alkyl,
R2 is 1) —(C$_1$-C$_6$)-alkylene-NH$_2$,
2) —(C$_1$-C$_4$)-alkylene-pyridyl-NH$_2$,
3) —(C$_1$-C$_4$)-alkylene-piperidinyl-NH$_2$,
4) —(C$_1$-C$_4$)-alkylene-NH—C(=NH)—NH$_2$,
5) —(C$_1$-C$_6$)-alkylene-NH—C(=NH)—(C$_1$-C$_4$)-alkyl,
6) —(C$_1$-C$_4$)-alkylene-(C$_3$-C$_6$)-cycloalkyl-NH$_2$,
7) —(C$_1$-C$_4$)-alkylene-O—NH—C(=NH)—NH$_2$,
8) —(C$_1$-C$_6$)-alkylene-NH—C(O)—O—(C$_1$-C$_4$)-alkylene-phenyl,
9) —(C$_1$-C$_4$)-alkylene-NH—C(O)—(C$_1$-C$_6$)-alkyl
10) —(C$_1$-C$_4$)-alkylene-phenyl-NH$_2$,
11) —(C$_1$-C$_2$)-alkylene-SO$_2$—(C$_1$-C$_4$)-alkylene-NH$_2$ or
12) —(C$_1$-C$_2$)-alkylene-S—(C$_1$-C$_4$)-alkylene-NH2,
R3 is 1) —(C$_1$-C$_4$)-alkyl,
2) —(C$_1$-C$_4$)-alkylene-(C$_3$-C$_6$)-cycloalkyl,
3) —(C$_1$-C$_4$)-alkylene-phenyl, where phenyl is unsubstituted or substituted by —OH,
4) —(C$_1$-C$_6$)-alkylene-NH—C(O)—O—(C$_1$-C$_4$)-alkylene-phenyl,
5) hydrogen atom,
R4 is —N(R6)$_2$,
where R6 are identical or different and are independently of one another
1) hydrogen atom,
2) —(C$_1$-C$_6$)-alkyl,
3) —(C$_0$-C$_4$)-alkylene-(C$_3$-C$_8$)-cycloalkyl, where cycloalkyl is selected from the group consisting of cyclohexyl, cyclopentyl, cyclopropyl, adamantanyl, 1,7,7-trimethylbicyclo[3.1.1]heptanyl, tetrahydronaphthalenyl, decahydro-naphthalenyl, octahydro-4,7-methanoindenyl and bicyclo[2.2.1]heptanyl and where cycloalkyl is unsubstituted or substituted independently of one another once, twice or three times by —(C$_1$-C$_4$)-alkyl or phenyl,
4) —C(R11)(R12)-adamantanyl,
5) —CH(R11)-C(O)—NH—CH(R12)-R13,
6) —(C$_0$-C$_4$)-alkylene-Het, where Het is selected from the group consisting of benzimidazolyl, isoxazolyl, piperidinyl, pyridinyl, pyrrolidinyl, thiophenyl and benzo[1,3]dioxolyl,
7) 1,2,3,4-tetrahydronaphthalenyl,
8) —(C$_0$-C$_4$)-alkylene-C(R11)(R12)-phenyl, where phenyl is unsubstituted or substituted independently of one another once, twice or three times by phenyl or fluorine,
9) —CH(R11)-C(O)—NH$_2$,
10) —CH(R11)-C(O)—NH—CH(R12)-CH$_2$—OH,
11) —(C$_1$-C$_6$)-alkylene-phenyl, where phenyl or alkylene is unsubstituted or substituted independently of one another once or twice by chlorine, fluorine, —C(O)—O—R11, —(C$_1$-C$_4$)-alkyl-O—R11, —O—(C$_1$-C$_4$)-alkyl, phenyl or —(C$_1$-C$_4$)-alkyl,
12) —CH(R11)-C(O)—NH—(C$_1$-C$_4$)-alkyl,
13) —(C$_0$-C$_4$)-alkylene-C(R11)(R12)-bicyclo[3.1.1]heptanyl, where bicyclo[3.1.1]heptanyl is unsubstituted or substituted once to four times by —(C$_1$-C$_4$)-alkyl,
14) —(C$_1$-C$_6$)-alkylene-C(O)—O—R11, where alkylene is unsubstituted or substituted independently of one another once or twice by chlorine, fluorine, —C(O)—O—R11, —(C$_1$-C$_4$)-alkyl-O—R11, —O—(C$_1$-C$_4$)-alkyl, phenyl or —(C$_1$-C$_4$)-alkyl,
15) —(C$_0$-C$_4$)-alkylene-C(R11)(R12)-C(O)—O—R11, or
16) —CH$_2$—CF$_2$—CF$_3$,
or the two R6 radicals taken together with the N atom to which they are bonded form a mono- or bicyclic ring selected from the group consisting of pyrrolidines, 2-azabicyclo[3.2.2]nonane and 7-aza-bicyclo[2.2.1]heptane, where the ring is unsubstituted or substituted independently one of another (inadvertent absence?) once or twice by —(C$_1$-C$_4$)-alkyl, —C(O)—O—R11, —(C$_1$-C$_4$)-alkyl-O—R11 or phenyl,
R7 is hydrogen atom or —(C$_1$-C$_4$)-alkyl,
R9 is hydrogen atom or —(C$_1$-C$_4$)-alkyl,
R11 and R12 are identical or different and are independently of one another
1) hydrogen atom,
2) —(C$_1$-C$_4$)-alkyl,
3) —(C$_0$-C$_4$)-alkylene-phenyl, where phenyl is unsubstituted or substituted independently of one another once, twice or three times by —OH, halogen or —O—(C$_1$-C$_4$)-alkyl,
4) —(C$_0$-C$_4$)-alkylene-(C$_3$-C$_{12}$)-cycloalkyl, where cycloalkyl is selected from the group consisting of cyclohexyl, cyclopentyl, cyclobutyl, cyclopropyl, adamantanyl, 1,7,7-trimethylbicyclo[3.1.1]heptanyl, octahydro-4,7-methano-indenyl and bicyclo[2.2.1]heptanyl and where cycloalkyl is unsubstituted or substituted independently of one another once, twice, three or four times by —(C$_1$-C$_4$)-alkyl, —C(O)—O—R13 or phenyl or
5) —(C$_0$-C$_4$)-alkylene-indolyl,
R13 is 1) hydrogen atom,
2) —(C$_1$-C$_4$)-alkyl,
3) —(C$_0$-C$_4$)-alkylene-C(O)—O—R14,
4) —(C$_0$-C$_4$)-alkylene-C(O)—R14 or
5) —(C$_0$-C$_4$)-alkylene-O—R14,
R14 is hydrogen atom, —(C$_1$-C$_4$)-alkyl, —NH$_2$ or —OH and
R15 is hydrogen atom, —(C$_1$-C$_4$)-alkyl, —O—CF$_3$, —NH$_2$, —OH, —CF$_3$ or halogen.

The invention also relates to the use of the compound of the formula I where
X is —S(O)$_2$—,
R1 is 1) hydrogen atom or
2) —(C$_1$-C$_4$)-alkyl, R2 is 1) —($C_1$-$C_6$)-alkylene-$NH_2$,
   2) —($C_0$-$C_4$)-alkylene-pyridyl-$NH_2$,
   3) —($C_0$-$C_4$)-alkylene-piperidinyl-$NH_2$,
   4) —($C_0$-$C_4$)-alkylene-thiazolyl-$NH_2$,
   5) —($C_1$-$C_6$)-alkylene-NH—C(=NH)—$NH_2$,
   6) —($C_0$-$C_4$)-alkylene-($C_3$-$C_8$)-cycloalkyl-$NH_2$,
   7) —($C_1$-$C_6$)-alkylene-NH—C(=NH)—($C_1$-$C_4$)-alkyl,
   8) —($C_0$-$C_4$)-alkylene-O—NH—C(=NH)—$NH_2$,
   9) —($C_1$-$C_6$)-alkylene-NH—C(O)—O—($C_1$-$C_4$)-alkylene-(C6-C14)-aryl, where aryl is unsubstituted or substituted by —$NH_2$ or is substituted by —$NH_2$ and once, twice or three times by R15,
   10) —($C_0$-$C_4$)-alkylene-NH—C(O)—($C_1$-$C_4$)-alkyl,
   11) —($C_0$-$C_4$)-alkylene-($C_6$-$C_{14}$)-aryl, where aryl is unsubstituted or substituted by —$NH_2$ or is substituted by —$NH_2$ and once, twice or three times by R15, or
   12) —($C_1$-$C_4$)-alkylene-$SO_x$—($C_1$-$C_4$)-alkylene-$NH_2$ in which x is the integer zero, 1 or 2,
R3 is 1) —($C_1$-$C_4$)-alkyl,
   2) —($C_0$-$C_4$)-alkylene-($C_3$-$C_8$)-cycloalkyl,
   3) —($C_1$-$C_6$)-alkylene-($C_6$-$C_{14}$)-aryl, where aryl is substituted independently of one another once, twice or three times by R15,
   4) —($C_1$-$C_6$)-alkylene-NH—C(O)—O—($C_1$-$C_4$)-alkylene-($C_6$-$C_{14}$)-aryl, where aryl is substituted independently of one another once, twice or three times by R15,
   5) —($C_1$-$C_6$)-alkylene-NH-PG1,
   6) —($C_1$-$C_6$)-alkylene-O-PG2,
   7) —($C_1$-$C_6$)-alkyl, or
   8) hydrogen atom,
   where PG1 is t-butyloxycarbonyl or benzyloxycarbonyl and PG2 is t-butyl-, t-butyloxycarbonyl or benzyloxycarbonyl,
R4 is —N(R6)$_2$,
   where R6 are identical or different and are independently of one another
   1) hydrogen atom,
   2) —($C_1$-$C_6$)-alkyl,
   3) —($C_0$-$C_4$)-alkylene-($C_3$-$C_{12}$)-cycloalkyl, where cycloalkyl is unsubstituted or substituted independently of one another once, twice, three or four times by R11, halogen, —C(O)—O—R11, —($C_1$-$C_4$)-alkyl-O—R11 or —O—($C_1$-$C_4$)-alkyl,
   4) —($C_0$-$C_4$)-alkylene-C(R11)(R12)-($C_3$-$C_{12}$)-cycloalkyl, where cycloalkyl is unsubstituted or substituted independently of one another once, twice or three times by R11, halogen, —C(O)—O—R11, —($C_1$-$C_4$)-alkyl-O—R11 or —O—($C_1$-$C_4$)-alkyl,
   5) —($C_0$-$C_4$)-alkylene-Het, which means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —($C_1$-$C_4$)-alkyl-O—R11 or —O—($C_1$-$C_4$)-alkyl,
   6) —($C_0$-$C_6$)-alkylene-($C_6$-$C_{14}$)-aryl, where aryl or alkylene are unsubstituted or substituted independently of one another once, twice or three times by R11, halogen, —C(O)—O—R11, —($C_0$-$C_4$)-alkyl-O—R11 or —O—($C_1$-$C_4$)-alkyl,
   7) —($C_0$-$C_4$)-alkylene-C(R11)(R12)-($C_6$-$C_{14}$)-aryl, where aryl or alkylene is unsubstituted or substituted independently of one another once, twice or three times by R11, halogen, —C(O)—O—R11, —($C_0$-$C_4$)-alkyl-O—R11 or —O—($C_1$-$C_4$)-alkyl,
   8) 1,2,3,4-tetrahydronaphthalenyl,
   9) —($C_0$-$C_4$)-alkylene-CH(R11)-C(O)—$NH_2$,
   10) —($C_0$-$C_4$)-alkylene-CH(R11)-C(O)—NH—($C_1$-$C_4$)-alkyl,
   11) —($C_0$-$C_4$)-alkylene-CH(R11)-C(O)—NH—CH(R12)-R13,
   12) —($C_0$-$C_6$)-alkylene-C(O)—O—R11, where alkylene is unsubstituted or substituted independently of one another once or twice by R11, halogen, —C(O)—O—R11, —($C_1$-$C_4$)-alkyl-O—R11 or —O—($C_1$-$C_4$)-alkyl,
   13) —($C_0$-$C_4$)-alkylene-C(R11)(R12)-C(O)—O—R11, or
   14) —($C_1$-$C_3$)-fluoroalkyl,
   or the two R6 radicals taken together with the N atom to which they are bonded form a mono- or bicyclic ring having 4 to 9 ring atoms which is saturated, partly saturated or aromatic, where the ring is unsubstituted or substituted once or twice by —($C_1$-$C_4$)-alkyl, —C(O)—O—R11, halogen, —($C_1$-$C_4$)-alkyl-O—R11 or phenyl,
R7 is hydrogen atom or —($C_1$-$C_4$)-alkyl,
R9 is hydrogen atom or —($C_1$-$C_4$)-alkyl,
R11 and R12 are identical or different and are independently of one another
   1) hydrogen atom,
   2) —($C_1$-$C_4$)-alkyl,
   3) —($C_0$-$C_4$)-alkylene-phenyl, where phenyl is unsubstituted or substituted independently of one another once, twice or three times by halogen, —OH or —O—($C_1$-$C_4$)-alkyl,
   4) —($C_0$-$C_4$)-alkylene-($C_3$-$C_{12}$)-cycloalkyl, where cycloalkyl is unsubstituted or substituted independently of one another once, twice, three or four times by R13, halogen, —C(O)—O—R13, —($C_1$-$C_4$)-alkyl-O—R13, —O—($C_1$-$C_4$)-alkyl or —($C_0$-$C_4$)-alkylene-phenyl,
   5) —($C_0$-$C_4$)-alkylene-C(O)—N(R13)$_2$ or
   6) —($C_0$-$C_4$)-alkylene-Indolyl,
R13 is 1) hydrogen atom,
   2) —($C_1$-$C_4$)-alkyl,
   3) —($C_0$-$C_4$)-alkylene-C(O)—O—R14,
   4) —($C_0$-$C_4$)-alkylene-C(O)—R14 or
   5) —($C_0$-$C_4$)-alkylene-O—R14,
R14 is hydrogen atom, —($C_1$-$C_4$)-alkyl, —$NH_2$ or —OH, and
R15 is hydrogen atom, —($C_1$-$C_4$)-alkyl, —O—$CF_3$, —$NH_2$, —OH, —$CF_3$ or halogen.

The invention also relates to the use of the compound of the formula I where
X is —$S(O)_2$—,
R1 is 1) hydrogen atom or
   2) —($C_1$-$C_4$)-alkyl,
R2 is 1) —($C_1$-$C_6$)-alkylene-$NH_2$,
   2) —($C_1$-$C_4$)-alkylene-pyridyl-$NH_2$,
   3) —($C_1$-$C_4$)-alkylene-piperidinyl-$NH_2$,
   4) —($C_1$-$C_6$)-alkylene-NH—C(=NH)—$NH_2$,
   5) —($C_0$-$C_4$)-alkylene-($C_3$-$C_6$)-cycloalkyl-$NH_2$,
   6) —($C_1$-$C_6$)-alkylene-NH—C(=NH)—($C_1$-$C_4$)-alkyl,
   7) —($C_1$-$C_4$)-alkylene-O—NH—C(=NH)—$NH_2$,
   8) —($C_1$-$C_6$)-alkylene-NH—C(O)—O—($C_1$-$C_4$)-alkylene-phenyl, where phenyl is unsubstituted or substituted by —$NH_2$ or is substituted by —$NH_2$ and once, twice or three times by R15,
   9) —($C_1$-$C_4$)-alkylene-NH—C(O)—($C_1$-$C_6$)-alkyl,
   10) —($C_1$-$C_4$)-alkylene-phenyl, where phenyl is unsubstituted or substituted by —$NH_2$ or is substituted by —$NH_2$ and once, twice or three times by R15, 11) —($C_1$-$C_4$)-alkylene-$SO_2$—($C_1$-$C_4$)-alkylene-$NH_2$ or
12) —($C_1$-$C_4$)-alkylene-S—($C_1$-$C_4$)-alkylene-$NH_2$ R3 is 1) —($C_1$-$C_4$)-alkyl,
   2) —($C_1$-$C_4$)-alkylene-($C_3$-$C_6$)-cycloalkyl,
   3) —($C_1$-$C_4$)-alkylene-phenyl, where phenyl is substituted independently of one another once, twice or three times by R15,
   4) —($C_1$-$C_6$)-alkylene-NH—C(O)—O—($C_1$-$C_4$)-alkylene-phenyl, where phenyl is substituted independently of one another once, twice or three times by R15,
   5) hydrogen atom, R4 is —$N(R6)_2$,
   where R6 are identical or different and are independently of one another
   1) hydrogen atom,
   2) —($C_1$-$C_4$)-alkyl,
   3) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, bicyclo[3.1.1]heptanyl, decahydronaphthalenyl, tetrahydro-naphthalenyl, octahydro-4,7-methanoindenyl and bicyclo[2.2.1]heptanyl and where cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen,
   4) —($C_0$-$C_4$)-alkylene-C(R11)(R12)-($C_3$-$C_{12}$)-cycloalkyl, where cycloalkyl is selected from the group consisting of cyclohexyl, cyclopentyl, cyclobutyl, cyclopropyl, adamantanyl, bicyclo[3.1.1]heptanyl, decahydronaphthalenyl, tetrahydronaphthalenyl, octahydro-4,7-methanoindenyl or bicyclo[2.2.1]heptanyl and in which cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen,
   5) —($C_0$-$C_4$)-alkylene-Het, where Het is selected from the group consisting of acridinyl, azepinyl, azetidinyl, aziridinyl, benzimidazalinyl, benzimidazolyl, benzo[1,3]dioxolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl, where Het or alkylene is unsubstituted or substituted independently of one another once or twice by —($C_1$-$C_4$)-alkyl
   6) —($C_1$-$C_6$)-alkylene-phenyl, where phenyl or alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl,
   7) —($C_0$-$C_4$)-alkylene-C(R11)(R12)-phenyl, where phenyl is unsubstituted or substituted independently of one another once, twice or three times by phenyl or fluorine,
   8) 1,2,3,4-tetrahydronaphthalenyl,
   9) —($C_0$-$C_4$)-alkylene-CH(R11)-C(O)—$NH_2$,
   10) —($C_0$-$C_4$)-alkylene-CH(R11)-C(O)—NH—($C_1$-$C_4$)-alkyl,
   11) —($C_0$-$C_4$)-alkylene-CH(R11)-C(O)—NH—CH(R12)-R13,
   12) —($C_1$-$C_6$)-alkylene-C(O)—O—R11, where alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl,
   13) —($C_0$-$C_4$)-alkylene-C(R11)(R12)-C(O)—O—R11, or
   14) —($C_1$-$C_3$)-fluoroalkyl,
   or the two R6 radicals taken together with the N atom to which they are bonded form a mono- or bicyclic ring selected from the group consisting of pyrrolidine, piperidine, 2-azabicyclo[3.2.2]nonane and 7-azabicyclo[2.2.1]heptane, where the ring is unsubstituted or substituted once or twice by —($C_1$-$C_4$)-alkyl, —C(O)—O—R11, —($C_1$-$C_4$)-alkyl-O—R11 or phenyl, R7 is hydrogen atom or —($C_1$-$C_4$)-alkyl,
R9 is hydrogen atom or —($C_1$-$C_4$)-alkyl,
R11 and R12 are identical or different and are independently of one another
   1) hydrogen atom,
   2) —($C_1$-$C_4$)-alkyl,
   3) —($C_0$-$C_4$)-alkylene-phenyl, where phenyl is unsubstituted or substituted independently of one another once, twice or three times by —OH, halogen or —O—($C_1$-$C_4$)-alkyl,
   4) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, bicyclo[3.1.1]heptanyl, octahydro-4,7-methanoindenyl and bicyclo[2.2.1]heptanyl and where cycloalkyl is unsubstituted or substituted independently of one another once, twice, three or four times by —($C_1$-$C_4$)-alkyl, —C(O)—O—R13 or phenyl, or
   5) —($C_0$-$C_4$)-alkylene-indolyl, R13 is 1) hydrogen atom,
   2) —($C_1$-$C_4$)-alkyl,
   3) —($C_0$-$C_4$)-alkylene-C(O)—O—R14,
   4) —($C_0$-$C_4$)-alkylene-C(O)—R14 or
   5) —($C_0$-$C_4$)-alkylene-O—R14, and R14 is hydrogen atom, —($C_1$-$C_4$)-alkyl, —$NH_2$ or —OH and
R15 is hydrogen atom, —($C_1$-$C_4$)-alkyl, —O—$CF_3$, —$NH_2$, —OH, —$CF_3$ or halogen.

The invention also relates to the use of the compound of the formula I where

X is —S(O)$_2$—,

R1 is 1) hydrogen atom or
2) —(C$_1$-C$_4$)-alkyl,

R2 is 1) —(C$_1$-C$_6$)-alkylene-NH$_2$,
2) —(C$_1$-C$_4$)-alkylene-pyridyl-NH$_2$,
3) —(C$_1$-C$_4$)-alkylene-piperidinyl-NH$_2$,
4) —(C$_1$-C$_4$)-alkylene-NH—C(=NH)—NH$_2$,
5) —(C$_1$-C$_6$)-alkylene-NH—C(=NH)—(C$_1$-C$_4$)-alkyl,
6) —(C$_1$-C$_4$)-alkylene-(C$_3$-C$_6$)-cycloalkyl-NH$_2$,
7) —(C$_1$-C$_4$)-alkylene-O—NH—C(=NH)—NH$_2$,
8) —(C$_1$-C$_6$)-alkylene-NH—C(O)—O—(C$_1$-C$_4$)-alkylene-phenyl,
9) —(C$_1$-C$_4$)-alkylene-NH—C(O)—(C$_1$-C$_6$)-alkyl or
10) —(C$_1$-C$_4$)-alkylene-phenyl-NH$_2$,
11) —(C$_1$-C$_2$)-alkylene-SO$_2$—(C$_1$-C$_4$)-alkylene-NH$_2$ or
12) —(C$_1$-C$_2$)-alkylene-S—(C$_1$-C$_4$)-alkylene-NH$_2$, R3 is 1) —(C$_1$-C$_4$)-alkyl,
2) —(C$_1$-C$_4$)-alkylene-(C$_3$-C$_6$)-cycloalkyl,
3) —(C$_1$-C$_4$)-alkylene-phenyl, where phenyl is unsubstituted or substituted by —OH,
4) —(C$_1$-C$_6$)-alkylene-NH—C(O)—O—(C$_1$-C$_4$)-alkylene-phenyl,
5) hydrogen atom, R4 is —N(R6)$_2$,
where R6 are identical or different and are independently of one another
1) hydrogen atom,
2) —(C$_1$-C$_6$)-alkyl,
3) —(C$_0$-C$_4$)-alkylene-(C$_3$-C$_8$)-cycloalkyl, where cycloalkyl is selected from the group consisting of cyclohexyl, cyclopentyl, cyclopropyl, adamantanyl, 1,7,7-trimethylbicyclo[3.1.1]heptanyl, decahydronaphthalenyl, octahydro-4,7-methanoindenyl and bicyclo[2.2.1]heptanyl and where cycloalkyl is unsubstituted or substituted independently of one another once, twice or three times by —(C$_1$-C$_4$)-alkyl or phenyl,
4) —C(R11)(R12)-adamantanyl,
5) —CH(R11)-C(O)—NH—CH(R12)-R13,
6) —(C$_0$-C$_4$)-alkylene-Het, where Het is selected from the group consisting of benzimidazolyl, isoxazolyl, piperidinyl, pyridyl, pyrrolidinyl, thiophenyl and benzo[1,3]dioxolyl,
7) 1,2,3,4-tetrahydronaphthalenyl,
8) —(C$_0$-C$_4$)-alkylene-C(R11)(R12)-phenyl, where phenyl is unsubstituted or substituted independently of one another once, twice or three times by phenyl or fluorine,
9) —CH(R11)-C(O)—NH$_2$,
10) —CH(R11)-C(O)—NH—CH(R12)-CH$_2$—OH,
11) —(C$_1$-C$_6$)-alkylene-phenyl, where phenyl or alkylene is unsubstituted or substituted independently of one another once or twice by chlorine, fluorine, —C(O)—O—R11, —(C$_1$-C$_4$)-alkyl-O—R11, —O—(C$_1$-C$_4$)-alkyl, phenyl or —(C$_1$-C$_4$)-alkyl,
12) —CH(R11)-C(O)—NH—(C$_1$-C$_4$)-alkyl,
13) —(C$_0$-C$_4$)-alkylene-C(R11)(R12)-bicyclo[3.1.1]heptanyl, where bicyclo[3.1.1]heptanyl is unsubstituted or substituted once to four times by —(C$_1$-C$_4$)-alkyl,
14) —(C$_1$-C$_6$)-alkylene-C(O)—O—R11, where alkylene is unsubstituted or substituted independently of one another once or twice by chlorine, fluorine, C(O)—O—R11, —(C$_1$-C$_4$)-alkyl-O—R11, —O—(C$_1$-C$_4$)-alkyl, phenyl or —(C$_1$-C$_4$)-alkyl,
15) —(C$_0$-C$_4$)-alkylene-C(R11)(R12)-C(O)—O—R11, or
16) —CH$_2$—CF$_2$—CF$_3$, or the two R6 radicals taken together with the N atom to which they are bonded form a mono- or bicyclic ring selected from the group consisting of pyrrolidines, 2-aza-bicyclo[3.2.2]nonane and 7-aza-bicyclo[2.2.1]heptane, where the ring is unsubstituted or substituted once or twice by —(C$_1$-C$_4$)-alkyl, —C(O)—O—R11, —(C$_1$-C$_4$)-alkyl-O—R11 or phenyl, R7 is hydrogen atom or —(C$_1$-C$_4$)-alkyl, R9 is hydrogen atom or —(C$_1$-C$_4$)-alkyl, R11 and R12 are identical or different and are independently of one another
1) hydrogen atom,
2) —(C$_1$-C$_4$)-alkyl,
3) —(C$_0$-C$_4$)-alkylene-phenyl, where phenyl is unsubstituted or substituted independently of one another once, twice or three times by —OH, halogen or —O—(C$_1$-C$_4$)-alkyl,
4) —(C$_0$-C$_4$)-alkylene-(C$_3$-C$_{12}$)-cycloalkyl, where cycloalkyl is selected from the group consisting of cyclohexyl, cyclopentyl, cyclobutyl, cyclopropyl, adamantanyl, 1,7,7-trimethylbicyclo[3.1.1]heptanyl, octahydro-4,7-methano-indenyl and bicyclo[2.2.1]heptanyl and where cycloalkyl is unsubstituted or substituted independently of one another once, twice, three or four times by —(C$_1$-C$_4$)-alkyl, —C(O)—O—R13 or phenyl, or
5) —(C$_0$-C$_4$)-alkylene-Indolyl, R13 is 1) hydrogen atom,
2) —(C$_1$-C$_4$)-alkyl,
3) —(C$_0$-C$_4$)-alkylene-C(O)—O—R14,
4) —(C$_0$-C$_4$)-alkylene-C(O)—R14 or
5) —(C$_0$-C$_4$)-alkylene-O—R14, R14 is hydrogen atom, —(C$_1$-C$_4$)-alkyl, —NH$_2$ or —OH and R15 is hydrogen atom, —(C$_1$-C$_4$)-alkyl, —O—CF$_3$, —NH$_2$, —OH, —CF$_3$ or halogen.

The invention also relates to the use of the compound of the formula I in the context of one or more disorders from the group consisting of myocardial infarction, angina pectoris and other forms of acute coronary syndrome, stroke, peripherally vascular disorders, deep vein thrombosis, pulmonary embolism, embolic or thrombotic events caused by cardiac arrhythmias, cardiovascular events such as restenosis following revascularization and angioplasty and similar procedures such as stent implantations and bypass operations, or reducing the risk of thrombosis following surgical procedures such as operations on the knee and hip, or in the context of disseminated intravascular coagulation, sepsis and other intravascular events associated with inflammation, or atherosclerosis, diabetes and the metabolic syndrome and the sequelae thereof, tumor growth and tumor metastasis, inflammatory and degenerative articular disorders such as rheumatoid arthritis and arthrosis, impairments of the hemostatic system such as fibrin deposits, fibrotic changes of the lung such as chronic obstructive pulmonary disease, adult respiratory distress syndrome or fibrin deposits in the eye following eye operations and prevention or treatment of scarring.

The invention further relates to the compound of the formula I

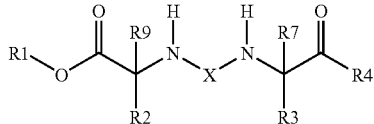

and/or of a stereoisomeric form of the compound of the formula I and/or mixtures of these forms in any ratio, and/or a physiologically tolerated salt of the compound of the formula I, where
X is —S(O)$_2$—,
R1 is 1) hydrogen atom,
2) —(C$_1$-C$_6$)-alkyl,
3) —(C$_0$-C$_4$)-alkylene-(C$_3$-C$_{12}$)-cycloalkyl or
4) —(C$_1$-C$_6$)-alkylene-(C$_6$-C$_{14}$)-aryl,
R2 is a radical of the formula II $$(A1)_m\text{-}A2 \qquad (II)$$

in which
m is the integer zero or 1,
A$^1$ is 1) —(CH$_2$)$_n$— in which n is the integer zero, 1, 2 or 3,
2) —NH—(CH$_2$)$_n$— in which n is the integer zero, 1, 2 or 3,
3) —NH(C$_1$-C$_6$)-alkyl)-(CH$_2$)$_n$— in which n is the integer zero, 1, 2 or 3,
4) —NH((C$_3$-C$_6$)-cycloalkyl)-(CH$_2$)$_n$— in which n is the integer zero, 1, 2 or 3,
5) —O—(CH$_2$)$_n$— in which n is the integer zero, 1, 2 or 3, or
6) —(CH$_2$)n-SO$_n$— in which n is the integer zero 1, 2 or 3 and x is the integer zero, 1 or 2
A2 is 1) Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, and is unsubstituted or substituted independently of one another once, twice or three times by —(C$_1$-C$_3$)-alkyl, halogen, —NH$_2$, —CF$_3$ or —O—CF$_3$,
2) —(C$_0$-C$_6$)-alkylene-NH$_2$,
3) —(C$_1$-C$_6$)-alkylene-NH—C(=NH)—NH$_2$,
4) —(C$_1$-C$_6$)-alkylene-NH—C(=NH)—(C$_1$-C$_4$)-alkyl,
5) —(C$_0$-C$_4$)-alkylene-O—NH—C(=NH)—NH$_2$,
6) —(C$_0$-C$_4$)-alkylene-NH—C(O)—(C$_1$-C$_6$)-alkyl,
7) —(C$_1$-C$_6$)-alkylene-NH—C(O)—O—(C$_1$-C$_4$)-alkylene-(C6-C14)-aryl, where aryl is unsubstituted or substituted by —NH$_2$ or is substituted by —NH$_2$ and once, twice or three times by R15,
8) —(C$_3$-C$_8$)-cycloalkyl-NH$_2$, or
9) —(C$_0$-C$_4$)-alkylene-(C$_6$-C$_{14}$)-aryl, where aryl is unsubstituted or substituted by —NH$_2$ or is substituted by —NH$_2$ and once, twice or three times by R15,
R3 is 1) —(C$_1$-C$_6$)-alkyl,
2) —(C$_0$-C$_4$)-alkylene-(C$_3$-C$_{12}$)-cycloalkyl,
3) —(C$_1$-C$_6$)-alkylene-(C$_6$-C$_{14}$)-aryl, where aryl is substituted independently of one another once, twice or three times by R15,
4) —(C$_0$-C$_8$)-alkylene-N(R5)-PG1,
5) —(C$_1$-C$_6$)-alkylene-NH—C(O)—O—(C$_1$-C$_4$)-alkylene-(C6-C14)-aryl, where aryl is substituted independently of one another once, twice or three times by R15,
6) —(C$_0$-C$_4$)-alkylene-(C$_6$-C$_{14}$)-aryl-(C$_0$-C$_4$)-alkylene-N(R5)-PG1,
7) —(C$_0$-C$_8$)-alkylene-O-PG2,
8) —(C$_0$-C$_4$)-alkylene-(C$_6$-C$_{14}$)-aryl-(C$_0$-C$_4$)-alkylene-O-PG2,
9) —(C$_0$-C$_8$)-alkylene-C(O)—O-PG3,
10) —(C$_0$-C$_4$)-alkylene-(C$_6$-C$_{14}$)-aryl-(C$_0$-C$_4$)-alkylene-C(O)—O-PG3 or
11) hydrogen atom,
R4 is —N(R6)$_2$,
where R6 are identical or different and are independently of one another
1) hydrogen atom,
2) —(C$_1$-C$_6$)-alkyl,
3) —(C$_0$-C$_4$)-alkylene-(C$_3$-C$_{12}$)-cycloalkyl, where cycloalkyl is unsubstituted or substituted independently of one another once, twice, three or four times by R11, halogen, —C(O)—O—R11, —(C$_1$-C$_4$)-alkyl-O—R11 or —O—(C$_1$-C$_4$)-alkyl,
4) —(C$_0$-C$_6$)-alkylene-(C$_6$-C$_{14}$)-aryl, where aryl and alkylene are unsubstituted or substituted independently of one another once, twice, three or four times by R11, halogen, —C(O)—O—R11, —(C$_1$-C$_4$)-alkyl-O—R11, —C(O)—N(R8)$_2$ or —O—(C$_1$-C$_4$)-alkyl,
5) —(C$_0$-C$_8$)-alkylene-N(R5)-PG1,
6) —(C$_0$-C$_4$)-alkylene-(C$_6$-C$_{14}$)-aryl-(C$_0$-C$_4$)-alkyl-N(R5)-PG1,
7) —(C$_0$-C$_8$)-alkylene-O-PG2,
8) —(C$_0$-C$_4$)-alkylene-(C$_6$-C$_{14}$)-aryl-(C$_0$-C$_4$)-alkyl-O-PG2,
9) —(C$_0$-C$_8$)-alkylene-C(O)—O—R11,
10) —(C$_0$-C$_4$)-alkylene-(C$_6$-C$_{14}$)-aryl-(C$_0$-C$_4$)-alkyl-C(O)—O-PG3,
11) —(C$_0$-C$_4$)-alkylene-Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —(C$_1$-C$_4$)-alkyl-O—R11 or —O—(C$_1$-C$_4$)-alkyl,
12) —(C$_1$-C$_3$)-fluoroalkyl,
13) —(C$_0$-C$_4$)-alkylene-CH(R11)-C(O)—NH$_2$,
14) —(C$_0$-C$_4$)-alkylene-CH(R11)-C(O)—NH—(C$_1$-C$_4$)-alkyl,
15) —(C$_0$-C$_4$)-alkylene-CH(R11)-C(O)—NH—CH(R12)-R13, or
16) amino acid, where the linkage of the amino acid takes place by a peptide linkage, and the carboxyl radical of the amino acid is unsubstituted or substituted by PG3 or by —N(R5)$_2$,
or the two R6 radicals form together with the N atom to which they are bonded a mono- or bicyclic ring having 4 to 9 ring atoms which is saturated, partly saturated or aromatic, where the ring is unsubstituted or substituted once or twice by —(C$_1$-C$_4$)-alkyl, —C(O)—O—R11, halogen, —(C$_1$-C$_4$)-alkyl-O—R11 or phenyl,
R5 is hydrogen atom or —(C$_1$-C$_6$)-alkyl,
PG1 is a protective group for the amino function,
PG2 is a protective group for the hydroxy function,
PG3 is a protective group for the carboxyl function,
R7 is hydrogen atom or —(C$_1$-C$_6$)-alkyl,
R8 is hydrogen atom or —(C$_1$-C$_6$)-alkyl,
R9 is hydrogen atom or —(C$_1$-C$_6$)-alkyl, R11 and R12 are identical or different and are independently of one another
1) hydrogen atom,
2) —($C_1$-$C_6$)-alkyl,
3) —($C_0$-$C_4$)-alkylene-phenyl, where phenyl is unsubstituted or substituted independently of one another once, twice or three times by halogen, —OH or —O—($C_1$-$C_4$)-alkyl,
4) —($C_0$-$C_4$)-alkylene-($C_3$-$C_{12}$)-cycloalkyl, where cycloalkyl is unsubstituted or substituted independently of one another once, twice, three or four times by R13, halogen, —C(O)—O—R13, —($C_1$-$C_4$)-alkyl-O—R13, —O—($C_1$-$C_4$)-alkyl or —($C_0$-$C_4$)-alkylene-phenyl,
5) —($C_0$-$C_4$)-alkylene-C(O)—N(R13)$_2$ or
6) —($C_0$-$C_4$)-alkylene-indolyl, R13 is 1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14, R14 is hydrogen atom, —($C_1$-$C_4$)-alkyl, —NH$_2$ or —OH, and R15 is hydrogen atom, —($C_1$-$C_4$)-alkyl, —O—CF$_3$, —NH$_2$, —OH, —CF$_3$ or halogen.

The invention further relates the compound of the formula I where
X is —S(O)$_2$—,
R1 is 1) hydrogen atom or
2) —($C_1$-$C_4$)-alkyl,
R2 is 1) —($C_1$-$C_6$)-alkylene-NH$_2$,
2) —($C_0$-$C_4$)-alkylene-pyridyl-NH$_2$,
3) —($C_0$-$C_4$)-alkylene-piperidinyl-NH$_2$,
4) —($C_0$-$C_4$)-alkylene-thiazolyl-NH$_2$,
5) —($C_1$-$C_6$)-alkylene-NH—C(=NH)—NH$_2$,
6) —($C_0$-$C_4$)-alkylene-($C_3$-$C_8$)-cycloalkyl-NH$_2$,
7) —($C_1$-$C_6$)-alkylene-NH—C(=NH)—($C_1$-$C_4$)-alkyl,
8) —($C_0$-$C_4$)-alkylene-O—NH—C(=NH)—NH$_2$,
9) —($C_1$-$C_6$)-alkylene-NH—C(O)—O—($C_1$-$C_4$)-alkylene-(C6-C14)-aryl, where aryl is unsubstituted or substituted by —NH$_2$ or is substituted by —NH$_2$ and once, twice or three times by R15,
10) —($C_0$-$C_4$)-alkylene-NH—C(O)—($C_1$-$C_4$)-alkyl
11) —($C_0$-$C_4$)-alkylene-($C_6$-$C_{14}$)-aryl, where aryl is unsubstituted or substituted by —NH$_2$ and once, twice or three times by R15, or
12) —($C_1$-$C_4$)-alkylene-SO$_x$—($C_1$-$C_4$)-alkylene-NH$_2$ in which x is the integer zero, 1 or 2

R3 is 1) —($C_1$-$C_4$)-alkyl,
2) —($C_0$-$C_4$)-alkylene-($C_3$-$C_8$)-cycloalkyl,
3) —($C_1$-$C_6$)-alkylene-(C6-C14)-aryl, where aryl is substituted independently of one another once, twice or three times by R15,
4) —($C_1$-$C_6$)-alkylene-NH—C(O)—O—($C_1$-$C_4$)-alkylene-(C6-C14)-aryl, where aryl is substituted independently of one another once, twice or three times by R15,
5) —($C_1$-$C_6$)-alkylene-NH-PG1,
6) —($C_1$-$C_6$)-alkylene-O-PG2,
7) —($C_1$-$C_6$)-alkyl, or
8) hydrogen atom,
where PG1 is t-butyloxycarbonyl or benzyloxycarbonyl, and PG2 is t-butyl-, t-butyloxycarbonyl or benzyloxycarbonyl, R4 is —N(R6)$_2$,
where R6 are identical or different and are independently of one another
1) hydrogen atom,
2) —($C_1$-$C_6$)-alkyl,
3) —($C_0$-$C_4$)-alkylene-($C_3$-$C_{12}$)-cycloalkyl, where cycloalkyl is unsubstituted or substituted independently of one another once, twice, three or four times by R11, halogen, —C(O)—O—R11, —($C_1$-$C_4$)-alkyl-O—R11 or —O—($C_1$-$C_4$)-alkyl,
4) —($C_0$-$C_4$)-alkylene-C(R11)(R12)-($C_3$-$C_{12}$)-cycloalkyl, where cycloalkyl is unsubstituted or substituted independently of one another once, twice or three times by R11, halogen, —C(O)—O—R11, —($C_1$-$C_4$)-alkyl-O—R11 or —O—($C_1$-$C_4$)-alkyl,
5) —($C_0$-$C_4$)-alkylene-Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —($C_1$-$C_4$)-alkyl-O—R11 or —O—($C_1$-$C_4$)-alkyl,
6) —($C_0$-$C_6$)-alkylene-(C6-C14)-aryl, where aryl or alkylene is unsubstituted or substituted independently of one another once, twice or three times by R11, halogen, —C(O)—O—R11, —($C_0$-$C_4$)-alkyl-O—R11 or —O—($C_1$-$C_4$)-alkyl,
7) —($C_0$-$C_4$)-alkylene-C(R11)(R12)-aryl, where aryl or alkylene is unsubstituted or substituted independently of one another once, twice or three times by R11, halogen, —C(O)—O—R11, —($C_0$-$C_4$)-alkyl-O—R11 or —O—($C_1$-$C_4$)-alkyl,
8) 1,2,3,4-tetrahydronaphthalenyl,
9) —($C_0$-$C_4$)-alkylene-CH(R11)-C(O)—NH$_2$,
10) —($C_0$-$C_4$)-alkylene-CH(R11)-C(O)—NH—($C_1$-$C_4$)-alkyl,
11) —($C_0$-$C_4$)-alkylene-CH(R11)-C(O)—NH—CH(R12)-R13,
12) —($C_0$-$C_6$)-alkylene-C(O)—O—R11, where alkylene is unsubstituted or substituted independently of one another once or twice by R11, halogen, —C(O)—O—R11, —($C_1$-$C_4$)-alkyl-O—R11 or —O—($C_1$-$C_4$)-alkyl,
13) —($C_0$-$C_4$)-alkylene-C(R11)(R12)-C(O)—O—R11, or
14) —($C_1$-$C_3$)-fluoroalkyl,
or the two R6 radicals form together with the N atom to which they are bonded a mono- or bicyclic ring having 4 to 9 ring atoms which is saturated, partly saturated or aromatic, where the ring is unsubstituted or substituted once or twice by —($C_1$-$C_4$)-alkyl, —C(O)—O—R11, halogen, —($C_1$-$C_4$)-alkyl-O—R11 or phenyl, R7 is hydrogen atom or —($C_1$-$C_4$)-alkyl,
R9 is hydrogen atom or —($C_1$-$C_4$)-alkyl,
R11 and R12 are identical or different and are independently of one another
1) hydrogen atom,
2) —($C_1$-$C_4$)-alkyl,
3) —($C_0$-$C_4$)-alkylene-phenyl, where phenyl is unsubstituted or substituted independently of one another once, twice or three times by halogen, —OH or —O—($C_1$-$C_4$)-alkyl,
4) —($C_0$-$C_4$)-alkylene-($C_3$-$C_{12}$)-cycloalkyl, where cycloalkyl is unsubstituted or substituted independently of one another once, twice, three or four times by R13, halogen, —C(O)—O—R13, —($C_1$-$C_4$)-alkyl-O—R13, —O—($C_1$-$C_4$)-alkyl or —($C_0$-$C_4$)-alkylene-phenyl,
5) —($C_0$-$C_4$)-alkylene-C(O)—N(R13)$_2$ or
6) —($C_0$-$C_4$)-alkylene-indolyl, R13 is 1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-C—R14, R14 is hydrogen atom, —($C_1$-$C_4$)-alkyl, —$NH_2$ or —OH, and R15 is hydrogen atom, —($C_1$-$C_4$)-alkyl, —O—$CF_3$, —$NH_2$, —OH, —$CF_3$ or halogen.

The invention also relates to the use of the compound of the formula I where

X is —S(O)$_2$—,

R1 is 1) hydrogen atom or
2) —($C_1$-$C_4$)-alkyl,

R2 is 1) —($C_1$-$C_6$)-alkylene-$NH_2$,
2) —($C_1$-$C_4$)-alkylene-pyridyl-$NH_2$,
3) —($C_1$-$C_4$)-alkylene-piperidinyl-$NH_2$,
4) —($C_1$-$C_6$)-alkylene-NH—C(=NH)—$NH_2$,
5) —($C_0$-$C_4$)-alkylene-($C_3$-$C_6$)-cycloalkyl-$NH_2$,
6) —($C_1$-$C_6$)-alkylene-NH—C(=NH)—($C_1$-$C_4$)-alkyl,
7) —($C_1$-$C_4$)-alkylene-O—NH—C(=NH)—$NH_2$,
8) —($C_1$-$C_6$)-alkylene-NH—C(O)—O—($C_1$-$C_4$)-alkylene-phenyl, where phenyl is unsubstituted or substituted by —$NH_2$ or is substituted by —$NH_2$ and once, twice or three times by R15,
9) —($C_1$-$C_4$)-alkylene-NH—C(O)—($C_1$-$C_6$)-alkyl,
10) —($C_1$-$C_4$)-alkylene-phenyl, where phenyl is unsubstituted or substituted by —$NH_2$ or is substituted by —$NH_2$ and once, twice or three times by R15,
11) —($C_1$-$C_4$)-alkylene-$SO_2$—($C_1$-$C_4$)-alkylene-$NH_2$ or
12) —($C_1$-$C_4$)-alkylene-S—($C_1$-$C_4$)-alkylene-$NH_2$, R3 is 1) —($C_1$-$C_4$)-alkyl,
2) —($C_1$-$C_4$)-alkylene-($C_3$-$C_6$)-cycloalkyl,
3) —($C_1$-$C_4$)-alkylene-phenyl, where phenyl is substituted independently of one another once, twice or three times by R15,
4) —($C_1$-$C_6$)-alkylene-NH—C(O)—O—($C_1$-$C_4$)-alkylene-phenyl, where phenyl is substituted independently of one another once, twice or three times by R15,
5) hydrogen atom, R4 is —N(R6)$_2$,
where R6 are identical or different and are independently of one another
1) hydrogen atom,
2) —($C_1$-$C_4$)-alkyl,
3) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, decahydronaphthalenyl, tetrahydronaphthalenyl, octahydro-4,7-methanoindenyl and bicyclo[2.2.1]heptanyl, and in which cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen, or 1,7,7-trimethylbicyclo[3.1.1]heptanyl which is unsubstituted or substituted by —($C_1$-$C_4$)-alkyl, —C(O)—O—R11 or —($C_1$-$C_4$)-alkylene-phenyl, where phenyl is unsubstituted or substituted by halogen
4) —($C_0$-$C_4$)-alkylene-C(R11)(R12)-($C_3$-$C_{12}$)-cycloalkyl, where cycloalkyl is selected from the group consisting of cyclohexyl, cyclopentyl, cyclobutyl, cyclopropyl, adamantanyl, decahydronaphthalenyl, tetrahydronaphthalenyl, octahydro-4,7-methanoindenyl and bicyclo[2.2.1]heptanyl, and in which cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen, or 1,7,7-trimethylbicyclo[3.1.1]heptanyl, which is unsubstituted or substituted by —($C_1$-$C_4$)-alkyl, —C(O)—O—R11 or —($C_1$-$C_4$)-alkylene-phenyl, where phenyl is unsubstituted or substituted by halogen 5) —($C_0$-$C_4$)-alkylene-Het, where Het is selected from the group consisting of acridinyl, azepinyl, azetidinyl, aziridinyl, benzimidazalinyl, benzimidazolyl, benzo[1,3]dioxolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl, where Het or alkylene is unsubstituted or substituted independently of one another once or twice by —($C_1$-$C_4$)-alkyl,
6) —($C_1$-$C_6$)-alkylene-phenyl, where phenyl or alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl,
7) —($C_0$-$C_4$)-alkylene-C(R11)(R12)-phenyl, where phenyl is unsubstituted or substituted independently of one another once, twice or three times by phenyl or fluorine,
8) 1,2,3,4-tetrahydronaphthalenyl,
9) —($C_0$-$C_4$)-alkylene-CH(R11)-C(O)—$NH_2$,
10) —($C_0$-$C_4$)-alkylene-CH(R11)-C(O)—NH—($C_1$-$C_4$)-alkyl,
11) —($C_0$-$C_4$)-alkylene-CH(R11)-C(O)—NH—CH(R12)-R13,
12) —($C_1$-$C_6$)-alkylene-C(O)—O—R11, where alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl,
13) —($C_0$-$C_4$)-alkylene-C(R11)(R12)-C(O)—O—R11, or 14) —($C_1$-$C_3$)-fluoroalkyl,
or the two R6 radicals form together with the N atom to which they are bonded a mono- or bicyclic ring selected from the group consisting of pyrrolidine, piperidine, 2-aza-bicyclo[3.2.2]nonane and 7-aza-bicyclo[2.2.1] heptane, where the ring is unsubstituted or substituted once or twice by —($C_1$-$C_4$)-alkyl, —C(O)—O—R11, —($C_1$-$C_4$)-alkyl-O—R11 or phenyl, R7 is hydrogen atom or —($C_1$-$C_4$)-alkyl,
R9 is hydrogen atom or —($C_1$-$C_4$)-alkyl,
R11 and R12 are identical or different and are independently of one another
1) hydrogen atom,
2) —($C_1$-$C_4$)-alkyl,
3) —($C_0$-$C_4$)-alkylene-phenyl, where phenyl is unsubstituted or substituted independently of one another once, twice or three times by —OH, halogen or —O—($C_1$-$C_4$)-alkyl,
4) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, 1,7,7-trimethylbicyclo[3.1.1]heptanyl, decahydronaphthalenyl, tetrahydronaphthalenyl, octahydro-4,7-methanoindenyl or bicyclo[2.2.1]heptanyl and in which cycloalkyl is unsubstituted or substituted independently of one another once, twice, three or four times by —($C_1$-$C_4$)-alkyl, —C(O)—O—R13 or phenyl, or
5) —($C_0$-$C_4$)-alkylene-indolyl,
R13 is 1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14, and
R14 is hydrogen atom, —($C_1$-$C_4$)-alkyl, —$NH_2$ or —OH and
R15 is hydrogen atom, —($C_1$-$C_4$)-alkyl, —O—$CF_3$, —$NH_2$, —OH, —$CF_3$ or halogen.

The invention also relates to the use of the compound of the formula I where
X is —S(O)$_2$—,
R1 is 1) hydrogen atom or
2) —($C_1$-$C_4$)-alkyl,
R2 is 1) —($C_1$-$C_6$)-alkylene-$NH_2$,
2) —($C_1$-$C_4$)-alkylene-pyridyl-$NH_2$,
3) —($C_1$-$C_4$)-alkylene-piperidinyl-$NH_2$,
4) —($C_1$-$C_4$)-alkylene-NH—C(=NH)—$NH_2$,
5) —($C_1$-$C_6$)-alkylene-NH—C(=NH)—($C_1$-$C_4$)-alkyl,
6) —($C_1$-$C_4$)-alkylene-($C_3$-$C_6$)-cycloalkyl-$NH_2$,
7) —($C_1$-$C_4$)-alkylene-O—NH—C(=NH)—$NH_2$,
8) —($C_1$-$C_6$)-alkylene-NH—C(O)—O—($C_1$-$C_4$)-alkylene-phenyl,
9) —($C_1$-$C_4$)-alkylene-NH—C(O)—($C_1$-$C_6$)-alkyl,
10) —($C_1$-$C_4$)-alkylene-phenyl-$NH_2$,
11) —($C_1$-$C_2$)-alkylene-$SO_2$—($C_1$-$C_4$)-alkylene-$NH_2$ or
12) —($C_1$-$C_2$)-alkylene-S—($C_1$-$C_4$)-alkylene-$NH_2$,
R3 is 1) —($C_1$-$C_4$)-alkyl,
2) —($C_1$-$C_4$)-alkylene-($C_3$-$C_6$)-cycloalkyl,
3) —($C_1$-$C_4$)-alkylene-phenyl, where phenyl is unsubstituted or substituted by —OH,
4) —($C_1$-$C_6$)-alkylene-NH—C(O)—O—($C_1$-$C_4$)-alkylene-phenyl,
5) hydrogen atom,
R4 is —N(R6)$_2$,
where R6 are identical or different and are independently of one another
1) hydrogen atom,
2) —($C_1$-$C_6$)-alkyl,
3) —($C_0$-$C_4$)-alkylene-($C_3$-$C_8$)-cycloalkyl, where cycloalkyl is selected from the group consisting of cyclohexyl, cyclopentyl, cyclopropyl, adamantanyl, 1,7,7-trimethylbicyclo[3.1.1]heptanyl, decahydronaphthalene, octahydro-4,7-methanoindenyl or bicyclo[2.2.1] heptanyl and in which cycloalkyl is unsubstituted or substituted independently of one another once, twice or three times by —($C_1$-$C_4$)-alkyl or phenyl,
4) —C(R11)(R12)-adamantanyl,
5) —CH(R11)-C(O)—NH—CH(R12)—R13,
6) —($C_0$-$C_4$)-alkylene-Het, where Het is selected from the group consisting of benzimidazolyl, isoxazolyl, piperidine, pyridine, pyrrolidinyl, thiophenyl and benzo[1,3]dioxol,
7) 1,2,3,4-tetrahydronaphthalenyl,
8) —($C_0$-$C_4$)-alkylene-C(R11)(R12)-phenyl, where phenyl is unsubstituted or substituted independently of one another once, twice or three times by phenyl or fluorine,
9) —CH(R11)-C(O)—$NH_2$,
10) —CH(R11)-C(O)—NH—CH(R12)-$CH_2$—OH,
11) —($C_1$-$C_6$)-alkylene-phenyl, where phenyl or alkylene is unsubstituted or substituted independently of one another once or twice by chlorine, fluorine, —C(O)—O—R11, —($C_1$-$C_4$)-alkyl-O—R11, —O—($C_1$-$C_4$)-alkyl, phenyl or —($C_1$-$C_4$)-alkyl,
12) —CH(R11)-C(O)—NH—($C_1$-$C_4$)-alkyl,
13) —($C_0$-$C_4$)-alkylene-C(R11)(R12)-bicyclo[3.1.1]heptanyl, where bicyclo[3.1.1]heptanyl is unsubstituted or substituted once to four times by —($C_1$-$C_4$)-alkyl,
14) —($C_1$-$C_6$)-alkylene-C(O)—O—R11, where alkylene is unsubstituted or substituted independently of one another once or twice by chlorine, fluorine, —C(O)—O—R11, —($C_1$-$C_4$)-alkyl-O—R11, —O—($C_1$-$C_4$)-alkyl, phenyl or —($C_1$-$C_4$)-alkyl,
15) —($C_0$-$C_4$)-alkylene-C(R11)(R12)-C(O)—O—R11, or
16) —$CH_2$—$CF_2$—$CF_3$,
or the two R6 radicals form together with the N atom to which they are bonded a mono- or bicyclic ring selected from the group consisting of pyrrolidines, 2-azabicyclo[3.2.2]nonane and 7-aza-bicyclo[2.2.1]heptane, where the ring is unsubstituted or substituted once or twice by —($C_1$-$C_4$)-alkyl, —C(O)—O—R11, —($C_1$-$C_4$)-alkyl-O—R11 or phenyl,
R7 is hydrogen atom or —($C_1$-$C_4$)-alkyl,
R9 is hydrogen atom or —($C_1$-$C_4$)-alkyl,
R11 and R12 are identical or different and are independently of one another
1) hydrogen atom,
2) —($C_1$-$C_4$)-alkyl,
3) —($C_0$-$C_4$)-alkylene-phenyl, where phenyl is unsubstituted or substituted independently of one another once, twice or three times by —OH, halogen or O—($C_1$-$C_4$)-alkyl,
4) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, 1,7,7-trimethylbicyclo[3.1.1]heptanyl, decahydronaphthalenyl, octahydro-4,7-methanoindenyl or bicyclo[2.2.1]heptanyl and in which cycloalkyl is unsubstituted or substituted independently of one another once, twice, three or four times by —($C_1$-$C_4$)-alkyl, —C(O)—O—R13 or phenyl or
5) —($C_0$-$C_4$)-alkylene-indolyl,
R13 is 1) hydrogen atom,
2) —($C_1$-$C_4$)-alkyl,
3) —($C_0$-$C_4$)-alkylene-C(O)—O—R14, 4) —(C$_0$-C$_4$)-alkylene-C(O)—R14 or
5) —(C$_0$-C$_4$)-alkylene-O—R14,
R14 is hydrogen atom, —(C$_1$-C$_4$)-alkyl, —NH$_2$ or —OH and
R15 is hydrogen atom, —(C$_1$-C$_4$)-alkyl, —O—CF$_3$, —NH$_2$, —OH, —CF$_3$ or halogen.

The invention also relates to the compound of the formula I and/or of a stereoisomeric form of the compound of the formula I and/or mixtures of these forms in any ratio, and/or a physiologically tolerated salt of the compound of the formula I, where X is —C(O)—,
R1 is 1) hydrogen atom,
  2) —(C$_1$-C$_6$)-alkyl,
  3) —(C$_0$-C$_4$)-alkylene-(C$_3$-C$_{12}$)-cycloalkyl or
  4) —(C$_1$-C$_6$)-alkylene-(C$_6$-C$_{14}$)-aryl,
R2 is the radical of the formula II $$-(A1)_m\text{-}A2 \qquad (II)$$

in which
m is the integer zero or 1,
A$^1$ is 1) —(CH$_2$)$_n$— in which n is the integer zero, 1, 2 or 3,
  2) —NH—(CH$_2$)$_n$— in which n is the integer zero, 1, 2 or 3,
  3) —NH(C$_1$-C$_6$)-alkyl)-(CH$_2$)$_n$— in which n is the integer zero, 1, 2 or 3,
  4) —NH((C$_3$-C$_6$)-cycloalkyl)-(CH$_2$)$_n$— in which n is the integer zero, 1, 2 or 3,
  5) —O—(CH$_2$)$_n$— in which n is the integer zero, 1, 2 or 3, or
  6) —(CH$_2$)$_n$—SO$_x$— in which n is the integer zero, 1, 2 or 3 and x is the integer zero, 1 or 2,
A2 is 1) Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, and is unsubstituted or substituted independently of one another once, twice or three times by —(C$_1$-C$_3$)-alkyl, halogen, —NH$_2$, —CF$_3$ or —O—CF$_3$,
  2) —(C$_0$-C$_6$)-alkylene-NH$_2$,
  3) —(C$_1$-C$_6$)-alkylene-NH—C(=NH)—NH$_2$,
  4) —(C$_1$-C$_6$)-alkylene-NH—C(=NH)—(C$_1$-C$_4$)-alkyl,
  5) —(C$_0$-C$_4$)-alkylene-O—NH—C(=NH)—NH$_2$,
  6) —(C$_0$-C$_4$)-alkylene-NH—C(O)—(C$_1$-C$_4$)-alkyl,
  7) —(C$_1$-C$_6$)-alkylene-NH—C(O)—O—(C$_1$-C$_4$)-alkylene-(C6-C14)-aryl, where aryl is unsubstituted or substituted by —NH$_2$ or is substituted by —NH$_2$ and once, twice or three times by R15,
  8) —(C$_3$-C$_8$)-cycloalkyl-NH$_2$, or
  9) —(C$_0$-C$_4$)-alkylene-(C$_6$-C$_{14}$)-aryl, where aryl is unsubstituted or substituted by —NH$_2$ or is substituted by —NH$_2$ and once, twice or three times by R15,
R3 is 1) —(C$_1$-C$_6$)-alkyl,
  2) —(C$_0$-C$_4$)-alkylene-(C$_3$-C$_{12}$)-cycloalkyl,
  3) —(C$_1$-C$_6$)-alkylene-(C$_6$-C$_{14}$)-aryl, where aryl is substituted independently of one another once, twice or three times by R15,
  4) —(C$_0$-C$_8$)-alkylene-N(R5)-PG1,
  5) —(C$_1$-C$_6$)-alkylene-NH—C(O)—O—(C$_1$-C$_4$)-alkylene-(C6-C14)-aryl, where aryl is substituted independently of one another once, twice or three times by R15,
  6) —(C$_0$-C$_4$)-alkylene-(C$_6$-C$_{14}$)-aryl-(C$_0$-C$_4$)-alkylene-N(R5)-PG1,
  7) —(C$_0$-C$_8$)-alkylene-O-PG2,
  8) —(C$_0$-C$_4$)-alkylene-(C$_6$-C$_{14}$)-aryl-(C$_0$-C$_4$)-alkylene-O-PG2,
  9) —(C$_0$-C$_8$)-alkylene-C(O)—O-PG3,
  10) —(C$_0$-C$_4$)-alkylene-(C$_6$-C$_{14}$)-aryl-(C$_0$-C$_4$)-alkylene-C(O)—O-PG3 or
  11) hydrogen atom,
R4 is —N(R6)$_2$,
where R6 are identical or different and are independently of one another
  1) hydrogen atom,
  2) —(C$_1$-C$_6$)-alkyl,
  3) —(C$_0$-C$_4$)-alkylene-(C$_3$-C$_{12}$)-cycloalkyl, where cycloalkyl is unsubstituted or substituted independently of one another once, twice, three or four times by R11, halogen, —C(O)—O—R11, —(C$_1$-C$_4$)-alkyl-O—R11 or —O—(C$_1$-C$_4$)-alkyl,
  4) —(C$_0$-C$_6$)-alkylene-(C$_6$-C$_{14}$)-aryl, where aryl and alkylene are unsubstituted or substituted independently of one another once, twice, three or four times by R11, halogen, —C(O)—O—R11, —(C$_1$-C$_4$)-alkyl-O—R11, —C(O)—N(R8)$_2$ or —O—(C$_1$-C$_4$)-alkyl,
  5) —(C$_0$-C$_8$)-alkylene-N(R5)-PG1,
  6) —(C$_0$-C$_4$)-alkylene-(C$_6$-C$_{14}$)-aryl-(C$_0$-C$_4$)-alkyl-N(R5)-PG1,
  7) —(C$_0$-C$_8$)-alkylene-O-PG2,
  8) —(C$_0$-C$_4$)-alkylene-(C$_6$-C$_{14}$)-aryl-(C$_0$-C$_4$)-alkyl-O-PG2,
  9) —(C$_0$-C$_8$)-alkylene-C(O)—O—R11,
  10) —(C$_0$-C$_4$)-alkylene-(C$_6$-C$_{14}$)-aryl-(C$_0$-C$_4$)-alkyl-C(O)—O-PG3,
  11) —(C$_0$-C$_4$)-alkylene-Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —(C$_1$-C$_4$)-alkyl-O—R11 or —O—(C$_1$-C$_4$)-alkyl,
  12) —(C$_1$-C$_3$)-fluoroalkyl,
  13) —(C$_0$-C$_4$)-alkylene-CH(R11)-C(O)—NH$_2$,
  14) —(C$_0$-C$_4$)-alkylene-CH(R11)-C(O)—NH—(C$_1$-C$_4$)-alkyl,
  15) —(C$_0$-C$_4$)-alkylene-CH(R11)-C(O)—NH—CH(R12)-R13, or
  16) amino acid, where the linkage of the amino acid takes place by a peptide linkage, and the carboxyl radical of the amino acid is unsubstituted or substituted by PG3 or by —N(R5)$_2$,
or the two R6 radicals form together with the N atom to which they are bonded a mono- or bicyclic ring having 4 to 9 ring atoms which is saturated, partly saturated or aromatic, where the ring is unsubstituted or substituted once or twice by —(C$_1$-C$_4$)-alkyl, —C(O)—O—R11, halogen, —(C$_1$-C$_4$)-alkyl-O—R11 or phenyl,
R5 is hydrogen atom or —(C$_1$-C$_6$)-alkyl,
PG1 is a protective group for the amino function,
PG2 is a protective group for the hydroxy function,
PG3 is a protective group for the carboxyl function,
R7 is hydrogen atom or —(C$_1$-C$_6$)-alkyl,
R8 is hydrogen atom or —(C$_1$-C$_6$)-alkyl,
R9 is hydrogen atom or —(C$_1$-C$_6$)-alkyl,
R11 and R12 are identical or different and are independently of one another
  1) hydrogen atom,
  2) —(C$_1$-C$_6$)-alkyl, 3) —($C_0$-$C_4$)-alkylene-phenyl, where phenyl is unsubstituted or substituted independently of one another once, twice or three times by halogen, —OH or —O—($C_1$-$C_4$)-alkyl,
4) —($C_0$-$C_4$)-alkylene-($C_3$-$C_{12}$)-cycloalkyl, where cycloalkyl is unsubstituted or substituted independently of one another once, twice, three or four times by R13, halogen, —C(O)—O—R13, —($C_1$-$C_4$)-alkyl-O—R13, —O—($C_1$-$C_4$)-alkyl or —($C_0$-$C_4$)-alkylene-phenyl,
5) —($C_0$-$C_4$)-alkylene-C(O)—N(R13)$_2$ or
6) —($C_0$-$C_4$)-alkylene-indolyl, R13 is 1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14, R14 is hydrogen atom, —($C_1$-$C_4$)-alkyl, —NH$_2$ or —OH, and R15 is hydrogen atom, —($C_1$-$C_4$)-alkyl, —O—CF$_3$, —NH$_2$, —OH, —CF$_3$ or halogen.

The invention also relates to the compound of the formula I where
X is —C(O)—,
R1 is 1) hydrogen atom or
2) —($C_1$-$C_4$)-alkyl,
R2 is 1) —($C_1$-$C_6$)-alkylene-NH$_2$,
2) —($C_0$-$C_4$)-alkylene-pyridyl-NH$_2$,
3) —($C_0$-$C_4$)-alkylene-piperidinyl-NH$_2$,
4) —($C_0$-$C_4$)-alkylene-thiazolyl-NH$_2$,
5) —($C_1$-$C_6$)-alkylene-NH—C(=NH)—NH$_2$,
6) —($C_0$-$C_4$)-alkylene-($C_3$-$C_8$)-cycloalkyl-NH$_2$,
7) —($C_1$-$C_6$)-alkylene-NH—C(=NH)—($C_1$-$C_4$)-alkyl,
8) —($C_0$-$C_4$)-alkylene-O—NH—C(=NH)—NH$_2$,
9) —($C_1$-$C_6$)-alkylene-NH—C(O)—O—($C_1$-$C_4$)-alkylene-(C6-C14)-aryl, where aryl is unsubstituted or substituted by —NH$_2$ or is substituted by —NH$_2$ and once, twice or three times by R15,
10) —($C_0$-$C_4$)-alkylene-NH—C(O)—($C_1$-$C_4$)-alkyl or
11) —($C_0$-$C_4$)-alkylene-($C_6$-$C_{14}$)-aryl, where aryl is unsubstituted or substituted by —NH$_2$ or is substituted by —NH$_2$ and once, twice or three times by R15, or
12) —($C_1$-$C_4$)-alkylene-SO$_x$—($C_1$-$C_4$)-alkylene-NH$_2$ in which x is the integer zero, 1 or 2

R3 is 1) —($C_1$-$C_4$)-alkyl,
2) —($C_0$-$C_4$)-alkylene-($C_3$-$C_8$)-cycloalkyl,
3) —($C_1$-$C_6$)-alkylene-(C6-C14)-aryl, where aryl is substituted independently of one another once, twice or three times by R15,
4) —($C_1$-$C_6$)-alkylene-NH—C(O)—O—($C_1$-$C_4$)-alkylene-(C6-C14)-aryl, where aryl is substituted independently of one another once, twice or three times by R15,
5) —($C_1$-$C_6$)-alkylene-NH-PG1,
6) —($C_1$-$C_6$)-alkylene-O-PG2,
7) —($C_1$-$C_6$)-alkyl, or
8) hydrogen atom,
where PG1 is t-butyloxycarbonyl or benzyloxycarbonyl, and PG2 is t-butyl-, t-butyloxycarbonyl or benzyloxycarbonyl R4 is —N(R6)$_2$,
where R6 are identical or different and are independently of one another
1) hydrogen atom,
2) —($C_1$-$C_6$)-alkyl,
3) —($C_0$-$C_4$)-alkylene-($C_3$-$C_{12}$)-cycloalkyl, where cycloalkyl is unsubstituted or substituted independently of one another once, twice, three or four times by R11, halogen, —C(O)—O—R11, —($C_1$-$C_4$)-alkyl-O—R11 or —O—($C_1$-$C_4$)-alkyl,
4) —($C_0$-$C_4$)-alkylene-C(R11)(R12)-($C_3$-$C_{12}$)-cycloalkyl, where cycloalkyl is unsubstituted or substituted independently of one another once, twice or three times by R11, halogen, —C(O)—O—R11, —($C_1$-$C_4$)-alkyl-O—R11 or 30-O—($C_1$-$C_4$)-alkyl,
5) —($C_0$-$C_4$)-alkylene-Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —($C_1$-$C_4$)-alkyl-O—R11 or —O—($C_1$-$C_4$)-alkyl,
6) —($C_0$-$C_6$)-alkylene-(C6-C14)-aryl, where aryl or alkylene is unsubstituted or substituted independently of one another once, twice or three times by R11, halogen, —C(O)—O—R11, —($C_0$-$C_4$)-alkyl-O—R11 or —O—($C_1$-$C_4$)-alkyl,
7) —($C_0$-$C_4$)-alkylene-C(R11)(R12)-aryl, where aryl or alkylene is unsubstituted or substituted independently of one another once, twice or three times by R11, halogen, —C(O)—O—R11, —($C_0$-$C_4$)-alkyl-O—R11 or —O—($C_1$-$C_4$)-alkyl,
8) 1,2,3,4-tetrahydronaphthalenyl,
9) —($C_0$-$C_4$)-alkylene-CH(R11)-C(O)—NH$_2$,
10) —($C_0$-$C_4$)-alkylene-CH(R11)-C(O)—NH—($C_1$-$C_4$)-alkyl,
11) —($C_0$-$C_4$)-alkylene-CH(R11)-C(O)—NH—CH(R12)-R13,
12) —($C_0$-$C_6$)-alkylene-C(O)—O—R11, where alkylene is unsubstituted or substituted independently of one another once or twice by R11, halogen, —C(O)—O—R11, —($C_1$-$C_4$)-alkyl-O—R11 or —O—($C_1$-$C_4$)-alkyl,
13) —($C_0$-$C_4$)-alkylene-C(R11)(R12)-C(O)—O—R11, or
14) —($C_1$-$C_3$)-fluoroalkyl,
or the two R6 radicals form together with the N atom to which they are bonded a mono- or bicyclic ring having 4 to 9 ring atoms which is saturated, partly saturated or aromatic, where the ring is unsubstituted or substituted once or twice by —($C_1$-$C_4$)-alkyl, —C(O)—O—R11, halogen, —($C_1$-$C_4$)-alkyl-O—R11 or phenyl, R7 is hydrogen atom or —($C_1$-$C_4$)-alkyl,
R9 is hydrogen atom or —($C_1$-$C_4$)-alkyl,
R11 and R12 are identical or different and are independently of one another
1) hydrogen atom,
2) —($C_1$-$C_4$)-alkyl,
3) —($C_0$-$C_4$)-alkylene-phenyl, where phenyl is unsubstituted or substituted independently of one another once, twice or three times by halogen, —OH or —O—($C_1$-$C_4$)-alkyl,
4) —($C_0$-$C_4$)-alkylene-($C_3$-$C_{12}$)-cycloalkyl, where cycloalkyl is unsubstituted or substituted independently of one another once, twice, three or four times by R13, halogen, —C(O)—O—R13, —($C_1$-$C_4$)-alkyl-O—R13, —O—($C_1$-$C_4$)-alkyl or —($C_0$-$C_4$)-alkylene-phenyl,
5) —($C_0$-$C_4$)-alkylene-C(O)—N(R13)$_2$ or
6) —($C_0$-$C_4$)-alkylene-indolyl, R13 is 1) hydrogen atom,
2) —($C_1$-$C_4$)-alkyl,
3) —($C_0$-$C_4$)-alkylene-C(O)—O—R14, 4) —($C_0$-$C_4$)-alkylene-C(O)—R14 or
5) —($C_0$-$C_4$)-alkylene-O—R14,
R14 is hydrogen atom, —($C_1$-$C_4$)-alkyl, —$NH_2$ or —OH, and
R15 is hydrogen atom, —($C_1$-$C_4$)-alkyl, —O—$CF_3$, —$NH_2$, —OH, —$CF_3$ or halogen.

The invention also relates to the compound of the formula I where
X is —C(O)—,
R1 is 1) hydrogen atom or
2) —($C_1$-$C_4$)-alkyl,
R2 is 1) —($C_1$-$C_6$)-alkylene-$NH_2$,
2) —($C_1$-$C_4$)-alkylene-pyridyl-$NH_2$,
3) —($C_1$-$C_4$)-alkylene-piperidinyl-$NH_2$,
4) —($C_1$-$C_6$)-alkylene-NH—C(=NH)—$NH_2$,
5) —($C_0$-$C_4$)-alkylene-($C_3$-$C_6$)-cycloalkyl-$NH_2$,
6) —($C_1$-$C_6$)-alkylene-NH—C(=NH)—($C_1$-$C_4$)-alkyl,
7) —($C_1$-$C_4$)-alkylene-O—NH—C(=NH)—$NH_2$,
8) —($C_1$-$C_6$)-alkylene-NH—C(O)—O—($C_1$-$C_4$)-alkylene-phenyl, where phenyl is unsubstituted or substituted by —$NH_2$ or is substituted by —$NH_2$ and once, twice or three times by R15,
9) —($C_1$-$C_4$)-alkylene-NH—C(O)—($C_1$-$C_6$)-alkyl,
10) —($C_1$-$C_4$)-alkylene-phenyl, where phenyl is unsubstituted or substituted by —$NH_2$ or is substituted by —$NH_2$ and once, twice or three times by R15,
11) alkylene-$SO_2$—($C_1$-$C_4$)-alkylene-$NH_2$ or
12) —($C_1$-$C_4$)-alkylene-S—($C_1$-$C_4$)-alkylene-$NH_2$,
R3 is 1) —($C_1$-$C_4$)-alkyl,
2) —($C_1$-$C_4$)-alkylene-($C_3$-$C_6$)-cycloalkyl,
3) —($C_1$-$C_4$)-alkylene-phenyl, where phenyl is substituted independently of one another once, twice or three times by R15,
4) —($C_1$-$C_6$)-alkylene-NH—C(O)—O—($C_1$-$C_4$)-alkylene-phenyl, where phenyl is substituted independently of one another once, twice or three times by R15,
5) hydrogen atom,
R4 is —N(R6)$_2$,
where R6 are identical or different and are independently of one another
1) hydrogen atom,
2) —($C_1$-$C_4$)-alkyl,
3) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, 1,7,7-trimethylbicyclo[3.1.1]heptanyl, decahydronaphthalenyl, tetrahydronaphthalenyl, octahydro-4,7-methanoindenyl or bicyclo[2.2.1]heptanyl and in which cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen,
4) —($C_0$-$C_4$)-alkylene-C(R11)(R12)-($C_3$-$C_{12}$)-cycloalkyl, where cycloalkyl is selected from the group consisting of cyclohexyl, cyclopentyl, cyclobutyl, cyclopropyl, adamantanyl, 1,7,7-trimethylbicyclo[3.1.1]heptanyl, decahydronaphthalenyl, tetrahydronaphthalenyl, octahydro-4,7-methanoindenyl or bicyclo[2.2.1]-heptanyl and in which cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen,
5) —($C_0$-$C_4$)-alkylene-Het, where Het is selected from the group consisting of acridinyl, azepinyl, azetidinyl, aziridinyl, benzimidazalinyl, benzimidazolyl, benzo[1,3]dioxolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2, 5-thiadazinyl, 1,2,3-thia-diazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thieno-thiazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl, where Het or alkylene is unsubstituted or substituted independently of one another once or twice by —($C_1$-$C_4$)-alkyl,
6) —($C_1$-$C_6$)-alkylene-phenyl, where phenyl or alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl,
7) —($C_0$-$C_4$)-alkylene-C(R11)(R12)-phenyl, where phenyl is unsubstituted or substituted independently of one another once, twice or three times by phenyl or fluorine,
8) 1,2,3,4-tetrahydronaphthalenyl,
9) —($C_0$-$C_4$)-alkylene-CH(R11)-C(O)—$NH_2$,
10) —($C_0$-$C_4$)-alkylene-CH(R11)-C(O)—NH—($C_1$-$C_4$)-alkyl,
11) —($C_0$-$C_4$)-alkylene-CH(R11)-C(O)—NH—CH(R12)-R13,
12) —($C_1$-$C_6$)-alkylene-C(O)—O—R11, where alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl,
13) —($C_0$-$C_4$)-alkylene-C(R11)(R12)-C(O)—O—R11, or
14) —($C_1$-$C_3$)-fluoroalkyl,
or the two R6 radicals form together with the N atom to which they are bonded a mono- or bicyclic ring selected from the group consisting of pyrrolidine, piperidine, 2-aza-bicyclo[3.2.2]nonane and 7-aza-bicyclo[2.2.1]heptane, where the ring is unsubstituted or substituted once or twice by —($C_1$-$C_4$)-alkyl, —C(O)—O—R11, —($C_1$-$C_4$)-alkyl-O—R11 or phenyl,
R7 is hydrogen atom or —($C_1$-$C_4$)-alkyl,
R9 is hydrogen atom or —($C_1$-$C_4$)-alkyl, R11 and R12 are identical or different and are independently of one another
1) hydrogen atom,
2) —($C_1$-$C_4$)-alkyl,
3) —($C_0$-$C_4$)-alkylene-phenyl, where phenyl is unsubstituted or substituted independently of one another once, twice or three times by —OH, halogen or —O—($C_1$-$C_4$)-alkyl,
4) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, bicyclo[3.1.1]heptanyl, decahydronaphthalenyl, octahydro-4,7-methanoindenyl or bicyclo[2.2.1]heptanyl and in which cycloalkyl is unsubstituted or substituted independently of one another once, twice, three or four times by —($C_1$-$C_4$)-alkyl, —C(O)—O—R13 or phenyl, or
5) —($C_0$-$C_4$)-alkylene-indolyl,
R13 is 1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14, and
R14 is hydrogen atom, —($C_1$-$C_4$)-alkyl, —$NH_2$ or —OH and
R15 is hydrogen atom, —($C_1$-$C_4$)-alkyl, —O—$CF_3$, —$NH_2$, —OH, —$CF_3$ or halogen.
The invention also relates to the compound of the formula I where
X is —C(O)—,
R1 is 1) hydrogen atom or
2) —($C_1$-$C_4$)-alkyl,
R2 is 1) —($C_1$-$C_6$)-alkylene-$NH_2$,
2) —($C_1$-$C_4$)-alkylene-pyridyl-$NH_2$,
3) —($C_1$-$C_4$)-alkylene-piperidinyl-$NH_2$,
4) —($C_1$-$C_4$)-alkylene-NH—C(=NH)—$NH_2$,
5) —($C_1$-$C_6$)-alkylene-NH—C(=NH)—($C_1$-$C_4$)-alkyl,
6) —($C_1$-$C_4$)-alkylene-($C_3$-$C_6$)-cycloalkyl-$NH_2$,
7) —($C_1$-$C_4$)-alkylene-O—NH—C(=NH)—$NH_2$,
8) —($C_1$-$C_6$)-alkylene-NH—C(O)—O—($C_1$-$C_4$)-alkylene-phenyl,
9) —($C_1$-$C_4$)-alkylene-NH—C(O)—($C_1$-$C_6$)-alkyl or
10) —($C_1$-$C_4$)-alkylene-phenyl-$NH_2$,
11) ($C_1$-$C_2$)-alkylene-$SO_2$—($C_1$-$C_4$)-alkylene-$NH_2$ or
12) —($C_1$-$C_2$)-alkylene-S—($C_1$-$C_4$)-alkylene-$NH_2$,
R3 is 1) —($C_1$-$C_4$)-alkyl,
2) —($C_1$-$C_4$)-alkylene-($C_3$-$C_6$)-cycloalkyl,
3) —($C_1$-$C_4$)-alkylene-phenyl, where phenyl is unsubstituted or substituted by —OH,
4) —($C_1$-$C_6$)-alkylene-NH—C(O)—O—($C_1$-$C_4$)-alkylene-phenyl,
5) hydrogen atom,
R4 is —N(R6)$_2$,
where R6 are identical or different and are independently of one another
1) hydrogen atom,
2) —($C_1$-$C_6$)-alkyl,
3) —($C_0$-$C_4$)-alkylene-($C_3$-$C_8$)-cycloalkyl, where cycloalkyl is selected from the group consisting of cyclohexyl, cyclopentyl, cyclopropyl, adamantyl, decahydronaphthalenyl, octahydro-4,7-methanoindenyl and bicyclo[2.2.1]heptanyl, and in which cycloalkyl is unsubstituted or substituted independently of one another once, twice or three times by —($C_1$-$C_4$)-alkyl or phenyl, or 1,7,7-trimethylbicyclo[3.1.1]heptanyl, which is unsubstituted or substituted once by —($C_1$-$C_4$)-alkyl or phenyl
4) —C(R11)(R12)-adamantanyl, 5) —CH(R11)-C(O)—NH—CH(R12)-R13,
6) —($C_0$-$C_4$)-alkylene-Het, where Het is selected from the group consisting of benzimidazolyl, isoxazolyl, piperidinyl, pyridyl, pyrrolidinyl, thiophenyl and benzo[1,3]dioxolyl,
7) 1,2,3,4-tetrahydronaphthalenyl,
8) —($C_0$-$C_4$)-alkylene-C(R11)(R12)-phenyl, where phenyl is unsubstituted or substituted independently of one another once, twice or three times by phenyl or fluorine,
9) —CH(R11)-C(O)—$NH_2$,
10) —CH(R11)-C(O)—NH—CH(R12)-$CH_2$—OH,
11) —($C_1$-$C_6$)-alkylene-phenyl, where phenyl or alkylene is unsubstituted or substituted independently of one another once or twice by chlorine, fluorine, —C(O)—O—R11, —($C_1$-$C_4$)-alkyl-O—R11, —O—($C_1$-$C_4$)-alkyl, phenyl or —($C_1$-$C_4$)-alkyl,
12) —CH(R11)-C(O)—NH—($C_1$-$C_4$)-alkyl,
13) —($C_0$-$C_4$)-alkylene-C(R11)(R12)-bicyclo[3.1.1]heptanyl, where bicyclo[3.1.1]heptanyl is unsubstituted or substituted once to four times by —($C_1$-$C_4$)-alkyl,
14) —($C_1$-$C_6$)-alkylene-C(O)—O—R11, where alkylene is unsubstituted or substituted independently of one another once or twice by chlorine, fluorine, —C(O)—O—R11, —($C_1$-$C_4$)-alkyl-O—R11, —O—($C_1$-$C_4$)-alkyl, phenyl or —($C_1$-$C_4$)-alkyl,
15) —($C_0$-$C_4$)-alkylene-C(R11)(R12)-C(O)—O—R11, or
16) —$CH_2$—$CF_2$—$CF_3$,
or the two R6 radicals form together with the N atom to which they are bonded a mono- or bicyclic ring selected from the group consisting of pyrrolidines, 2-azabicyclo[3.2.2]nonane and 7-aza-bicyclo[2.2.1]heptane, where the ring is unsubstituted or substituted once or twice by —($C_1$-$C_4$)-alkyl, —C(O)—O—R11, —($C_1$-$C_4$)-alkyl-O—R11 or phenyl,
R7 is hydrogen atom or —($C_1$-$C_4$)-alkyl,
R9 is hydrogen atom or —($C_1$-$C_4$)-alkyl,
R11 and R12 are identical or different and are independently of one another
1) hydrogen atom,
2) —($C_1$-$C_4$)-alkyl,
3) —($C_0$-$C_4$)-alkylene-phenyl, where phenyl is unsubstituted or substituted independently of one another once, twice or three times by —OH, halogen or —O—($C_1$-$C_4$)-alkyl,
4) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, decahydronaphthalenyl, octahydro-4,7-methanoindenyl and bicyclo[2.2.1]heptanyl, and in which cycloalkyl is unsubstituted or substituted independently of one another once, twice, three or four times by —($C_1$-$C_4$)-alkyl, —C(O)—O—R13 or phenyl, or 1,7,7-trimethylbicyclo[3.1.1]heptanyl, which is unsubstituted or substituted once by —($C_1$-$C_4$)-alkyl, —C(O)—O—R13 or phenyl
5) —($C_0$-$C_4$)-alkylene-indolyl,
R13 is 1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14,
R14 is hydrogen atom, —($C_1$-$C_4$)-alkyl, —$NH_2$ or —OH and
R15 is hydrogen atom, —($C_1$-$C_4$)-alkyl, —O—$CF_3$, —$NH_2$, —OH, —$CF_3$ or halogen.
The invention also relates to a process for preparing the compound of the formula I, which comprises
a) reacting a compound of the formula II

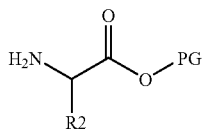

(II)

where R2 and PG have the meanings mentioned in the compound of the formula I, with a phosgene equivalent such as carbonyldiimidazole, diphosgene, triphosgene or phosgene to give an intermediate of the formula III

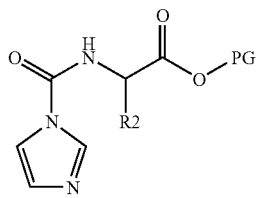

(III)

where R2 and PG have the meanings mentioned in the compound of the formula I, and reacting the compound of the formula III with an amino acid of the formula IV

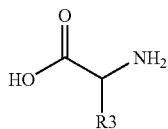

(IV)

where R3 has the meaning mentioned in the compound of the formula I, to give a compound of the formula V

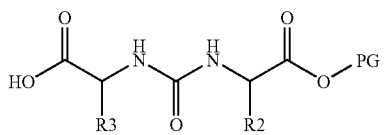

(V)

where R2, R3 and PG have the meanings mentioned in the compound of the formula I, and subsequently the compound of the formula V is reacted with an amine of the formula NH(R6)$_2$, where R6 has the meaning mentioned in the compound of the formula I, to give a compound of the formula VI

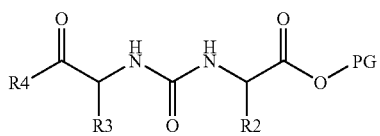

(VI)

where R2, R3, R4 and PG have the meanings mentioned in the compound of the formula I, and is then converted into a compound of the formula I, or b) a compound of the formula II is reacted with a compound of the formula IX

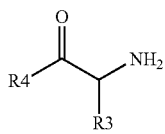

(IX)

where R3, R4 and PG have the meanings mentioned in the compound of the formula I, to give a compound of the formula X

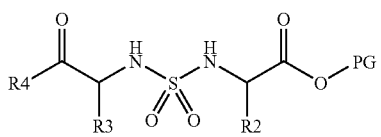

(X)

where R2, R3, R4 and PG have the meanings mentioned in the compound of the formula I, and is then converted into a compound of the formula I, or c) fractionating a compound of the formula I prepared by processes a) or b), or a suitable precursor of the formula I which occurs in enantiomeric forms owing to its chemical structure, by salt formation with enantiopure acids or bases, chromatography on chiral stationary phases or derivatization by means of chiral enantiopure compounds such as amino acids, separation of the diastereomers obtained in this way, and elimination of the chiral auxiliary groups into the pure enantiomers, or d) either isolating in free form the compound of the formula I prepared by processes a), b) or c), or converting into physiologically tolerated salts in the case where acidic or basic groups are present.

Compounds of the invention of the formula (I) are prepared for example by treating amino acid (II) with a phosgene equivalent such as carbonyldiimidazole, diphosgene, triphosgene or phosgene in an inert solvent such as DMF or dichloromethane, and reacting the intermediate (III) resulting in this case with an amino acid (IV) which is commercially available or prepared by removing protective groups, to give a compound (V), where PG is defined as in the compound of the formula I. A peptide linkage of (V) with (VI) is then formed by processes known from the literature, for example in the presence of a carbodiimide or with preactivation with (V) as active ester by adding for example 1-hydroxybenzotriazole in inert solvents such as dimethylformamide (DMF) or dichloromethane. The final deprotection to give (I) in turn takes place by the processes quoted above for eliminating protective groups as shown in Scheme 1 below.

Scheme 1

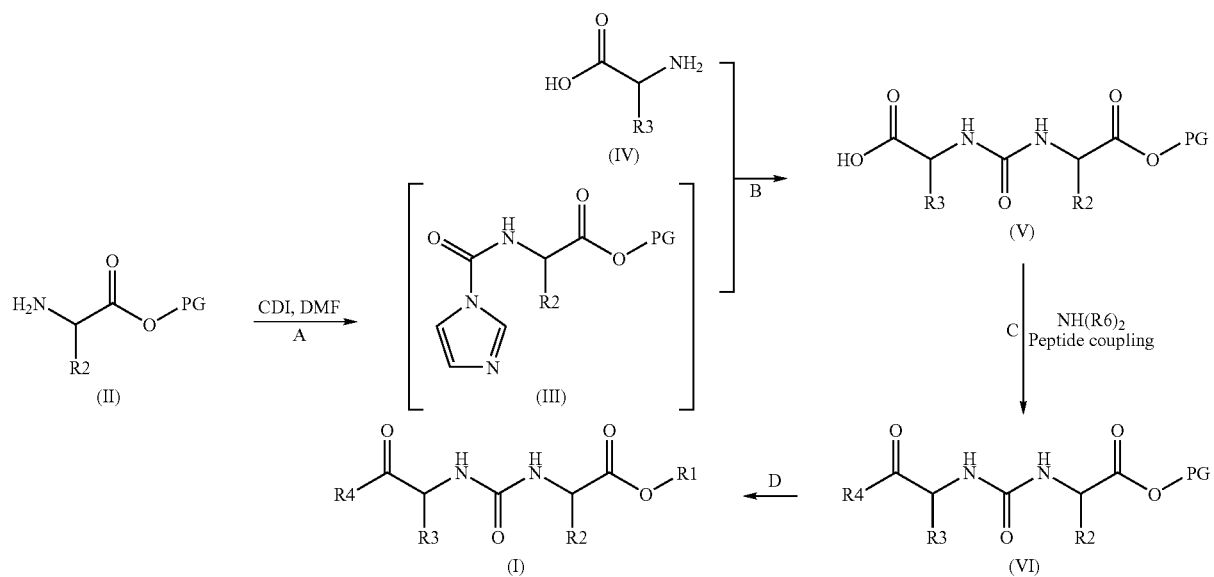

As an alternative thereto, the sequence of the process steps can also be varied by reacting compounds of the formula (IV) with $NH(R6)_2$ as in process step C and subsequently carrying out process steps B and D.

Scheme 2

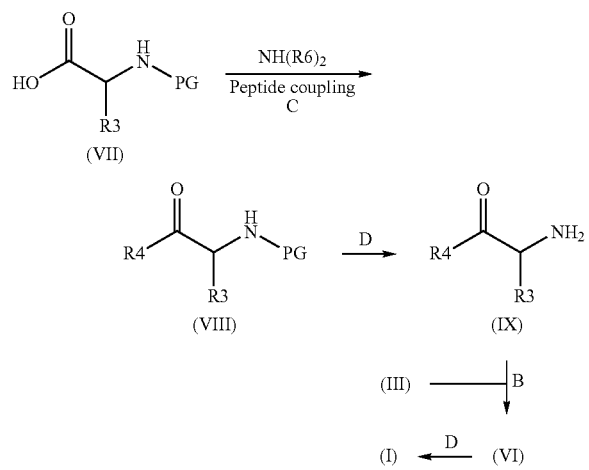

A further process for preparing the compounds of the invention according to (I) is reaction of compounds (IX) with compounds of the type (II) in analogy to A. In a process disclosed by Borghese et al. (*Org. Process Res. Dev.* 2006, 10, 770-775), compounds of the formula X are prepared and are subsequently deprotected and afford compounds of the formula I:

Scheme 3

(II) + (IX) $\xrightarrow{E}$

-continued

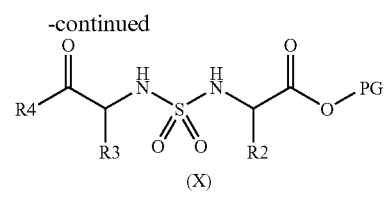

Amines of the formula $NH(R6)_2$ mean amines or dipeptide derivatives which are commercially available or prepared by processes disclosed in the literature. The compounds (II) are commercially available or can be obtained by alkylation of tert-butyl (benzhydrylideneamino)acetate in suitable solvents such as THF or DMF in the presence of bases such as lithiumhexamethyldisilazane, KOH, NaOH, CsOH, $K_2CO_3$ or NaH and subsequent deprotection under acidic conditions, for example in dilute hydrochloric acid or aqueous citric acid (Scheme 4, cf., for example, J. Ezquerra et al., *Tetrahedron Lett.* 1993, 34 (52), 8535-8538). The compounds (XI) are commercially available or disclosed in the literature, where X is a suitable leaving group such as bromine, iodine, chlorine, tosylate or mesylate.

Scheme 4

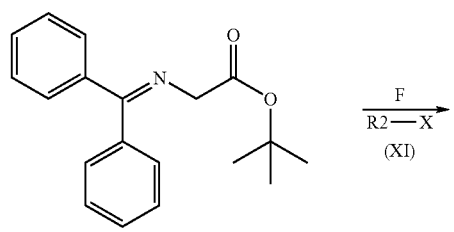

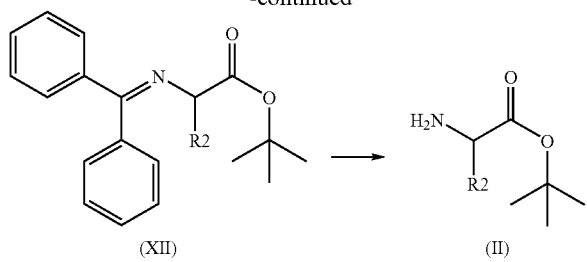

A compound of the formula I prepared as in Scheme 1 or 3, or a suitable precursor of the formula I which occurs in enantiomeric form owing to its chemical structure, can be fractionated by salt formation with enantiopure acids or bases, chromatography on chiral stationary phases or derivatization by means of chiral enantiopure compounds such as amino acids, separation of the diastereomers obtained in this way, and elimination of the chiral auxiliary groups into the pure enantiomers (process b), or the compound of the formula I prepared as in Scheme 1 or 3 can either be isolated in free form or be converted into physiologically tolerated salts in the case where acetic or basic groups are present (process d).

In process step c), the compound of the formula I, if it occurs as mixture of diastereomers or enantiomers, or results as mixtures thereof in the chosen synthesis, is separated into the pure stereoisomers, either by chromatography on an optionally chiral support material or, if the racemic compound of the formula I is able to form salts, by fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes it is also possible to use gas chromatography methods, after appropriate derivatization known to the skilled worker, on chiral stationary phases. To separate enantiomers of the racemic carboxylic acids, diastereomeric salts differing in solubility are formed with an optically active, usually commercially available base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I comprising a basic group such as an amino group with optically active acids such as (+)-camphor-10-sulfonic acid, D- and L-tartaric acid, D- and L-lactic acid, and (+) and (−)-mandelic acid into the pure enantiomers. Chiral compounds comprising alcohol or amine functions can also be converted with appropriately activated or optionally N-protected enantiopure amino acids into the corresponding esters or amides, or conversely chiral carboxylic acids can be converted with carboxy-protected enantiopure amino acids into the amides, or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers now present by crystallization or chromatography on suitable stationary phases, and then eliminating the included chiral moiety again by suitable methods.

A further possibility with some of the compounds of the invention is to employ diastereomerically or enantiomerically pure starting materials to prepare the framework structures. It is thus possible where appropriate also to employ other or simplified processes for purifying the final products. These starting materials have previously been prepared enantiomerically or diastereomerically pure by processes known from the literature. This may mean in particular that either enantioselective processes are employed in the synthesis of the basic structures, or else a separation of enantiomers (or diastereomers) is carried out at an early stage of the synthesis and not at the stage of the final products. A simplification of these separations can likewise be achieved by proceeding in two or more stages.

Acidic or basic products of the compound of the formula I may be in the form of their salts or in free form. Pharmacologically acceptable salts are preferred, for example alkali metal or alkaline earth metal salts such as hydrochlorides, hydrobromides, sulfates, hemisulfates, all possible phosphates, and salts of amino acids, natural bases or carboxylic acids. Physiologically tolerated salts are prepared from compounds of the formula I able to form salts, including their stereoisomeric forms, in step c) of the process in a manner known per se. The compounds of the formula I form stable alkali metal, alkaline earth metal or, where appropriate, substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. If the compounds of the formula I have basic groups, it is also possible to prepare stable acid addition salts with strong acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic, or trifluoroacetic acid.

The invention also relates to medicaments characterized by an effective content of at least one compound of the formula I and/or of a physiologically tolerated salt of the compound of the formula I and/or an optionally stereoisomeric form of the compound of the formula I, together with a pharmaceutically suitable and physiologically tolerated carrier, additive and/or further active ingredients and excipients.

By reason of the pharmacological properties, the compounds of the invention are suitable for the prophylaxis, secondary prevention and therapy of all disorders which can be treated by inhibition of TAFIa. Thus, TAFIa inhibitors are suitable both for a prophylactic and for a therapeutic use in humans. They are suitable both for an acute treatment and for a long-term therapy. TAFIa inhibitors can be employed in patients suffering from impairments of wellbeing or diseases associated with thromboses, embolisms, hypercoagulability or fibrotic changes.

These include myocardial infarction, angina pectoris and all other types of acute coronary syndrome, stroke, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations. TAFIa inhibitors can additionally be employed in all procedures leading to contact of the blood with foreign surfaces such as, for example, for dialysis patients and patients with indwelling catheters. TAFIa inhibitors can be employed to reduce the risk of thrombosis after surgical procedures such as knee and hip joint operations.

TAFIa inhibitors are suitable for the treatment of patients with disseminated intravascular coagulation, sepsis and other intravascular events associated with an inflammation. TAFIa inhibitors are additionally suitable for the prophylaxis and treatment of patients with atherosclerosis, diabetes and the metabolic syndrome and the sequelae thereof. Impairments of the hemostatic system (e.g. fibrin deposits) have been implicated in mechanisms leading to tumor growth and tumor metastasis, and for inflammatory and degenerative articular disorders such as rheumatoid arthritis and arthrosis. TAFIa inhibitors are suitable for slowing down or preventing such processes.

Further indications for the use of TAFIa inhibitors are fibrotic changes of the lung such as chronic obstructive lung disease, adult respiratory distress syndrome (ARDS) and of the eye such as fibrin deposits after eye operations. TAFIa inhibitors are also suitable for the prevention and/or treatment of scar formation.

The medicaments of the invention can be administered by oral, inhalational, rectal or transdermal administration or by subcutaneous, intraarticular, intraperitoneal or intravenous injection. Oral administration is preferred. It is possible for stents and other surfaces which come into contact with blood in the body to be coated with TAFIa inhibitors.

The invention also relates to a process for producing a medicament, which comprises making a suitable dosage form from at least one compound of the formula I with a pharmaceutically suitable and physiologically tolerated carrier and, where appropriate, further suitable active ingredients, additives or excipients.

Suitable solid or pharmaceutical formulations are, for example, granules, powder, coated tablets, tablets, (micro) capsules, suppositories, syrups, solutions, suspensions, emulsions, drops or injectable solutions, and products with protracted release of active ingredient, in the production of which conventional aids such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, where each unit comprises as active ingredient a particular dose of the compound of the invention of the formula I. In the case of solid dosage units such as tablets, capsules, coated tablets or suppositories, this dose can be up to about 1000 mg, but preferably about 50 to 300 mg and, in the case of injection solutions in ampoule form, up to about 300 mg but preferably about 10 to 100 mg.

The daily doses indicated for the treatment of an adult patient weighing about 70 kg are, depending on the activity of the compound of formula I, from about 2 mg to 1000 mg of active ingredient, preferably about 50 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

TAFIa inhibitors can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics.

EXAMPLES

Final products are normally determined by mass spectroscopic methods (FAB-, ESI-MS) and $^1$H-NMR; the main peak or two main peaks are indicated in each case. Temperatures are stated in degrees Celsius, RT means room temperature (21° C. to 24° C.). Abbreviations used are either explained or correspond to usual conventions. Unless stated otherwise, the LC/MS analyses were carried out under the following conditions:

Method A:=method column: YMC Jsphere H80 20×2 mm, packing material 4 μm, mobile phase: $CH_3CN$:$H_2O$+0.05% trifluoroacetic acid (TFA), gradient: 4:96 (0 min.) to 95:5 (2.0 min.) to 95:5 (2.4 min.) to 4:96 (2.45 min.) flow rate: 1.0 ml/min., temperature: 30° C.

Method B: column: YMC Jsphere 33×2.1 mm, packing material 4 μm, mobile phase: $CH_3CN$+0.05% TFA:$H_2O$+0.05% TFA, gradient: 5:95 (0 min.) to 95:5 (2.5 min.) to 95:5 (3.0 min.), flow rate: 1.3 ml/min., temperature: 30° C.

Method C: column: YMC Jsphere 33×2.1 mm, packing material 4 μm, mobile phase: $CH_3CN$+0.08% formic acid:$H_2O$+0.1% formic acid, gradient: 5:95 (0 min.) to 95:5 (2.5 min.) to 95:5 (3.0 min.), flow rate: 1.3 ml/min., temperature: 30° C.

Method D: column: YMC Jsphere 33×2.1 mm, packing material 4 μm, mobile phase: $CH_3CN$+0.05% TFA:$H_2O$+0.05% TFA, gradient: 5:95 (0-0.5 min.) to 95:5 (3.5 min.) to 95:5 (4.0 min.), flow rate: 1.3 ml/min., temperature: 30° C.

Method E: column: YMC Jsphere 33×2.1 mm, packing material 4 μm, mobile phase: $CH_3CN$+0.05% TFA:$H_2O$+0.05% TFA, gradient: 2:98 (0-1.0 min.) to 95:5 (5.0 min.) to 95:5 (6.2 min.), flow rate: 1.0 ml/min., temperature: 30° C.

Method F: column: YMC Jsphere 33×2.1 mm, packing material 4 μm, mobile phase: $CH_3CN$+0.05% TFA:$H_2O$+0.05% TFA, gradient: 5:95 (0 min.) to 95:5 (3.4 min.) to 95:5 (4.4 min.), flow rate: 1.0 ml/min., temperature: 30° C.

Unless indicated otherwise, chromatographic separations were carried out on silica gel with ethyl acetate/heptane mixtures as mobile phase. Preparative separations on reversed phase (RP) silica gel (HPLC) were, unless indicated otherwise, carried out under the following conditions: column Merck Hibar RT 250-25 LiChrospher 100 RP-18e 5 μm, mobile phase A: $H_2O$+0.1% TFA, phase B: 80% acetonitrile+ 0.1% TFA, flow rate 25 ml/min., 0-7 min. 100% A, 7-22 min. to 100% B, 22-30 min. 100% B, 30-33 min. to 100% A, 33-35 min. 100% A.

Evaporation of solvents normally took place under reduced pressure in a rotary evaporator at 35° C. to 45° C.

Example 1

(S)-6-Amino-2-{3-[(R)-1-(3-methyl-butylcarbamoyl)-2-phenyl-ethyl]-ureido}-hexanoic acid hydrochloride Example 1a tert-Butyl(R)-1-(3-methyl-butylcarbamoyl)-2-phenyl-ethyl]-carbamate 1-Hydroxybenzotriazole hydrate (1.685 g, 11 mmol) and N,N'-dicyclohexylcarbodiimide (DCC, 2.270 g, 11 mmol)

were successively added to a solution of N-Boc-D-phenylalanine (2.653 g, 10 mmol) in tetrahydrofuran (THF) (80 ml) and stirred at RT for 2 h. Subsequently, isoamylamine (1.162 ml, 10 mmol) was added, and stirring was continued at RT. Leaving to stand overnight was followed by filtration, concentration of the filtrate, taking up in ethyl acetate, renewed filtration, successive washing with saturated NaHCO$_3$ solution and 1N HCl, and the organic phase was dried over MgSO$_4$, filtered and concentrated.

LC/MS data: Rt(min.) 1.568; calculated (calc.): [M+H]$^+$=335.47, found (found): 235.15 (-tert-butyloxycarbonyl during the measurement) (Method A)

Example 1b (R)-2-Amino-N-(3-methyl-butyl)-3-phenyl-propionamide

A solution of the crude product from Example 1a) (2.710 g, 8.103 mmol) in dichloromethane/trifluoroacetic acid (TFA) (60 ml, 1:1 v/v) was stirred at RT for 30 min. The solution was concentrated, taken up in ethyl acetate and washed with 1N HCl. The aqueous phase was made weakly alkaline with potassium hydroxide and extracted three times with ethyl acetate. The combined organic phases were dried over MgSO$_4$, filtered and concentrated.

LC/MS data: R$_t$(min) 0.978; calc.: [M+H]$^+$=235.35 found: 235.15 (method A)

Example 1c tert-Butyl(S)-6-tert-butoxycarbonylamino-2-{3-[(R)-1-(3-methyl-butylcarbamoyl)-2-phenyl-ethyl]-ureido}-hexanoate The crude product from Example 1b) (1.380 g, 5.889 mmol) was added to a solution of 1,1'-carbonyldiimidazole (0.955 g, 5.889 mmol) in dimethylformamide (DMF) (21 ml) and stirred at RT for 1 h. Then triethylamine (1.633 ml, 11.780 mmol) and tert-butyl (S)-2-amino-6-tert-butoxycarbonylaminohexanoate hydrochloride (1.996 g, 5.889 mmol) were added, and the mixture was left to stand at RT overnight. The solution was concentrated and partitioned between water and ethyl acetate, and the organic phase was dried over MgSO$_4$, filtered and concentrated. The resulting crude product was purified by preparative HPLC.

LC/MS data: R$_t$(min) 1.757; calc.: [M+H]$^+$=563.76 found: 563.35 (method A)

Example 1d (S)-6-Amino-2-{3-[(R)-1-(3-methyl-butylcarbamoyl)-2-phenyl-ethyl-ureido}-hexanoic acid hydrochloride The product from Example 1c) (0.500 g, 0.889 mmol) was dissolved in dichloromethane/TFA (10 ml, 1:1, v/v) and stirred at RT for 2 h. The solution was concentrated and purified by preparative HPLC. The combined product fractions were mixed with 2N HCl, concentrated and freeze dried.

LC/MS data: R$_t$(min) 0.971; calc.: [M+H]$^+$=407.54 found: 407.30 (method A)

The following examples were prepared in analogy to Example 1:

| Example | Formula | | LC/MS method | R$_t$ | [M + H]$^+$ calc. | [M + H]$^+$ found |
|---|---|---|---|---|---|---|
| 2 | 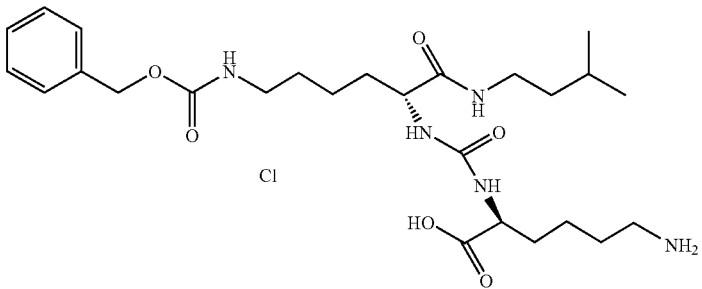 | Chiral | A | 1.067 min | 522.66 | 522.35 |
| 3 | 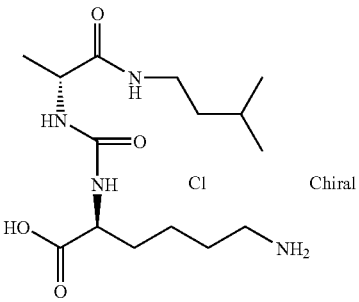 [SMILES: CC(C)CCNC(=O)[C@@H](C)NC(=O)N[C@@H](CCCCN)C(=O)O ; Cl ; "Chiral"] | Chiral | A | 0.788 min | 331.43 | 331.25 |

-continued
| Example | Formula | LC/MS method | $R_t$ | $[M+H]^+$ calc. | $[M+H]^+$ found |
|---|---|---|---|---|---|
| 4 | 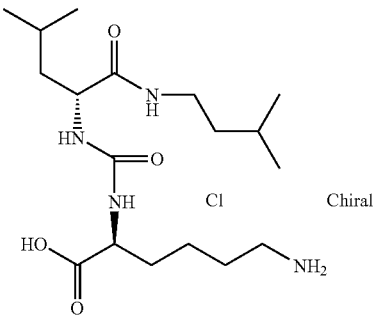 [SMILES: CC(C)CCNC(=O)[C@@H](CC(C)C)NC(=O)N[C@@H](CCCCN)C(=O)O ; Cl ; "Chiral"] | A | 0.974 min | 373.51 | 373.25 |
| 5 | 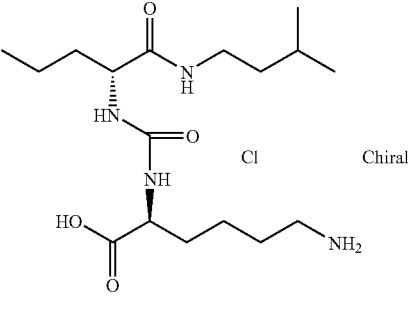 [SMILES: CCC[C@@H](NC(=O)N[C@@H](CCCCN)C(=O)O)C(=O)NCCC(C)C ; Cl ; "Chiral"] | A | 0.931 min | 359.48 | 359.25 |
| 6 | 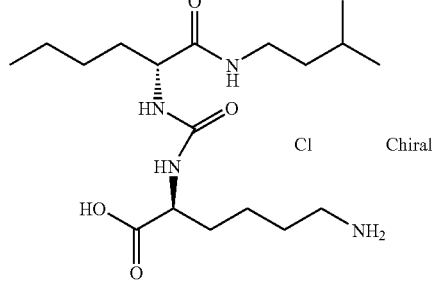 | A | 0.980 min | 373.51 | 373.25 |
| 7 | 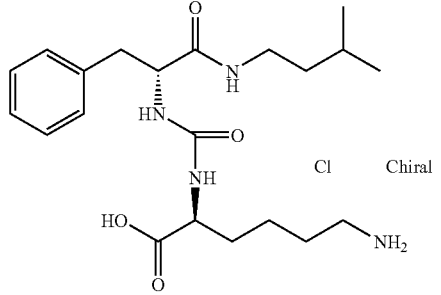 [SMILES: CC(C)CCNC(=O)[C@@H](Cc1ccccc1)NC(=O)N[C@@H](CCCCN)C(=O)O ; Cl ; "Chiral"] | A | 1.021 min | 407.53 | 407.25 |
| 8 | 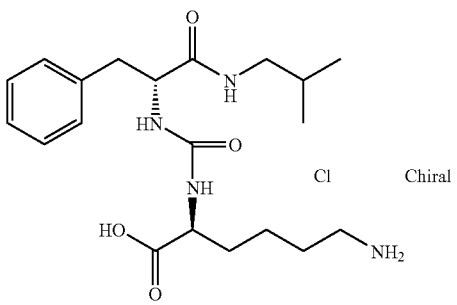 [SMILES: CC(C)CNC(=O)[C@@H](Cc1ccccc1)NC(=O)N[C@@H](CCCCN)C(=O)O ; Cl ; "Chiral"] | A | 0.943 min | 393.5 | 393.25 |

| Example | Formula | LC/MS method | $R_t$ | $[M+H]^+$ calc. | $[M+H]^+$ found |
|---------|---------|--------------|-------|-----------------|-----------------|
| 9 | 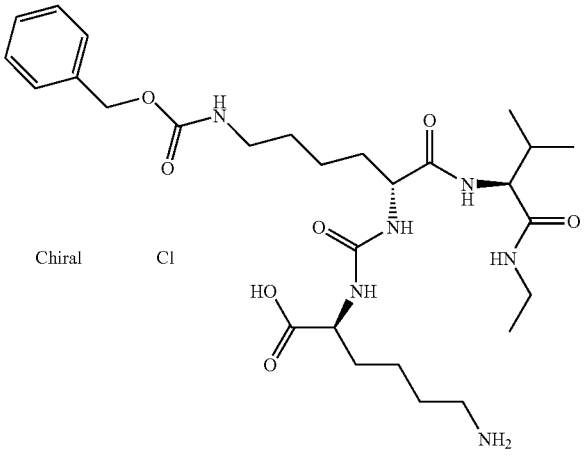 [SMILES: CCNC(=O)[C@@H](NC(=O)[C@@H](CCCCNC(=O)OCc1ccccc1)NC(=O)N[C@@H](CCCCN)C(=O)O)C(C)C ; "Chiral" ; Cl] | A | 1.052 min | 579.71 | 579.35 |
| 10 | 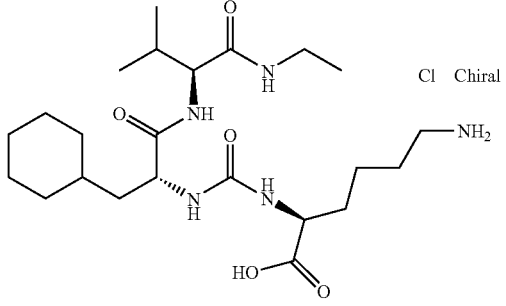 | A | 1.042 min | 470.63 | 470.35 |

Example 11

(S)-6-Amino-2-{3-[(R)-2-cyclohexyl-1-(2,4-difluoro-benzylcarbamoyl)-ethyl]-ureido}-hexanoic acid

Example 11a (R)-2-Amino-3-cyclohexylpropanoic acid trifluoroacetate 5 ml of TFA were added to a solution of (R)-N-Boc-2-amino-3-cyclohexylpropanoic acid (3.0 g, 11.1 mmol) in 20 ml of $CH_2Cl_2$, and the mixture was stirred at RT overnight. After deprotection was complete, the $CH_2Cl_2$ was evaporated off, and the remaining solid was mixed with 50 ml of $H_2O$ and lyophilized. Yield: 2.84 g (90%) of (R)-2-amino-3-cyclohexylpropanoic acid trifluoroacetate as colorless solid.

Example 11b tert-Butyl(S)-6-tert-butoxycarbonylamino-2-[3-((R)-1-carboxy-2-cyclohexyl-ethyl)-ureido]-hexanoate Commercial tert-butyl(S)-2-amino-6-tert-butoxycarbonylaminohexanoate hydrochloride (1.95 g, 5.75 mmol) was mixed in 30 ml of DMF with $NEt_3$ (0.8 ml, 5.754 mmol) and 1,1'-carbonyldiimidazole (0.933 g, 5.754 mmol) and stirred at RT for 30 min. Then (R)-2-amino-3-cyclohexylpropanoic acid trifluoroacetate (1.64 g, 5.754 mmol) and $NEt_3$ (1.6 ml, 11.5 mmol) were added, and the mixture was heated at 80° C. until the imidazolide formed as intermediate was completely converted. The product was purified by flash chromatography on silica gel ($CH_2Cl_2$/MeOH gradient). Yield: 2.1 g (73%) of tert-butyl(S)-6-tert-butoxycarbonylamino-2-[3-((R)-1-carboxy-2-cyclohexylethyl)-ureido]-hexanoate.

Example 11c (S)-6-Amino-2-{3-[(R)-2-cyclohexyl-1-(2,4-difluoro-benzylcarbamoyl)-ethyl]-ureido}-hexanoic acid trifluoroacetate N-Methylmorpholine (53 μl, 0.48 mmol), 1-hydroxybenzotriazole (28 mg, 0.208 mmol) and 1-(3-dimethylaminopropyl)-3-ethylcarbodiimide hydrochloride (36.8 mg, 0.192 mmol) were added in the stated sequence to a solution of tert-butyl(S)-6-tert-butoxycarbonylamino-2-[3-((R)-1-carboxy-2-cyclohexyl-ethyl)-ureido]-hexanoate (80 mg, 0.16 mmol) and 2,4-difluorobenzylamine (22.9 mg, 0.16 mmol) in 3 ml of $CH_2Cl_2$ and 1 ml of DMF, and the mixture was stirred at RT for about 14 h. Extraction with $CH_2Cl_2/H_2O$, drying of the organic phase with $MgSO_4$ and evaporation afforded tert-butyl (S)-6-tert-butoxycarbonylamino-2-{3-[(R)-2-cyclohexyl-1-(2,4-difluorobenzylcarbamoyl)-ethyl]-ureido}-hexanoate as crude product. The entire crude product was dissolved in 4 ml of $CH_2Cl_2$, 1 ml of TFA was added and, after 4 h, a further 0.5 ml of TFA was added, and deprotection was carried out at RT for about 10 h. Purification of the deprotected crude product by preparative HPLC afforded 25 mg (27%) of (S)-6-amino-2-{3-[(R)-2-cyclohexyl-1-(2,4-difluorobenzylcarbamoyl)-ethyl]-ureido}-hexanoic acid trifluoroacetate.

The following examples were prepared in analogy to Example 11:

| Example | Formula | LC/MS Method | $R_t$ | $[M+H]^+$ calc. | $[M+H]^+$ found |
|---|---|---|---|---|---|
| 12 | | B | 1.33 min | 461.31 | 461.28 |
| 13 | | B | 1.33 min | 461.31 | 461.29 |
| 14 | | B | 1.50 min | 467.24 | 467.43 |
| 15 | | B | 1.33 min | 447.29 | 447.25 |
| 16 | | B | 1.33 min | 437.31 | 437.27 |

| Example | Formula | LC/MS Method | $R_t$ | $[M+H]^+$ calc. | $[M+H]^+$ found |
|---|---|---|---|---|---|
| 17 | 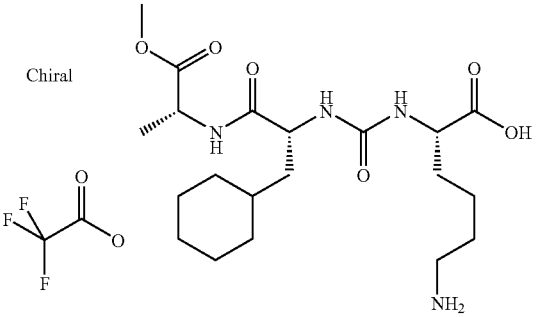 [SMILES: O=C(O)C(F)(F)F ; COC(=O)[C@@H](C)NC(=O)[C@@H](CC1CCCCC1)NC(=O)N[C@@H](CCCCN)C(=O)O] | | | 1H-NMR (400 MHz, DMSO-$d_6$): 13.0-12.0 (br., 1H), 8.38 (d, 1H), 6.34 (d, 1H), 6.20 (d, 1H), 4.30-4.20 (m, 2H), 4.12-4.08 (m, 1H), 3.61 (s, 3H), 2.80-2.70 (m, 2H), 1.80-1.05 (m, 22H), 0.95-0.78 (m, 2H). | |
| 18 | 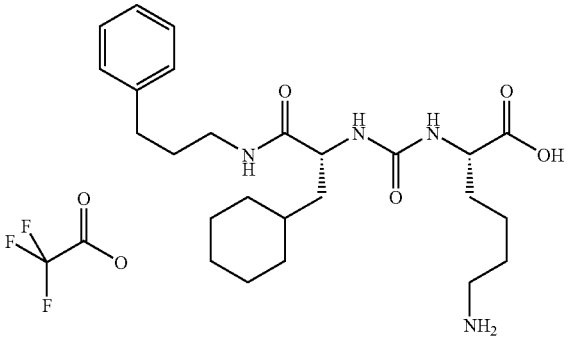 [SMILES: O=C(O)C(F)(F)F ; NCCCC[C@H](NC(=O)N[C@H](CC1CCCCC1)C(=O)NCCCc1ccccc1)C(=O)O] | B | 1.34 min | 461.31 | 461.29 |
| 19 | 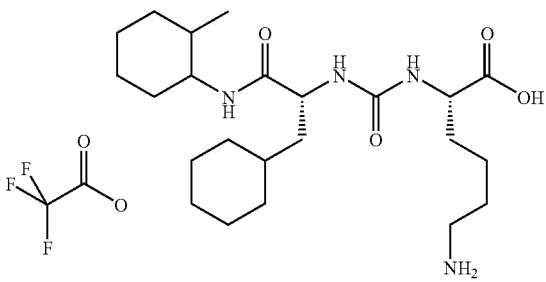 [SMILES: O=C(O)C(F)(F)F ; CC1CCCCC1NC(=O)[C@@H](CC1CCCCC1)NC(=O)N[C@@H](CCCCN)C(=O)O] | B | 1.31 min | 439.32 | 439.31 |
| 20 | 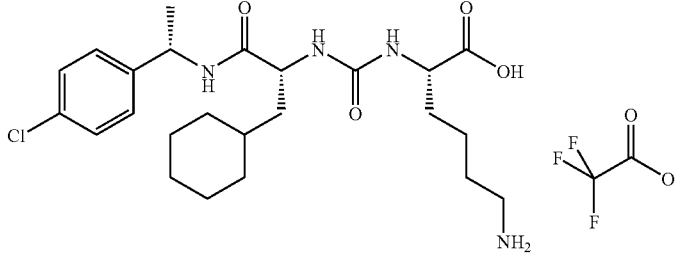 [SMILES: C[C@H](NC(=O)[C@@H](CC1CCCCC1)NC(=O)N[C@@H](CCCCN)C(=O)O)c1ccc(Cl)cc1 ; O=C(O)C(F)(F)F] | B | 1.35 min | 481.25 | 481.23 |

-continued
| Example | Formula | LC/MS Method | $R_t$ | $[M+H]^+$ calc. | $[M+H]^+$ found |
|---|---|---|---|---|---|
| 21 | 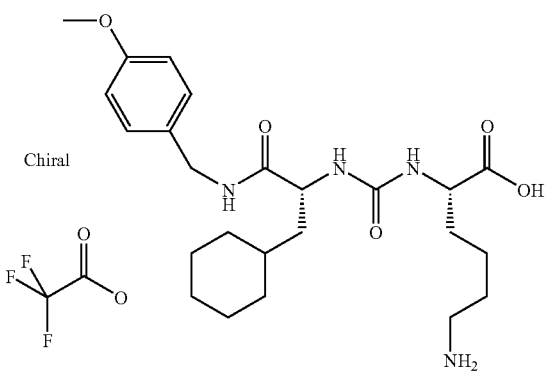 [SMILES: O=C(O)C(F)(F)F ; COc1ccc(CNC(=O)[C@@H](CC2CCCCC2)NC(=O)N[C@@H](CCCCN)C(=O)O)cc1] | B | 1.24 min | 463.29 | 463.28 |
| 22 | 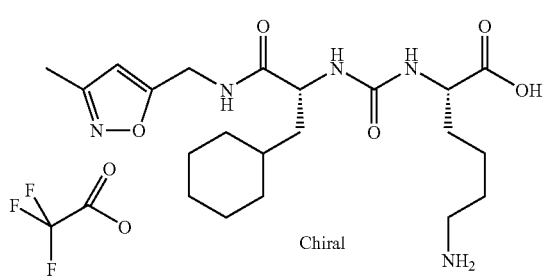 | B | 1.12 min | 438.27 | 438.27 |
| 23 | 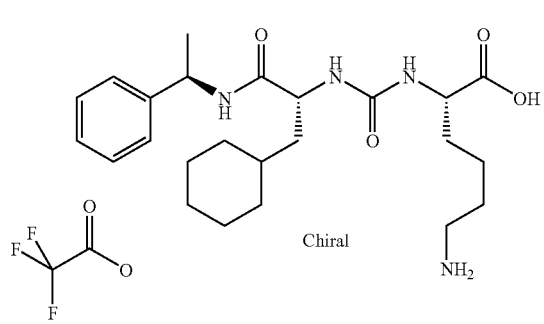 | B | 1.31 min | 447.29 | 447.27 |
| 24 | 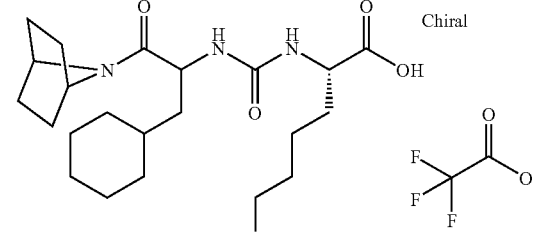 | B | 1.18 min | 423.29 | 423.32 |

-continued
| Example | Formula | LC/MS Method | $R_t$ | $[M+H]^+$ calc. | $[M+H]^+$ found |
|---|---|---|---|---|---|
| 25 | 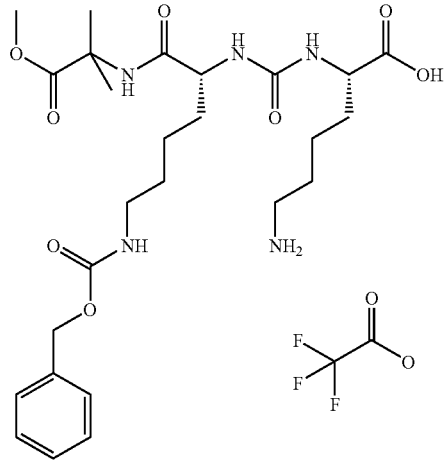 [SMILES: COC(=O)C(C)(C)NC(=O)[C@@H](CCCCNC(=O)OCc1ccccc1)NC(=O)N[C@@H](CCCCN)C(=O)O ; O=C(O)C(F)(F)F] | B | 1.15 min | 552.30 | 552.21 |
| 26 | 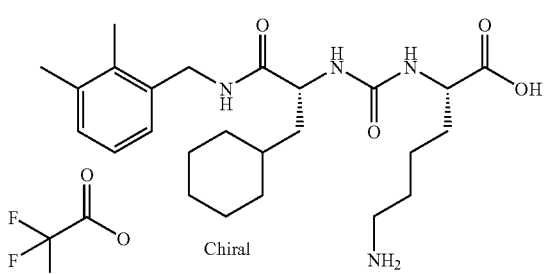 | B | 1.35 min | 461.31 | 461.30 |
| 27 | 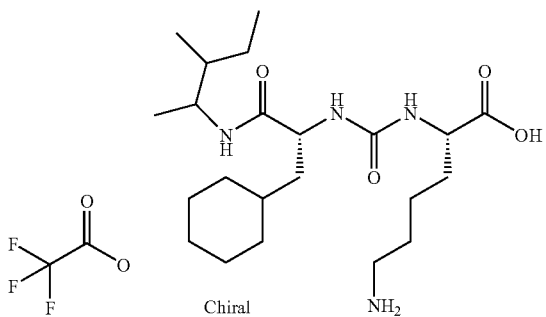 [SMILES: O=C(O)C(F)(F)F ; CCC(C)C(C)NC(=O)[C@@H](CC1CCCCC1)NC(=O)N[C@@H](CCCCN)C(=O)O] | B | 1.33 min | 427.33 | 427.33 |
| 28 | 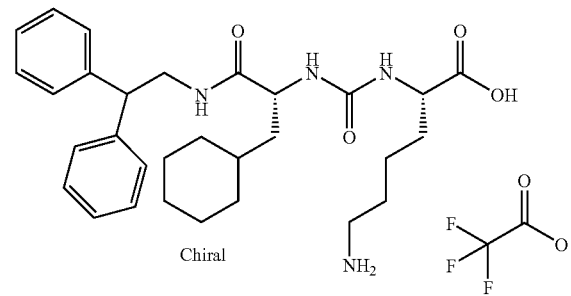 [SMILES: NCCCC[C@H](NC(=O)N[C@H](CC1CCCCC1)C(=O)NCC(c1ccccc1)c1ccccc1)C(=O)O ; O=C(O)C(F)(F)F] | B | 1.46 min | 523.32 | 523.34 |

-continued

| Example | Formula | LC/MS Method | R_t | [M + H]+ calc. | [M + H]+ found |
|---|---|---|---|---|---|
| 29 | | B | 1.23 min | 413.31 | 413.31 |
| 30 | | B | 1.28 min | 491.28 | 491.29 |
| 31 | | B | 1.35 min | 439.32 | 439.32 |
| 32 | | B | 1.35 min | 594.35 | 594.29 |

-continued

| Example | Formula | LC/MS Method | $R_t$ | $[M+H]^+$ calc. | $[M+H]^+$ found |
|---|---|---|---|---|---|
| 33 | | B | 1.33 min | 606.35 | 606.31 |
| 34 | | B | 1.33 min | 570.32 | 570.26 |
| 35 | | B | 1.43 min | 618.32 | 618.24 |

-continued
| Example | Formula | LC/MS Method | $R_t$ | $[M+H]^+$ calc. | $[M+H]^+$ found |
|---|---|---|---|---|---|
| 36 | 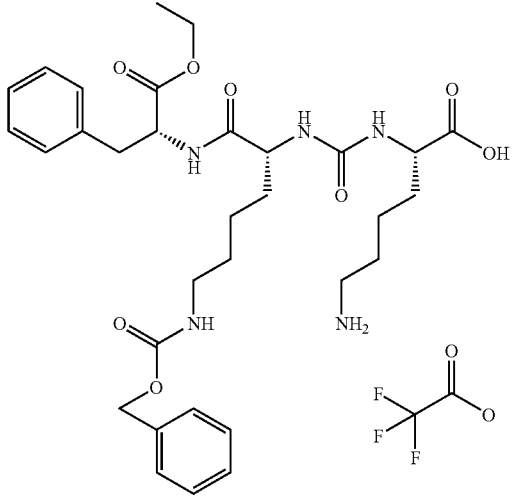 [SMILES: CCOC(=O)[C@@H](Cc1ccccc1)NC(=O)[C@@H](CCCCNC(=O)OCc1ccccc1)NC(=O)N[C@@H](CCCCN)C(=O)O ; O=C(O)C(F)(F)F] | B | 1.37 min | 628.33 | 628.26 |
| 37 | 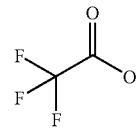 | B | 1.30 min | 580.33 | 580.25 |
| 38 | 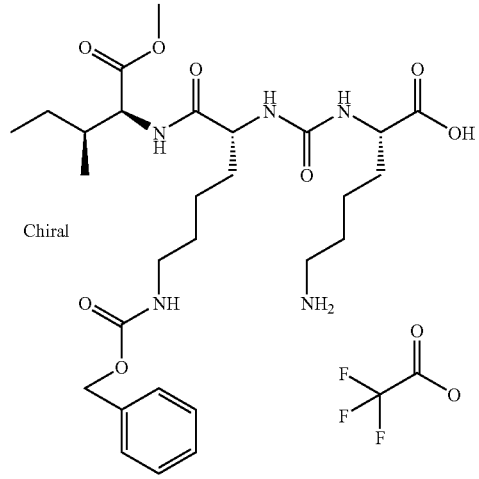 [SMILES: CC[C@H](C)[C@H](NC(=O)[C@@H](CCCCNC(=O)OCc1ccccc1)NC(=O)N[C@@H](CCCCN)C(=O)O)C(=O)OC ; O=C(O)C(F)(F)F] | B | 1.28 min | 580.33 | 580.23 |

| Example | Formula | LC/MS Method | $R_t$ | [M + H]⁺ calc. | [M + H]⁺ found |
|---|---|---|---|---|---|
| 39 | | B | 1.23 min | 578.32 | 578.29 |
| 40 | | B | 1.84 min | 696.39 | 696.40 |
| 41 | | B | 1.33 min | 439.32 | 439.31 |
| 42 | | B | 1.30 min | 548.34 | 548.43 |

-continued
| Example | Formula | LC/MS Method | $R_t$ | $[M + H]^+$ calc. | $[M + H]^+$ found |
|---|---|---|---|---|---|
| 43 | 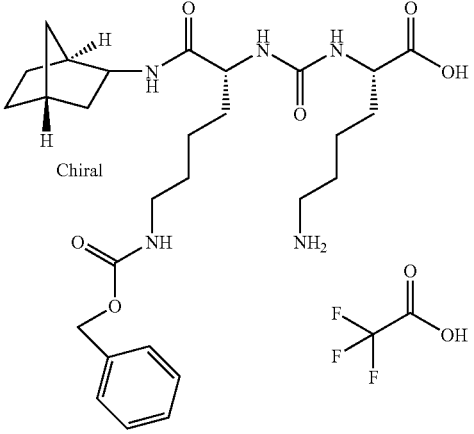 [SMILES: NCCCC[C@H](NC(=O)N[C@H](CCCCNC(=O)OCc1ccccc1)C(=O)NC1C[C@@H]2CC[C@H]1C2)C(=O)O ; O=C(O)C(F)(F)F] | C | 1.45 min | 544.31 | 544.32 $[M - H]^-$ |
| 44 | 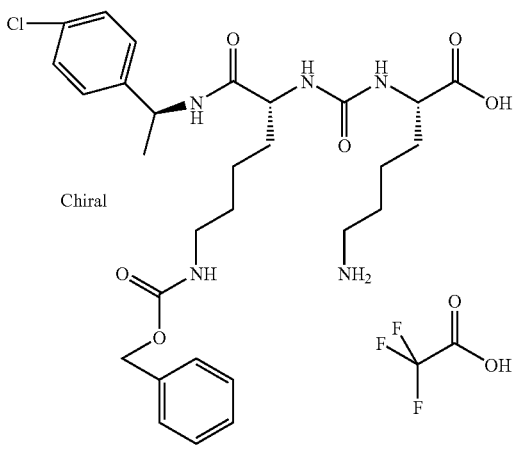 [SMILES: C[C@H](NC(=O)[C@@H](CCCCNC(=O)OCc1ccccc1)NC(=O)N[C@@H](CCCCN)C(=O)O)c1ccc(Cl)cc1 ; O=C(O)C(F)(F)F] | B | 1.37 min | 590.27 | 590.44 |
| 45 | 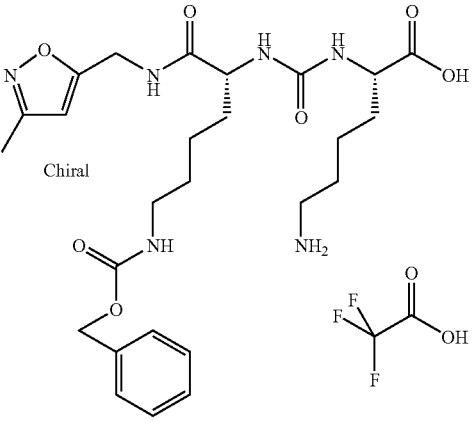 [SMILES: Cc1cc(CNC(=O)[C@@H](CCCCNC(=O)OCc2ccccc2)NC(=O)N[C@@H](CCCCN)C(=O)O)on1 ; O=C(O)C(F)(F)F] | B | 1.12 min | 547.28 | 547.40 |

-continued

| Example | Formula | LC/MS Method | $R_t$ | $[M + H]^+$ calc. | $[M + H]^+$ found |
|---|---|---|---|---|---|
| 46 | | B | 1.18 min | 538.28 | 538.35 |
| 47 | | B | 1.30 min | 556.31 | 556.35 |
| 48 | | B | 1.38 min | 570.32 | 570.47 |
| 49 | | B | 1.29 min | 471.31 | 471.42 |

-continued
| Example | Formula | LC/MS Method | $R_t$ | $[M + H]^+$ calc. | $[M + H]^+$ found |
|---|---|---|---|---|---|
| 50 | 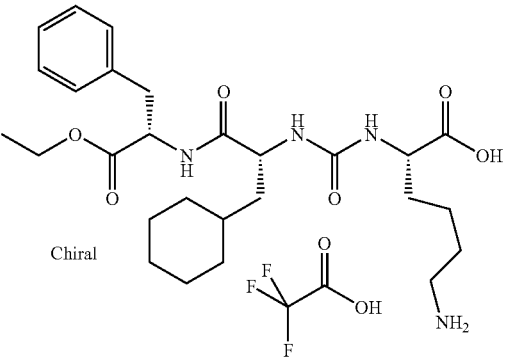 | B | 1.37 min | 519.31 | 519.35 |
| 51 | 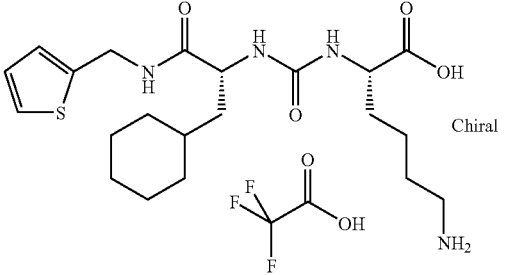 | B | 1.20 min | 439.23 | 439.30 |
| 52 | 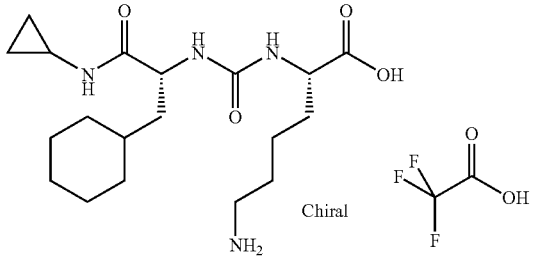 [SMILES: NCCCC[C@H](NC(=O)N[C@H](CC1CCCCC1)C(=O)NC1CC1)C(=O)O ; O=C(O)C(F)(F)F] | B | 1.03 min | 383.26 | 383.33 |
| 53 | 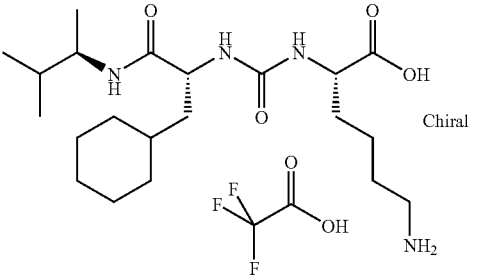 | B | 1.23 min | 413.31 | 413.37 |
| 54 | 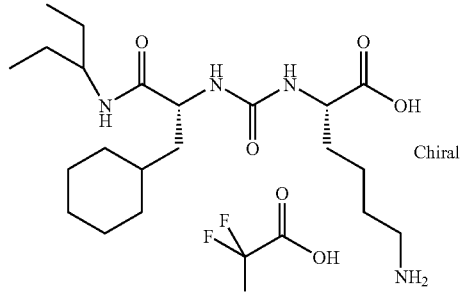 | B | 1.21 min | 413.31 | 413.37 |

-continued

| Example | Formula | LC/MS Method | $R_t$ | $[M+H]^+$ calc. | $[M+H]^+$ found |
|---|---|---|---|---|---|
| 55 | | B | 1.17 min | 411.29 | 411.37 |
| 56 | | B | 1.36 min | 453.34 | 453.40 |
| 57 | | B | 1.29 min | 471.31 | 471.43 |
| 58 | | B | 1.38 min | 576.25 | 576.45 |
| 59 | | B | 1.22 min | 439.23 | 439.31 |

-continued

| Example | Formula | LC/MS Method | R$_t$ | [M + H]$^+$ calc. | [M + H]$^+$ found |
|---|---|---|---|---|---|
| 60 | | B | 1.30 min | 465.28 | 465.36 |
| 61 | | B | 1.35 min | 473.31 | 473.38 |
| 62 | | B | 1.11 min | 385.28 | 385.35 |
| 63 | | B | 1.42 min | 509.31 | 509.36 |

-continued
| Example | Formula | LC/MS Method | $R_t$ | $[M+H]^+$ calc. | $[M+H]^+$ found |
|---|---|---|---|---|---|
| 64 | 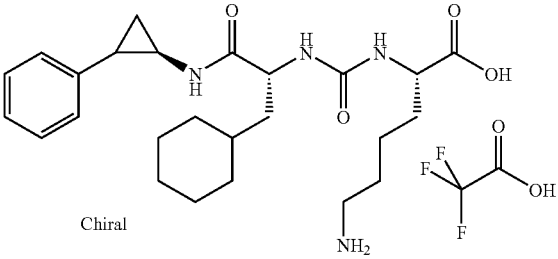 | B | 1.33 min | 459.29 | 459.36 |
| 65 | 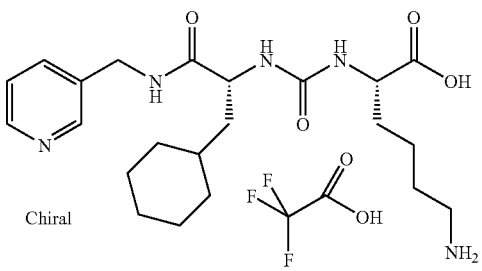 | B | 0.95 min | 434.27 | 434.38 |
| 66 | 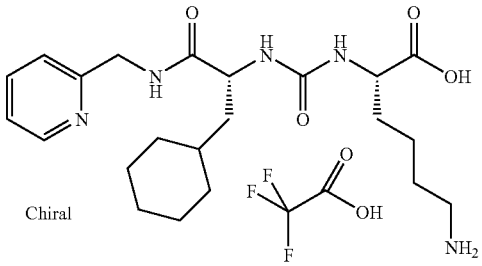 | B | 0.87 min | 434.27 | 434.38 |
| 67 | 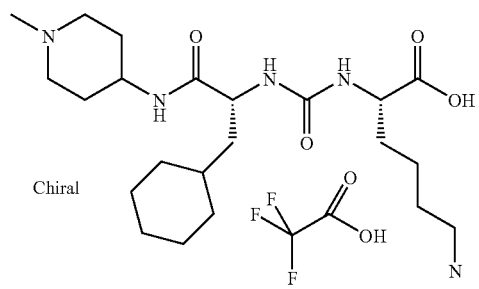 | B | 0.82 min | 440.32 | 440.44 |
| 68 | 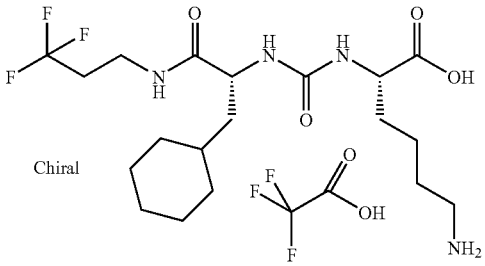 | B | 1.18 min | 439.25 | 439.33 |

-continued
| Example | Formula | LC/MS Method | $R_t$ | $[M + H]^+$ calc. | $[M + H]^+$ found |
|---|---|---|---|---|---|
| 69 | 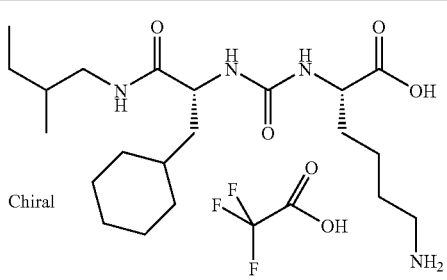 | B | 1.26 min | 413.31 | 413.39 |
| 70 | 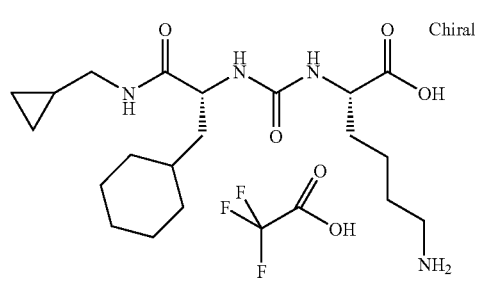 | B | 1.22 min | 397.28 | 397.35 |
| 71 | 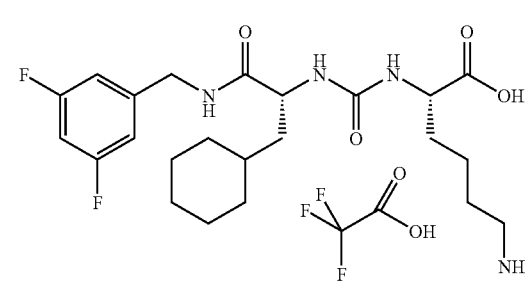 | B | 1.29 min | 469.26 | 469.29 |
| 72 | 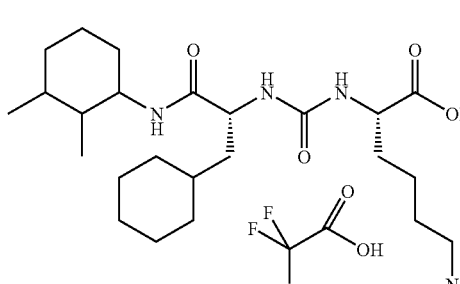 | C | 1.54-1.60 | 451.33 | 451.35 [M − H]⁻ |
| 73 | 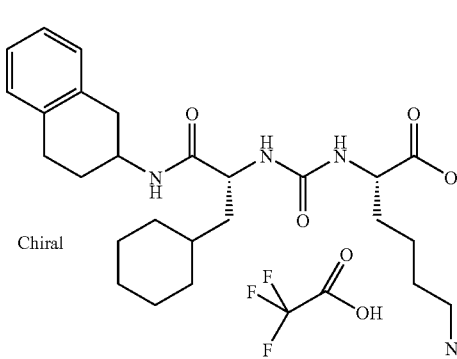 | B | 1.38 min | 473.31 | 473.31 |

-continued
| Example | Formula | LC/MS Method | $R_t$ | $[M+H]^+$ calc. | $[M+H]^+$ found |
|---|---|---|---|---|---|
| 74 | 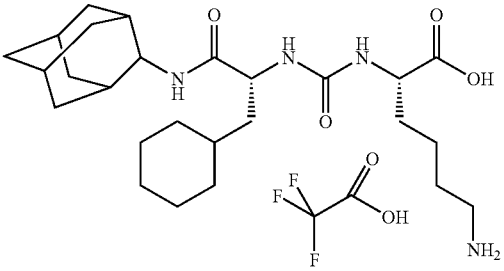 | C | 1.58-1.72 | 475.33 [M−H]⁻ | 475.32 [M−H]⁻ |
| 75 | 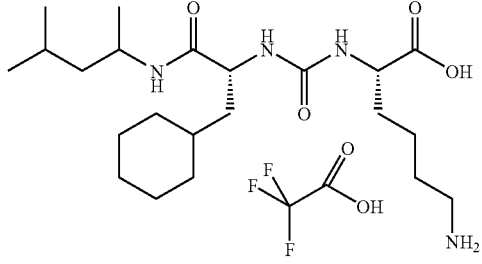 | C | 1.46 min | 425.31 [M−H]⁻ | 425.35 [M−H]⁻ |
| 76 | 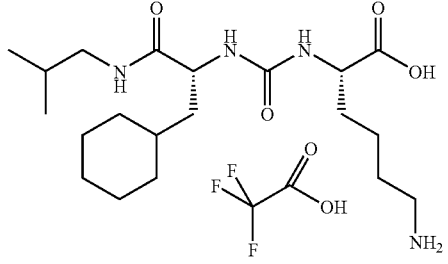 | C | 1.33 min | 397.28 [M−H]⁻ | 397.24 [M−H]⁻ |
| 77 | 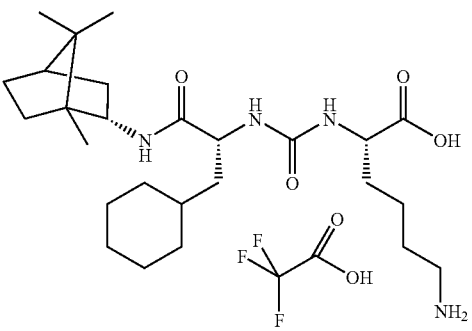 | C | 1.60 min | 477.34 [M−H]⁻ | 477.36 [M−H]⁻ |
| | | 500 MHz-¹H-NMR (d6-DMSO): δ = 7.88 (s, br, 3H), 7.63 (d, 1H), 6.40 (d, 1H), 6.29 (d, 1H), 4.26-4.19 (m, 1H), 4.12-4.07 (m, 1H), 4.03-3.99 (m, 1H), 2.79-2.70 (m, 2H), 2.13-2.07 (m, 1H), 1.78-1.46 (m, 22H), 0.90-0.80 (m, 3H), 0.88 (s, 3H), 0.79 (s, 3H), 0.68 (s, 3H) | | | | |
| 78 | 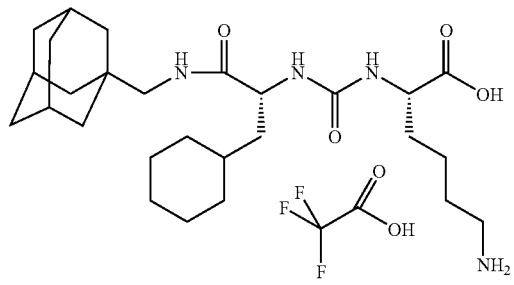 | C | 1.64 min | 489.34 [M−H]⁻ | 489.27 [M−H]⁻ |

-continued

| Example | Formula | LC/MS Method | R_t | [M + H]⁺ calc. | [M + H]⁺ found |
|---|---|---|---|---|---|
| 79 | | C | 1.61 min | 475.32 [M− H]⁻ | 475.25 [M− H]⁻ |
| 80 | | C | 1.34 min | 441.27 [M− H]⁻ | 441.35 [M− H]⁻ |
| 81 | | C | 1.43 min | 423.30 [M− H]⁻ | 423.44 [M− H]⁻ |
| 82 | | B | 0.94 min | 434.28 | 434.28 |
| 83 | | C | 1.28 min | 453.27 [M− H]⁻ | 453.33 [M− H]⁻ |

-continued

| Example | Formula | LC/MS Method | $R_t$ | $[M+H]^+$ calc. | $[M+H]^+$ found |
|---|---|---|---|---|---|
| 84 | | C | 1.72 min | 491.36 $[M-H]^-$ | 491.38 $[M-H]^-$ |
| 85 | | C | 1.55 min | 471.30 $[M-H]^-$ | 471.30 $[M-H]^-$ |
| 86 | | C | 1.68 min | 479.36 $[M-H]^-$ | 479.47 $[M-H]^-$ |
| 87 | | B | 1.15 min | 397.28 | 397.33 |

-continued
| Example | Formula | LC/MS Method | $R_t$ | $[M+H]^+$ calc. | $[M+H]^+$ found |
|---|---|---|---|---|---|
| 88 | 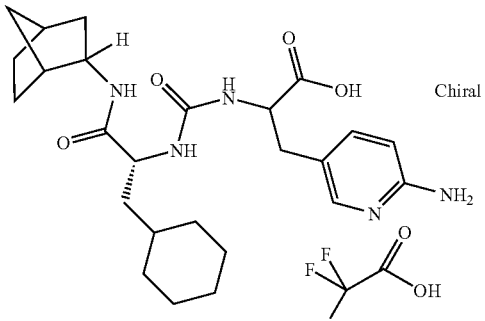 | B | 1.38 min | 472.29 | 472.32 |
| 89 | 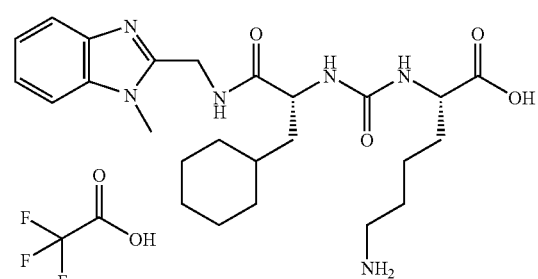 | B | 1.06 min | 487.30 | 487.38 |
| 90 | 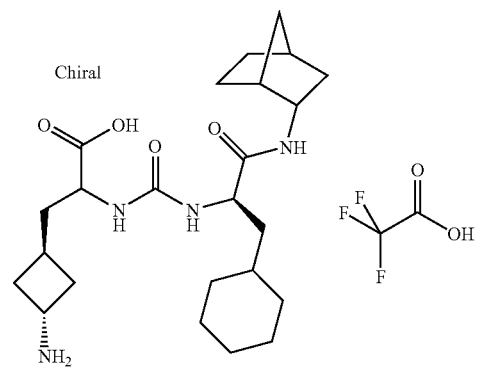 [SMILES: N[C@H]1C[C@H](CC(NC(=O)N[C@H](CC2CCCCC2)C(=O)NC2CC3CCC2C3)C(=O)O)C1 ; O=C(O)C(F)(F)F] | C | 1.48 min | 447.30 $[M-H]^-$ | 447.40 $[M-H]^-$ |
| 91 | 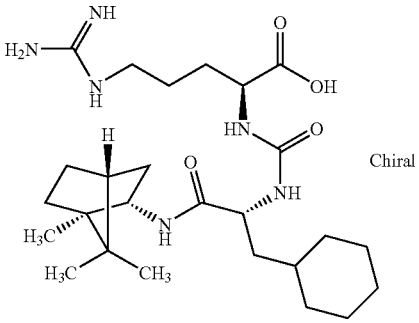 [SMILES: CC1(C)[C@@H]2CC[C@@]1(C)[C@@H](NC(=O)[C@@H](CC1CCCCC1)NC(=O)N[C@@H](CCCNC(=N)N)C(=O)O)C2] | D | 2.13 min | 507.37 | 507.40 |

-continued
| Example | Formula | LC/MS Method | $R_t$ | $[M+H]^+$ calc. | $[M+H]^+$ found |
|---|---|---|---|---|---|
| 92 | 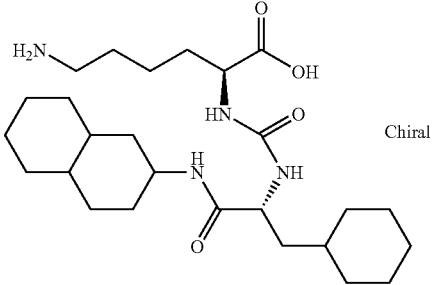 [SMILES: NCCCC[C@H](NC(=O)N[C@H](CC1CCCCC1)C(=O)NC1CCC2CCCCC2C1)C(=O)O] | D | 2.16 min | 479.36 | 479.36 |
| 93 | 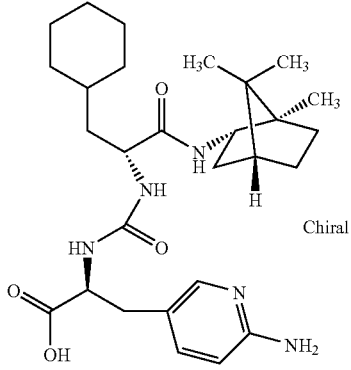 [SMILES: CC1(C)[C@@H]2CC[C@@]1(C)[C@@H](NC(=O)[C@@H](CC1CCCCC1)NC(=O)N[C@@H](Cc1ccc(N)nc1)C(=O)O)C2] | A | 1.21 min | 514.69 | 514.45 |
| 94 | 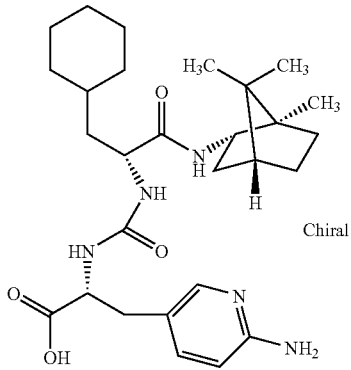 [SMILES: CC1(C)[C@@H]2CC[C@@]1(C)[C@@H](NC(=O)[C@@H](CC1CCCCC1)NC(=O)N[C@H](Cc1ccc(N)nc1)C(=O)O)C2] | A | 1.20 min | 514.69 | 514.45 |
|  |  | 400 MHz-$^1$H-NMR (d6-DMSO): δ = 7.93 (s, br, 2H), 7.78 (d, 1H), 7.72 (s, 1H), 7.68 (d, 1H), 6.91 (d, 1H), 6.42 (d, 1H), 6.23 (d, 1H), 4.34 (dd, 1H), 4.17 (dd, 1H), 4.04-3.97 (m, 1H), 2.93 (dd, 1H), 2.71 (dd, 1H), 2.14-2.05 (m, 1H), 1.71-1.53 (m, 8H), 1.42-1.02 (m, 8H), 0.90-0.77 (m, 3H), 0.88 (s, 3H), 0.82 (s, 3H), 0.68 (s, 3H) | | | | |
| 95 | 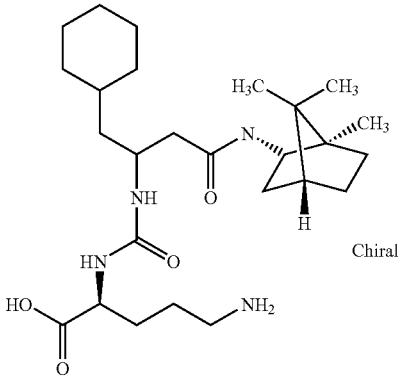 | A | 1.13 min | 479.69 | 479.45 |

-continued
| Example | Formula | LC/MS Method | $R_t$ | $[M + H]^+$ calc. | $[M + H]^+$ found |
|---|---|---|---|---|---|
| 96 | 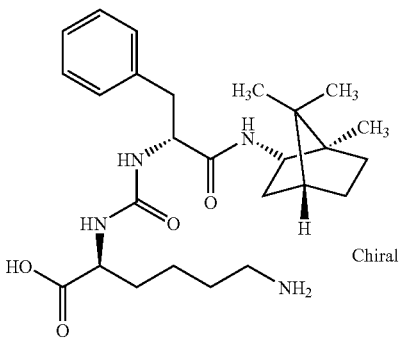 | A | 1.10 min | 473.64 | 473.45 |
| 97 | 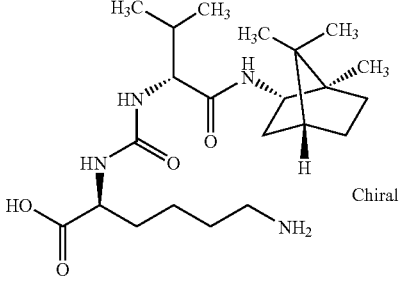 [SMILES: CC(C)[C@@H](NC(=O)N[C@@H](CCCCN)C(=O)O)C(=O)N[C@H]1C[C@H]2CC[C@]1(C)C2(C)C] | A | 1.01 min | 425.35 | 425.60 |
| 98 | 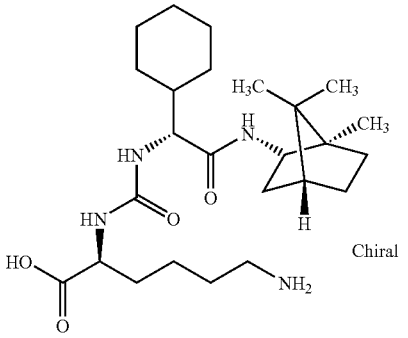 | A | 1.11 min | 465.66 | 465.40 |
| 99 | 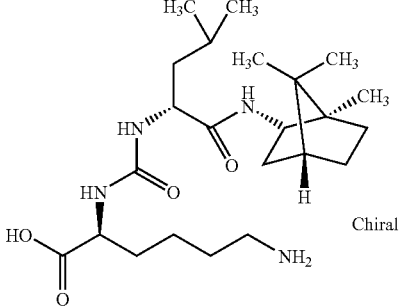 | A | 1.05 min | 439.62 | 439.25 |

-continued
| Example | Formula | LC/MS Method | $R_t$ | $[M+H]^+$ calc. | $[M+H]^+$ found |
|---|---|---|---|---|---|
| 100 | 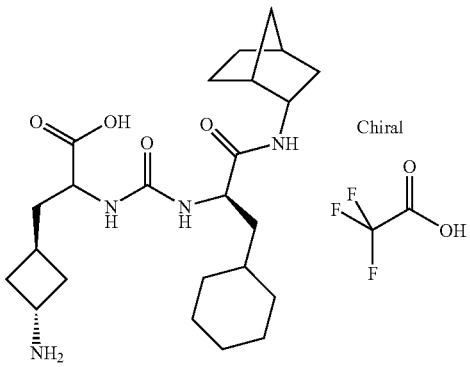 [SMILES: N[C@H]1C[C@H](CC(NC(=O)N[C@H](CC2CCCCC2)C(=O)NC2CC3CCC2C3)C(=O)O)C1 ; O=C(O)C(F)(F)F] | A | 1.48 min | 447.60 | 447.40 |
| 101 | 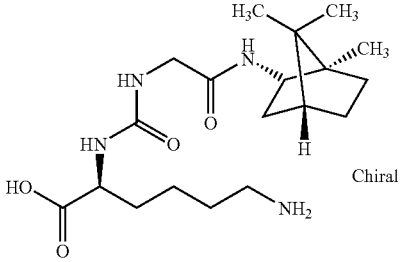 | A | 0.90 min | 383.25 | 383.25 |
| 102 | 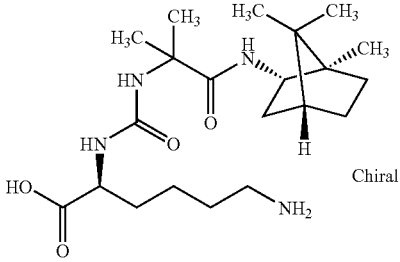 [SMILES: CC(C)(NC(=O)N[C@@H](CCCCN)C(=O)O)C(=O)N[C@H]1C[C@H]2CC[C@]1(C)C2(C)C] | A | 0.93 min | 411.57 | 411.25 |
| 103 | 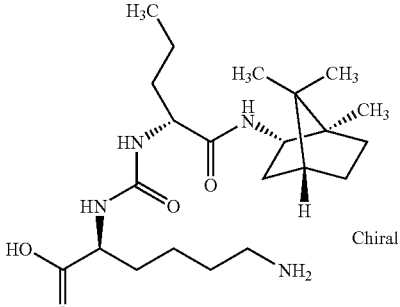 | A | 1.04 min | 425.60 | 425.25 |

| Example | Formula | LC/MS Method | $R_t$ | $[M+H]^+$ calc. | $[M+H]^+$ found |
|---|---|---|---|---|---|
| 104 | 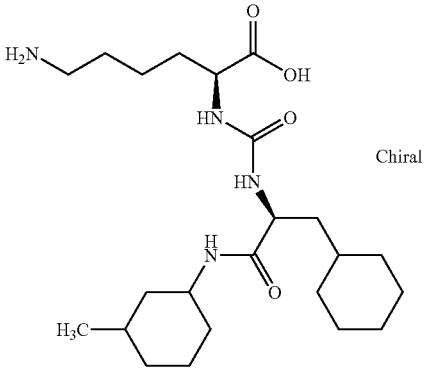 [SMILES: CC1CCCC(NC(=O)[C@H](CC2CCCCC2)NC(=O)N[C@@H](CCCCN)C(=O)O)C1] | B | 1.35 min | 439.33 | 439.52 |
| 105 | 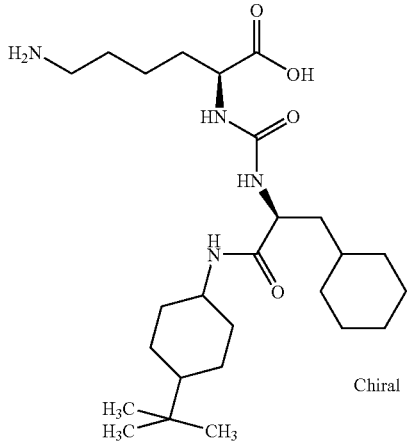 [SMILES: CC(C)(C)C1CCC(NC(=O)[C@H](CC2CCCCC2)NC(=O)N[C@@H](CCCCN)C(=O)O)CC1] | B | 1.56 min | 481.38 | 481.58 |
| 106 | 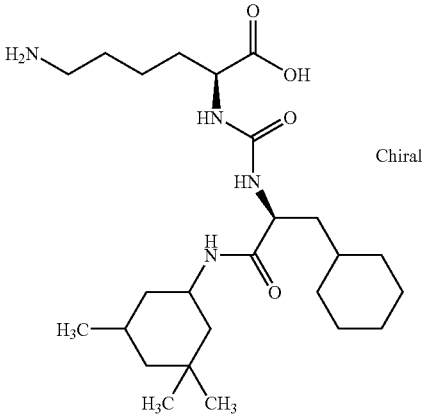 [SMILES: CC1CC(NC(=O)[C@H](CC2CCCCC2)NC(=O)N[C@@H](CCCCN)C(=O)O)CC(C)(C)C1] | B | 1.47 min | 467.36 | 467.56 |
| 107 | 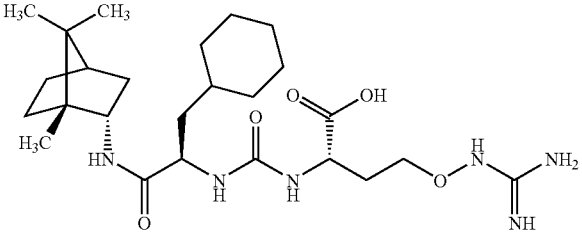 [SMILES: CC1(C)C2CC[C@@]1(C)[C@@H](NC(=O)[C@@H](CC1CCCCC1)NC(=O)N[C@@H](CCONC(=N)N)C(=O)O)C2] | B | 1.51 min | 509.67 | 509.44 |

-continued
| Example | Formula | LC/MS Method | $R_t$ | [M + H]$^+$ calc. | [M + H]$^+$ found |
|---|---|---|---|---|---|
| 108 | 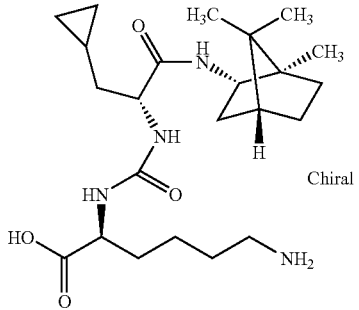 [SMILES: CC1(C)[C@@H]2CC[C@@]1(C)[C@@H](NC(=O)[C@@H](CC1CC1)NC(=O)N[C@@H](CCCCN)C(=O)O)C2] Chiral | A | 1.05 min | 437.61 | 437.25 |
| 109 | 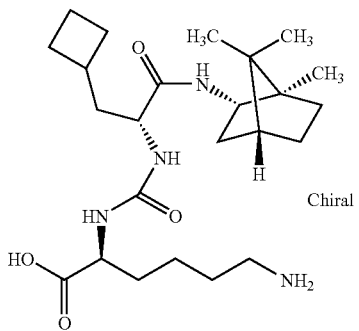 [SMILES: CC1(C)[C@@H]2CC[C@@]1(C)[C@@H](NC(=O)[C@@H](CC1CCC1)NC(=O)N[C@@H](CCCCN)C(=O)O)C2] Chiral | A | 1.10 min | 451.63 | 451.25 |
| 110 | 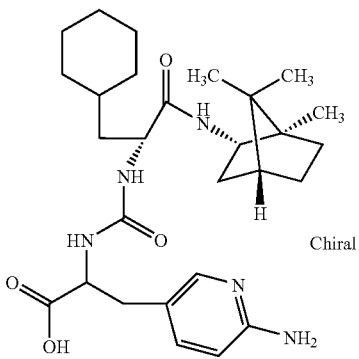 [SMILES: CC1(C)[C@@H]2CC[C@@]1(C)[C@@H](NC(=O)[C@@H](CC1CCCCC1)NC(=O)NC(Cc1ccc(N)nc1)C(=O)O)C2] Chiral | A | 1.22 min | 514.69 | 514.25 |
| 111 | 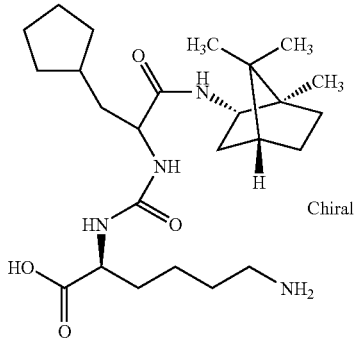 [SMILES: CC1(C)[C@@H]2CC[C@@]1(C)[C@@H](NC(=O)C(CC1CCCC1)NC(=O)N[C@@H](CCCCN)C(=O)O)C2] Chiral | A | 1.13 min | 465.66 | 465.30 |

-continued
| Example | Formula | LC/MS Method | $R_t$ | $[M+H]^+$ calc. | $[M+H]^+$ found |
|---|---|---|---|---|---|
| 112 | 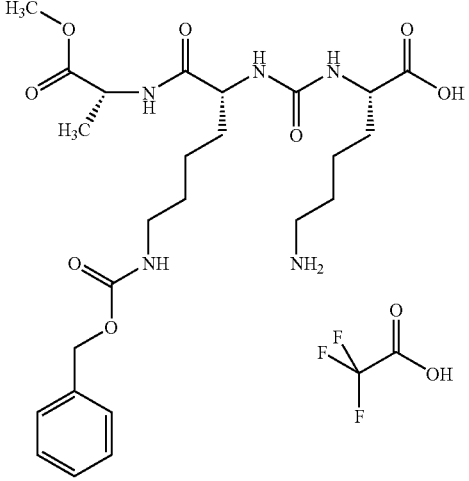 [SMILES: COC(=O)[C@@H](C)NC(=O)[C@@H](CCCCNC(=O)OCc1ccccc1)NC(=O)N[C@@H](CCCCN)C(=O)O ; O=C(O)C(F)(F)F] | B | 1.18 min | 538.63 | 538.35 |
| 113 | 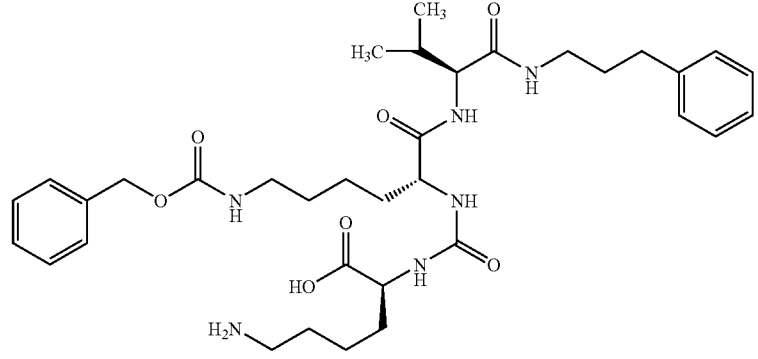 [SMILES: CC(C)[C@H](NC(=O)[C@@H](CCCCNC(=O)OCc1ccccc1)NC(=O)N[C@@H](CCCCN)C(=O)O)C(=O)NCCCc1ccccc1] | C | 1.60 min | 669.85 | 669.57 |
| 114 | 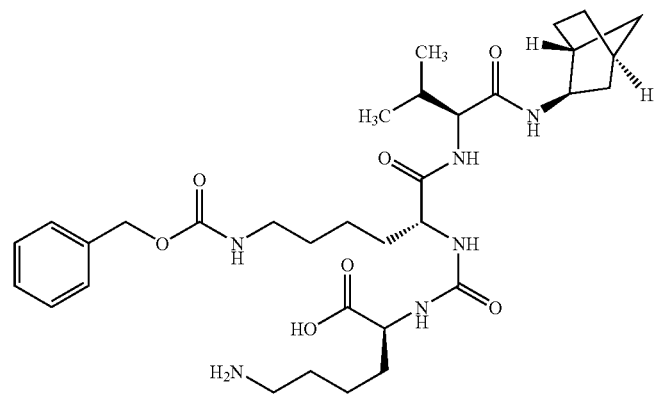 [SMILES: CC(C)[C@H](NC(=O)[C@@H](CCCCNC(=O)OCc1ccccc1)NC(=O)N[C@@H](CCCCN)C(=O)O)C(=O)N[C@@H]1C[C@H]2CC[C@@H]1C2] | C | 1.53 min | 645.83 | 645.52 |

-continued

| Example | Formula | LC/MS Method | $R_t$ | $[M+H]^+$ calc. | $[M+H]^+$ found |
|---|---|---|---|---|---|
| 115 | | B | 1.53 min | 645.83 | 645.52 |
| 116 | | C | 1.38 min | 591.73 | 591.45 |
| 117 | | C | 1.60 min | 727.89 | 727.50 |
| 118 | | C | 1.53 min | 679.84 | 679.53 |

-continued

| Example | Formula | LC/MS Method | $R_t$ | $[M+H]^+$ calc. | $[M+H]^+$ found |
|---|---|---|---|---|---|
| 119 | | C | 1.61 min | 690.27 | 689.48 690.26 |
| 120 | | C | 1.57 min | 647.84 | 647.53 |
| 121 | | C | 1.51 min | 621.80 | 621.54 |
| 122 | | C | 1.53 min | 655.82 | 655.54 |

-continued
| Example | Formula | LC/MS Method | R$_t$ | [M + H]$^+$ calc. | [M + H]$^+$ found |
|---|---|---|---|---|---|
| 123 | 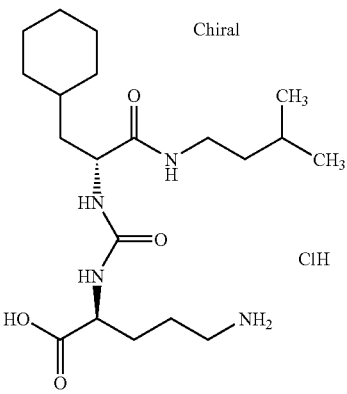 [SMILES: CC(C)CCNC(=O)[C@@H](CC1CCCCC1)NC(=O)N[C@@H](CCCN)C(=O)O ; Cl] | A | 1.01 min | 399.56 | 399.25 |
| 124 | 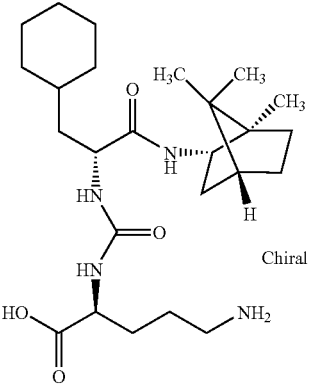 [SMILES: CC1(C)[C@@H]2CC[C@@]1(C)[C@@H](NC(=O)[C@@H](CC1CCCCC1)NC(=O)N[C@@H](CCCN)C(=O)O)C2] | A | 1.17 min | 465.66 | 465.35 |
| 125 | 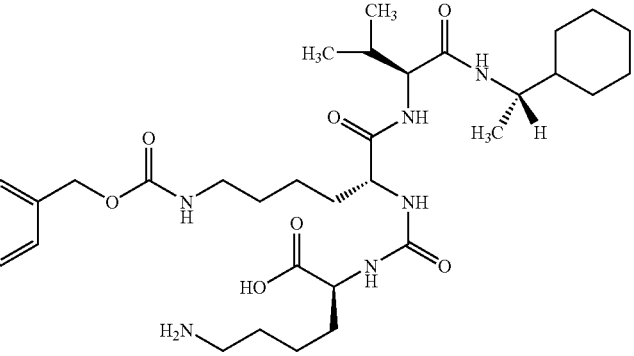 | C | 1.61 min | 661.87 | 661.55 |
| 126 | 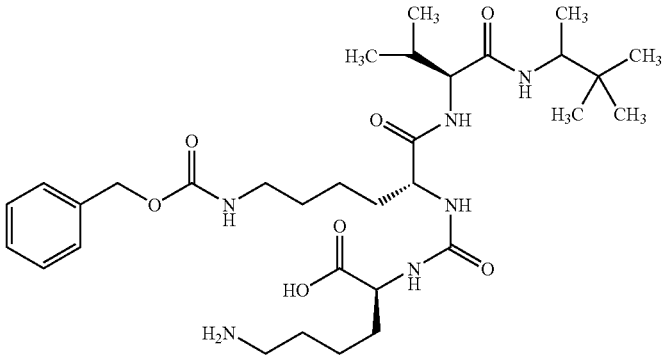 [SMILES: CC(C)[C@H](NC(=O)[C@@H](CCCCNC(=O)OCc1ccccc1)NC(=O)N[C@@H](CCCCN)C(=O)O)C(=O)NC(C)C(C)(C)C] | C | 1.54 min | 635.83 | 635.57 |

-continued

| Example | Formula | LC/MS Method | $R_t$ | $[M+H]^+$ calc. | $[M+H]^+$ found |
|---|---|---|---|---|---|
| 127 | 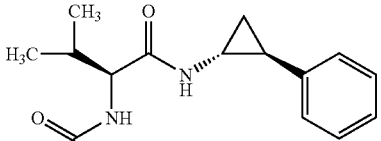 | C | 1.57 min | 667.83 | 667.50 |
| 128 | 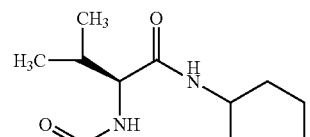 | C | 1.55 min | 647.84 | 647.53 |
| 129 | 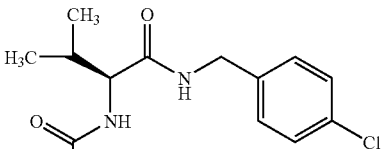 | C | 1.57 min | 676.24 | 675.45<br>677.46 |

Example 130

(S)-6-Amino-2-{3-[(R)-5-benzyloxycarbonylamino-1-((S)-1-carbamoyl-2-methyl-propylcarbamoyl)-pentyl]-ureido}-hexanoic acid

Example 130a

Benzyl[(R)-5-tert-butoxycarbonylamino-5-((S)-1-carbamoyl-2-methyl-propylcarbamoyl)-pentyl]-carbamate N-Methylmorpholine (0.87 ml, 7.9 mmol), 1-hydroxybenzotriazole (0.46 g, 3.41 mmol) and 1-(3-dimethylaminopropyl)-3-ethylcarbodiimide hydrochloride (0.65 g, 3.41 mmol) were added in this sequence to a solution of commercially available (R)-6-benzyloxycarbonylamino-2-tert-butoxycarbonylamino-hexanoic acid (1 g, 2.63 mmol) and commercially available (S)-2-amino-3-methylbutyramide hydrochloride (0.40 g, 2.63 mmol) in 12 ml of $CH_2Cl_2$ and 4 ml of DMF, and the mixture was stirred at RT for about 14 h. Flash chromatography (gradient heptane/AcOEt to $CH_2Cl_2$/MeOH) afforded 1 g of the product (79%).

Example 130b

Benzyl[(R)-5-amino-5-((S)-1-carbamoyl-2-methyl-propylcarbamoyl)-pentyl]-carbamate hydrochloride A solution of benzyl[(R)-5-tert-butoxycarbonylamino-5-((S)-1-carbamoyl-2-methyl-propylcarbamoyl)-pentyl]-carbamate (1 g, 2.09 mmol) in 30 ml of $CH_2Cl_2$ was mixed with 5 ml of $H_2O$ and 5 ml of conc. HCl/$H_2O$ and heated at 40° C. until the Boc protective group was completely eliminated.

Extraction with H₂O/CH₂Cl₂, drying of the organic phase over MgSO₄ and evaporation afforded 230 mg (27%) of the product.

Example 130c tert-Butyl(S)-2-{3-[(R)-5-benzyloxycarbonylamino-1-((S)-1-carbamoyl-2-methyl-propylcarbamoyl)-pentyl]-ureido}-6-tert-butoxycarbonylamino-hexanoate trifluoroacetate Commercially available tert-butyl(S)-2-amino-6-tert-butoxycarbonylaminohexanoate hydrochloride (89 mg, 0.26 mmol) was mixed in 4 ml of DMF with NEt₃ (0.12 ml, 0.53 mmol) and 1,1'-carbonyldiimidazole (43 mg, 0.26 mmol) and stirred at RT for 1 h. Then benzyl[(R)-5-amino-5-((S)-1-carbamoyl-2-methylpropylcarbamoyl)-pentyl]-carbamate hydrochloride (100 mg, 0.24 mmol) was added and the mixture was heated at 80° C. until the imidazolide formed as intermediate was completely converted. Preparative HPLC afforded 76 mg (39%) of tert-butyl(S)-2-{3-[(R)-5-benzyloxycarbonylamino-1-((S)-1-carbamoyl-2-methylpropylcarbamoyl)-pentyl]-ureido}-6-tert-butoxycarbonylaminohexanoate trifluoroacetate.

Example 130d (S)-6-Amino-2-{3-[(R)-5-benzyloxycarbonylamino-1-((S)-1-carbamoyl-2-methyl-propylcarbamoyl)-pentyl]-ureido}-hexanoic acid trifluoroacetate tert-Butyl(S)-2-{3-[(R)-5-benzyloxycarbonylamino-1-((S)-1-carbamoyl-2-methyl-propylcarbamoyl)-pentyl]-ureido}-6-tert-butoxycarbonylaminohexanoate trifluoroacetate (37 mg, 0.045 mmol) was dissolved in 5 ml of CH₂Cl₂ and 1 ml of TFA and stirred at RT for 14 h. Preparative HPLC afforded 21 mg (70%) of (S)-6-amino-2-{3-[(R)-5-benzyloxycarbonylamino-1-((S)-1-carbamoyl-2-methyl-propylcarbamoyl)-pentyl]-ureido}-hexanoic acid trifluoroacetate.

LC/MS: $R_t$ (min)=1.17 calc.: $[M+H]^+$=551.32, found: 551.31 (method B).

The following examples were prepared in analogy to Example 130:

| Example | Formula | LC/MS Method $R_t$ | $[M+H]^+$ calc. | $[M+H]^+$ found |
|---|---|---|---|---|
| 131 | 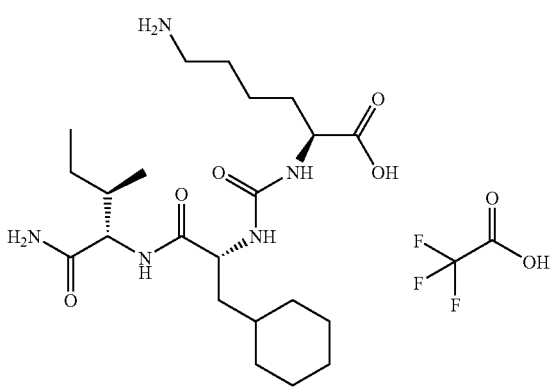 [SMILES: CC[C@@H](C)[C@H](NC(=O)[C@@H](CC1CCCCC1)NC(=O)N[C@@H](CCCCN)C(=O)O)C(N)=O ; O=C(O)C(F)(F)F] | B    1.24 min | 456.31 | 456.30 |
| 132 | 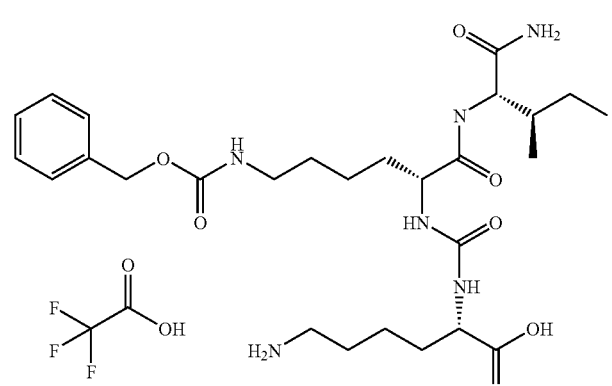 | B    1.18 min | 565.33 | 565.31 |

-continued

| Example | Formula | LC/MS Method | $R_t$ | $[M+H]^+$ calc. | $[M+H]^+$ found |
|---|---|---|---|---|---|
| 133 | | B | 1.36 min | 620.36 | 620.30 |
| 134 | | B | 1.43 min | 752.39 | 752.27 |
| 135 | | B | 1.33 min | 576.37 | 576.35 |

-continued

| Example | Formula | LC/MS Method | $R_t$ | $[M+H]^+$ calc. | $[M+H]^+$ found |
|---|---|---|---|---|---|
| 136 | | B | 1.35 min | 604.37 | 604.33 |
| 137 | | B | 1.16 min | 541.37 | 541.34 |
| 138 | | B | 1.19 min | 593.34 | 593.37 |

-continued
| Example | Formula | LC/MS Method | $R_t$ | $[M + H]^+$ calc. | $[M + H]^+$ found |
|---|---|---|---|---|---|
| 139 | 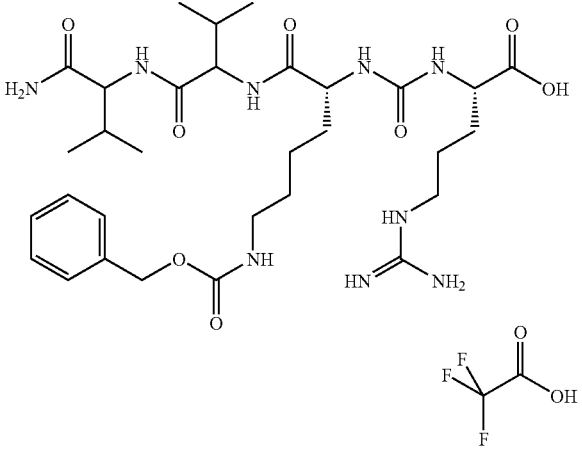 [SMILES: CC(C)C(NC(=O)C(NC(=O)[C@@H](CCCCNC(=O)OCc1ccccc1)NC(=O)N[C@@H](CCCNC(=N)N)C(=O)O)C(C)C)C(N)=O ; O=C(O)C(F)(F)F] | B | 1.18 min | 678.39 | 678.44 |
| 140 | 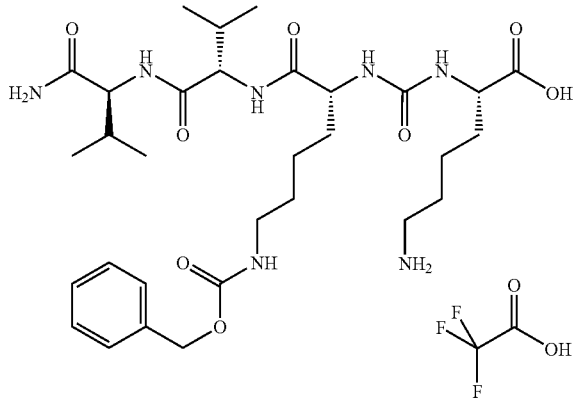 [SMILES: CC(C)[C@H](NC(=O)[C@@H](NC(=O)[C@@H](CCCCNC(=O)OCc1ccccc1)NC(=O)N[C@@H](CCCCN)C(=O)O)C(C)C)C(N)=O ; O=C(O)C(F)(F)F] | B | 1.20 min | 650.38 | 650.40 |
| 141 | 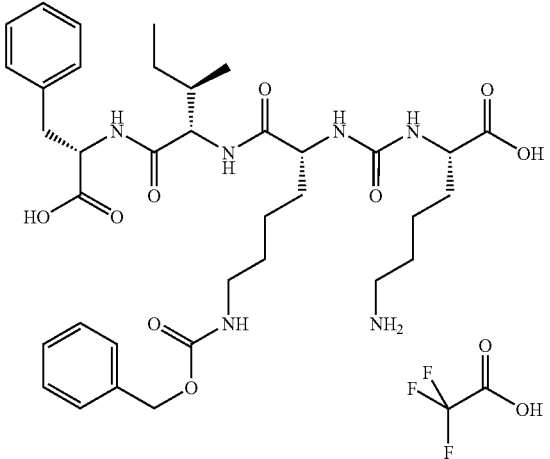 [SMILES: CC[C@@H](C)[C@H](NC(=O)[C@@H](CCCCNC(=O)OCc1ccccc1)NC(=O)N[C@@H](CCCCN)C(=O)O)C(=O)N[C@@H](Cc1ccccc1)C(=O)O ; O=C(O)C(F)(F)F] | B | 1.34 min | 713.38 | 713.39 |

-continued

| Example | Formula | LC/MS Method $R_t$ | $[M + H]^+$ calc. | $[M + H]^+$ found |
|---|---|---|---|---|
| 142 | | B   1.16 min | 565.33 | 565.35 |
| 142a | | D   2.86 min | 497.32 | 497.23 |
| 142b | | D   2.77 min | 529.31 | 529.15 |

Example 143

(S)-6-Amino-2-(3-{(S)-1-[(S)-1-((S)-1-methoxycarbonyl-2-methyl-propylcarbamoyl)-2-methyl-propylcarbamoyl]-2-phenyl-ethyl}-sulfamidyl)-hexanoic acid

Example 143a

Methyl(S)-2-((S)-2-amino-3-methylbutyrylamino)-3-methylbutyrate 600 mg (1.65 mmol) of commercially available methyl(S)-2-((S)-2-benzyloxycarbonyl-amino-3-methylbutyrylamino)-3-methylbutyrate (Z-Val-Val-OMe) was dissolved in 10 ml of methanol, mixed with 20 mg of palladium on carbon (10%) and stirred under a hydrogen atmosphere (1 bar) at RT for 2 h. The reaction mixture was filtered and concentrated and afforded the title compound quantitatively.

LC/MS: $R_t$(min) 0.85; calc.: $[M+H]^+$ 231.17 found: 231.16 (method B).

Example 143b

Methyl(S)-2-[(S)-2-((S)-2-benzyloxycarbonylamino-3-phenyl-propionylamino)-3-methylbutyrylamino]-3-methylbutyrate 247 mg of Z-Phe-OH (0.825 mmol, 1 eq) were dissolved in 10 ml of dry DMF at 0° C. under argon. Then 56 mg of 1-hydroxybenzotriazole (0.5 eq), 221 mg of 1-ethyl-3-(dimethylaminopropyl)carbodiimide hydrochloride (1.4 eq) and 346 μl of Hünig's base (2.4 eq) were added, and the mixture was stirred for 30 min. 190 mg of the compound from Example 143a) were then added, and the mixture was stirred at RT for 20 h. The reaction mixture was mixed with 50 ml of saturated NaHCO$_3$ solution and extracted with ethyl acetatet (2×30 ml). The organic phase was dried over Na$_2$SO$_4$, filtered and concentrated. The crude product was chromatographed on silica gel with heptane/ethyl acetate mixtures. 314 mg of the desired compound were obtained.

LC/MS: R$_t$(min) 1.85; calc.: [M+H]$^+$ 512.28 found 512.36 (method B).

Example 143c

Methyl(S)-2-[(S)-2-((S)-2-amino-3-phenyl-propionylamino)-3-methyl-butyrylamino]-3-methylbutyrate Z deprotection of Z-Phe-Val-Val-OMe to give Phe-Val-Val-OMe was carried out as described in 143a) and afforded 247 mg of the title compound.

LC/MS: R$_t$(min) 1.09; calc.: [M+H]$^+$ 378.24 found 378.33 (method B).

Example 143d

2-Oxooxazolidine-3-sulfonyl chloride

A solution of 1.13 ml of 2-bromoethanol (15.9 mmol, 1.0 eq) in dichloromethane (20 ml) was slowly added to a solution of 2.25 g of chlorosulfonyl isocyanate (15.9 mmol, 1.0 eq) in dichloromethane (100 ml) under argon at 0° C. in such a way that the temperature did not exceed 10° C. After the addition was complete, stirring was continued at 0° C. for 30 min. The product obtained in this way was directly reacted further in the next step.

Example 143e tert-Butyl(S)-6-tert-butoxycarbonylamino-2-(2-oxo-oxazolidine-3-sulfonylamino)-hexanoate A suspension of 5.39 g of H-Lys(Boc)-OtBu hydrochloride (15.9 mmol, 1.0 eq) and 7.1 ml of triethylamine (50.9 mmol, 3.2 eq) in dichloromethane (70 ml) was added to the solution obtained in Example 143d), in such a way that the temperatures did not exceed 10° C. After the addition was complete, the mixture was allowed to reach RT and was stirred for a further 2 h. The reaction mixture was then mixed with 200 ml of 0.2 M hydrochloride acid, and the organic phase was separated off and washed with 100 ml of 0.2 M hydrochloric acid and concentrated. 5.5 g of the desired material were obtained as a colorless oil, which crystallized on standing.

LC/MS: R$_t$(min) 1.76; calc.: [M+H]$^+$ 452.14 found 452.18 (method B).

Example 143f tert-Butyl(S)-6-tert-butoxycarbonylamino-2-(3-{(S)-1-[(S)-1-((S)-1-methoxycarbonyl-2-methyl-propylcarbamoyl)-2-methyl-propylcarbamoyl]-2-phenyl-ethyl}-sulfamidyl)-hexanoate 240 mg of Phe-Val-Val-OMe (compound from Example 143c), 0.636 mmol, 1 eq) were dissolved with 345 mg of the compound from Example 143e) in 7 ml of acetonitrile, and 106 µl of triethylamine were added. The reaction mixture was stirred at 80° C. for 20 h and, after cooling, evaporated. The crude product was purified by chromatography on silica gel with heptane/ethyl acetate mixtures as mobile phase. 275 mg of the title compound were obtained.

LC/MS: R$_t$(min) 1.733; calc.: [M+H]$^+$ 742.41 found 742.35 (method A).

Example 143 g (S)-6-Amino-2-(3-{(S)-1-[(S)-1-((S)-1-methoxycarbonyl-2-methyl-propylcarbamoyl)-2-methyl-propylcarbamoyl]-2-phenyl-ethyl}-sulfamidyl)-hexanoic acid A solution of 270 mg of the compound from Example 143f) in 4 ml of dichloromethane/TFA (1:1, v/v) was stirred at RT for 2 h and then evaporated. The residue was purified by preparative HPLC and afforded 131 mg of the title compound as trifluoroacetate.

LC-MS: R$_t$(min) 1.16; calc.: [M+H]$^+$ 586.29 found 586.39 (method B).

Example 144

(S)-6-Amino-2-{3-[(R)-1-(bicyclo[2.2.1]hept-2-yl-carbamoyl)-2-cyclohexyl-ethyl]-sulfamidyl}-hexanoic acid The title compound was in analogy to Example 143 employing a commercially available endo-norborbonylamine instead of the dipeptide in Example 143c).

LC-MS: R$_t$(min) 1.34; calc.: [M+H]$^+$ 473.28 found 473.36 (method B).

Example 145

(S)-6-Amino-2-[3-((S)-1-cyclohexylcarbamoyl-2-phenyl-ethyl)-sulfamidyl]-hexanoic acid The title compound was in analogy to Example 143 employing a commercially available cyclohexylamine instead of the dipeptide in Example 143c).

LC-MS: R$_t$(min) 1.20; calc.: [M+H]$^+$ 455.24 found 455.33 (method B).

The following examples were prepared in analogy to Example 143:
| Example | Formula | LC/MS Method | $R_t$ | $[M + H]^+$ calc. | $[M + H]^+$ found |
|---|---|---|---|---|---|
| 146 | 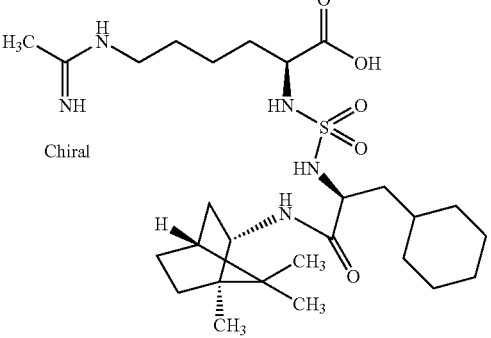 | D | 2.20 | 556.35 | 556.36 |
| 147 | 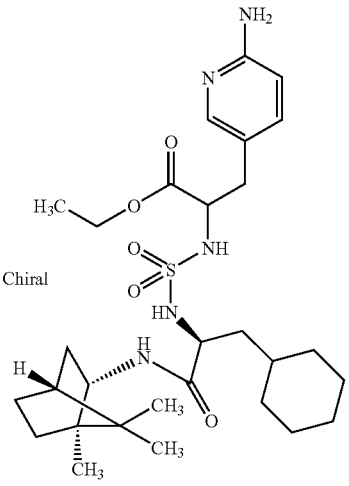 [SMILES: CCOC(=O)C(Cc1ccc(N)nc1)NS(=O)(=O)N[C@@H](CC1CCCCC1)C(=O)N[C@H]1C[C@H]2CC[C@]1(C)C2(C)C] | D | 2.40 | 578.34 | 578.41 |
| 148 | 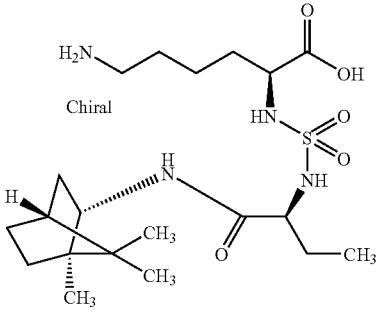 [SMILES: CC[C@H](NS(=O)(=O)N[C@@H](CCCCN)C(=O)O)C(=O)N[C@H]1C[C@H]2CC[C@]1(C)C2(C)C] | D | 1.80 | 447.26 | 447.28 |
| 149 | 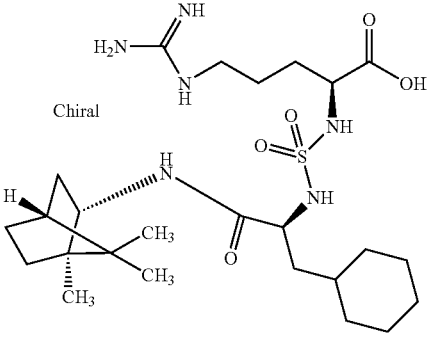 [SMILES: CC1(C)[C@@H]2CC[C@@]1(C)[C@@H](NC(=O)[C@H](CC1CCCCC1)NS(=O)(=O)N[C@@H](CCCNC(=N)N)C(=O)O)C2] | D | 2.21 | 543.33 | 543.38 |

-continued
| Example | Formula | LC/MS Method | $R_t$ | $[M+H]^+$ calc. | $[M+H]^+$ found |
|---|---|---|---|---|---|
| 150 | 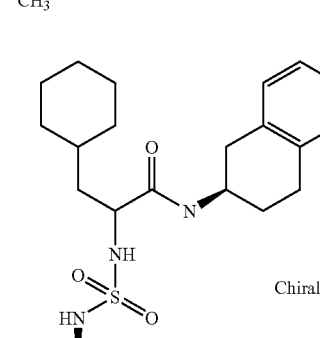 | C | 1.58 | 485.28 | 485.39 |
| 151 | 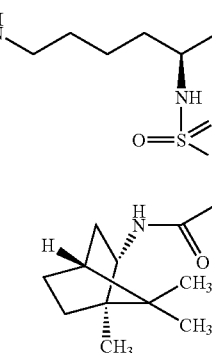 | A | 1.14 | 496.67 | 495.35 |
| 152 | 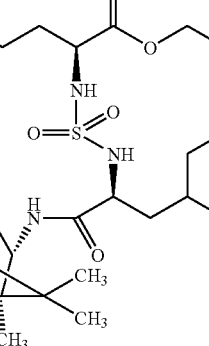 | D | 3.21 | 641.43 | 641.34 |
| 153 | 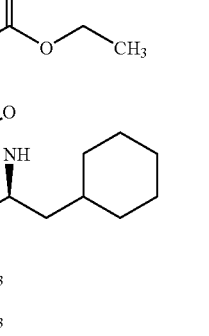 | D | 1.96 | 461.28 | 461.23 |

-continued

| Example | Formula | LC/MS Method | R_t | [M + H]+ calc. | [M + H]+ found |
|---|---|---|---|---|---|
| 154 | | D | 2.29 | 529.34 | 529.34 |
| 155 | | B | 1.51 | 515.33 | 515.34 |
| 156 | | F | 1.63 | 513.31 | 513.33 |
| 157 | | C | 1.91 | 533.28 | 533.17 |
| 158 | | C | 1.84 | 533.28 | 533.23 |

-continued
| Example | Formula | LC/MS Method | $R_t$ | $[M+H]^+$ calc. | $[M+H]^+$ found |
|---|---|---|---|---|---|
| 159 | 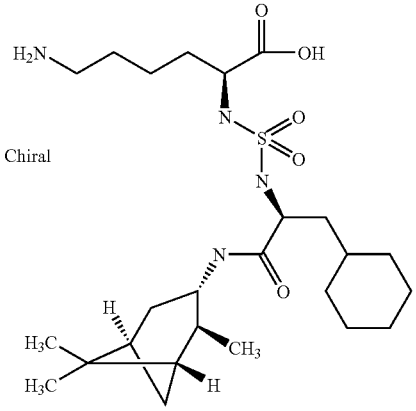 [SMILES: C[C@@H]1[C@@H](NC(=O)[C@H](CC2CCCCC2)NS(=O)(=O)N[C@@H](CCCCN)C(=O)O)C[C@H]2C[C@@H]1C2(C)C] | B | 1.51 | 515.33 | 515.56 |
| 160 | 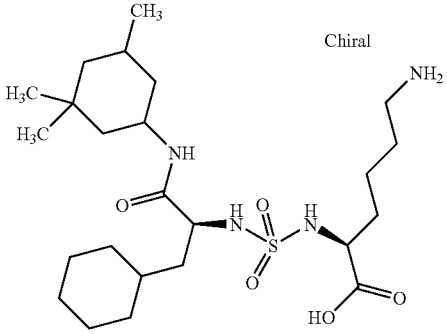 [SMILES: CC1CC(NC(=O)[C@H](CC2CCCCC2)NS(=O)(=O)N[C@@H](CCCCN)C(=O)O)CC(C)(C)C1] | B | 1.50 | 503.33 | 503.49 |
| 161 | 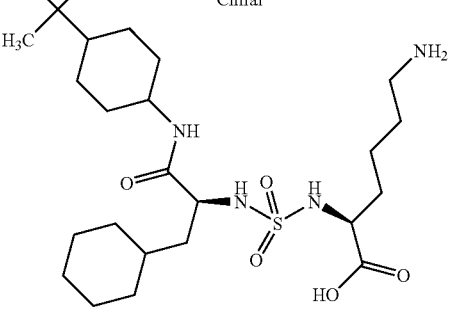 | B | 1.58 | 517.34 | 517.49 |
| 162 | 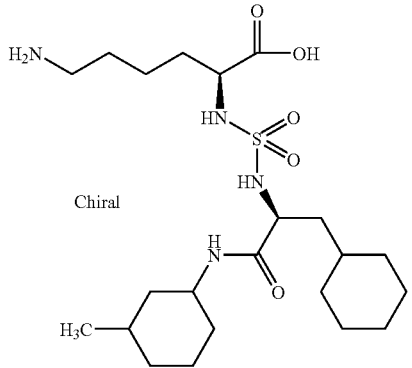 [SMILES: CC1CCCC(NC(=O)[C@H](CC2CCCCC2)NS(=O)(=O)N[C@@H](CCCCN)C(=O)O)C1] | B | 1.38 | 475.30 | 475.45 |

Example 163

(S)-6-Amino-2-{[(S)-2-cyclohexyl-1-((1R,2S,4R)-1,7,7-trimethyl-bicyclo[2.2.1]hept-2-ylcarbamoyl)-ethylsulfamidyl]}-hexanoic acid

1) Benzyl(S)-6-benzyloxycarbonylamino-2-(2-oxo-oxazolidine-sulfonylamino)-hexanoate A solution of 2.61 ml of 2-bromoethanol (36.9 mmol, 1.0 equiv.) in dichloromethane (20 ml) was slowly added to a solution of 5.21 g of chlorosulfonyl isocyanate (36.9 mmol, 1.0 equiv.) in dichloromethane (300 ml) at 0° C. under argon in such a way that the internal temperature remained below 10° C. Stirring was then continued at 0° C. for 30 min. A solution of 15.0 g of H-Lys(Z)-OBzL.HCl (36.9 mmol, 1.0 equiv.) and 16.5 ml of triethylamine (118.0 mmol, 3.2 equivalents (equiv.)) in 120 ml of $CH_2Cl_2$ was added dropwise to the solution in such a way that the temperature of the reaction mixture did not go above 10° C. After the addition, the ice bath was removed and the mixture was stirred at RT for 4 h. The organic solution was then washed three times with 100 ml of 0.2M HCl (aq.), dried over $Na_2SO_4$ and concentrated. 18.4 g of the crude title compound were obtained as a colorless oil which was directly employed further in step 3.

LC-MS: $R_t$(min) 1.82; calc.: $[M+H]^+$ 520.17 found: 520.30 (method B).

2) tert-Butyl[(S)-2-cyclohexyl-1-((1R,2S,4R)-1,7,7-trimethyl-bicyclo[2.2.1]hept-2-ylcarbamoyl)-ethyl]-carbamate 3.53 g of 1-ethyl-3-(3-dimethylaminopropyl)carbodiimide hydrochloride (18.4 mmol, 1.0 equiv.), 1.25 g of 1-hydroxybenzotriazole (9.2 mmol, 0.5 equiv.) and 7.3 ml of Hünig's base were added to a solution of 5.0 g of (S)-2-tert-butoxycarbonylamino-3-cyclohexylpropionic acid (Boc-Cha-OH, 18.4 mmol, 1.0 equiv.) in DMF (60 ml) at 0° C. under argon, and the mixture was stirred for 30 min. Then 2.83 g of (R)-(+)-bornylamine (18.4 mmol, 1.0 equiv.) and 3.7 ml of Hünig's base were added, and the mixture was stirred at RT for 16 h. The reaction mixture was quenched with $NaHCO_3$ (saturated, aq.) and extracted three times with ethyl acetate. The combined organic phases were washed twice with water and dried over $Na_2SO_4$ and concentrated. Purification by flash chromatography on silica gel with heptane/ethyl acetate mixtures as eluent afforded 6.58 g (88% yield) of the title compound as a colorless oil.

LC-MS: $R_t$(min) 2.42; calc.: $[M+H]^+$ 407.33 found: 407.32 (method B).

3) (S)-2-Amino-3-cyclohexyl-N-((1R,2S,4R)-1,7,7-trimethyl-bicyclo[2.2.1]hept-2-yl)-propionamide trifluoroacetate 50 ml of TFA were slowly added to a solution of 6.5 g of tert-butyl[(S)-2-cyclohexyl-1-((1R,2S,4R)-1,7,7-trimethyl-bicyclo[2.2.1]hept-2-ylcarbamoyl)-ethyl]-carbamate (16.0 mmol) in 50 ml of $CH_2Cl_2$ at 0° C. under argon. The mixture was allowed to reach RT. After 3 h, the reaction mixture was concentrated. The title compound was obtained as a pale yellow oil which was employed directly in the next step. LC-MS $R_t$(min) 1.60; calc.: $[M+H]^+$ 307.27 found: 307.39 (method C).

4) Benzyl(S)-6-benzyloxycarbonylamino-2-{[(S)-2-cyclohexyl-1-((1R,2S,4R)-1,7,7-trimethyl-bicyclo[2.2.1]hept-2-ylcarbamoyl)-ethylsulfamidyl]}-hexanoate 11.63 g of benzyl(S)-6-benzyloxycarbonylamino-2-(2-oxo-oxazolidine-sulfonylamino)-hexanoate (22.4 mmol, 1.4 equiv.) and 4.9 g of (S)-2-amino-3-cyclohexyl-N-((1R,2S,4R)-1,7,7-trimethyl-bicyclo[2.2.1]hept-2-yl)-propionamide trifluoroacetate (16.0 mmol, 1.0 equiv.) were suspended in 80 ml of MeCN and, after addition of 8.9 ml of $Et_3N$, the mixture was heated under reflux for 20 h. After cooling, the volatile constituents were removed in a rotary evaporator and the residue was purified by flash chromatography on silica gel with heptane/ethyl acetate mixtures as eluent. 9.0 g (76% yield) of the title compound were obtained as a colorless foam.

LC-MS: $R_t$(min) 2.61; calc.: $[M+H]^+$ 739.41 found: 739.43 (method B).

5) (S)-6-Amino-2-{[(S)-2-cyclohexyl-1-((1R,2S,4R)-1,7,7-trimethyl-bicyclo[2.2.1]hept-2-ylcarbamoyl)-ethylsulfamidyl]}-hexanoic acid 9.0 g of benzyl(S)-6-benzyloxycarbonylamino-2-{[(S)-2-cyclohexyl-1-((1R,2S,4R)-1,7,7-trimethyl-bicyclo[2.2.1]hept-2-ylcarbamoyl)-ethylsulfamidyl]}-hexanoate (12.2 mmol) were dissolved in 90 ml of methanol and, after addition of 600 mg of 10% Pd/C, hydrogenated at RT under atmospheric pressure for 3.5 h. The reaction mixture was filtered through Celite and concentrated. 6.1 g (97%) of the title compound were obtained as a colorless oil. 100 mg of the compound were dissolved in 5 ml of MeCN. Addition of 50 ml of water resulted in a suspension. Freeze drying resulted in a colorless solid.

LC-MS: $R_t$(min) 1.70; calc.: $[M+H]^+$ 515.33 found: 515.35 (method F).
$^1$H-NMR (DMSO-$d_6$) δ 0.68 (s, 3H), 0.82 (s, 3H), 0.83-0.91 (m, 2H), 0.89 (s, 3H), 0.97 (dd, 1H, J=4.8, 13.0 Hz), 1.08-1.34 (m, 7H), 1.35-1.55 (m, 5H), 1.56-1.72 (m, 9H), 1.78 (d, 1H, J=13.0 Hz), 2.04-2.13 (m, 1H), 2.75 (t, 2H, J=7.1 Hz), 3.51 (t, 1H, J=5.5 Hz), 3.83 (t, 1H, J=7.0 Hz), 4.03-4.10 (m, 1H), 6.91-7.05 (br, 1H), 7.77 (d, 1H, J=8.8 Hz), 7.5-8.2 (br, 2H).

Example 164

3-(6-Amino-pyridin-3-ylmethyl)-2-[(S)-2-cyclohexyl-1-((1R,2S,4R)-1,7,7-trimethyl-bicyclo[2.2.1]hept-2-yl-carbamoyl)-ethylsulfamidyl]-propionic acid

1) tert-Butyl 2-amino-3-(6-tert-butoxycarbonylamino-pyridin-3-yl)-propionate 660 mg of N-(diphenylmethylene)glycine tert-butyl ester (2.23 mmol, 1.0 equiv.) were dissolved in 15 ml of dry THF and cooled to 0° C. under argon. Then 2.23 ml of 1 M lithium hexamethyldisilazane (LiHMDS) solution in THF were added dropwise, and the mixture was stirred at 0° C. for 15 min. Subsequently, 642 mg of tert-butyl (5-bromomethylpyridin-2-yl)-carbamate (2.23 mmol, 1.0 equiv.) were added, and the mixture was stirred at 0° C. for 2 h. The mixture was quenched with 18 ml of sat. citric acid and stirred at RT for 1 h. The mixture was extracted with ethyl acetate (2×30 ml), and the organic phases were washed with 50 ml of 1 M HCl. The aqueous phases were combined and adjusted to pH 10 with 2M NaOH and then extracted 3× with ethyl acetate. The combined organic phases were dried over Na$_2$SO$_4$ and concentrated. The residue was purified by flash chromatography on silica gel with heptane/ethyl acetate mixtures as eluent. 600 mg (80% yield) of the title compound were obtained as a colorless solid.

LC-MS: R$_t$(min) 1.06; calc.: [M+H]$^+$ 338.21 found: 338.27 (method B).

2) tert-Butyl 3-(6-tert-butoxycarbonyl amino-pyridin-3-yl)-2-(2-oxo-oxazolidine-3-sulfonylamino)-propionate A solution of 0.126 ml of 2-bromoethanol (1.78 mmol, 1.0 equiv.) in dichloromethane (10 ml) was slowly added dropwise to a solution of 251 mg of chlorosulfonyl isocyanate (1.78 mmol, 1.0 equiv.) in dichloromethane (10 ml) under argon at 0° C. in such a way that the temperature did not exceed 10° C. After the addition, the mixture was stirred at 0° C. for a further 30 min. A mixture of 600 mg of tert-butyl 2-amino-3-(6-tert-butoxycarbonylamino-pyridin-3-yl)-propionate (1.78 mmol, 1.0 equiv.) and 0.545 ml of triethylamine (3.91 mmol, 2.2 equiv.) in 5 ml of CH$_2$Cl$_2$ was added dropwise to this solution in such a way that the temperature did not rise above 10° C. After the addition, the ice bath was removed and the mixture was stirred at RT for a further 3 h. The residue after concentration was chromatographed on silica gel with heptane/ethyl acetate mixtures as eluent. 320 mg (37% yield) of the title compound were obtained as a colorless solid.

LC-MS: R$_t$(min) 1.40; calc.: [M+H]$^+$ 487.19 found: 487.26 (method B).

3) tert-Butyl 3-(6-tert-butoxycarbonylamino-pyridin-3-ylmethyl)-2-[(S)-2-cyclohexyl-1-((1R,2S,4R)-1,7,7-trimethyl-bicyclo[2.2.1]hept-2-yl-carbamoyl)-ethylsulfamidyl]propionate 320 mg of tert-butyl 3-(6-tert-butoxycarbonylamino-pyridin-3-yl)-2-(2-oxo-oxazolidine-3-sulfonylamino)-propionate (0.66 mmol, 1.0 equiv.) and 277 mg of (S)-2-amino-3-cyclohexyl-N-((1R,2S,4R)-1,7,7-trimethyl-bicyclo[2.2.1]hept-2-yl)-propionamide trifluoroacetate (0.66 mmol, 1.0 equiv.), prepared as described above, were suspended in 12 ml of MeCN and, after addition of 0.37 ml of Et$_3$N, heated under reflux for 20 h. After cooling, the volatile constituents were evaporated off, and the residue was purified by flash chromatography on silica gel with heptane/ethyl acetate mixtures as eluent. 139 mg (30% yield) of the title compound were obtained as a colorless solid.

LC-MS: R$_t$(min) 2.19; calc.: [M+H]$^+$ 706.42 found: 706.54 (method B).

4) 3-(6-Amino-pyridin-3-ylmethyl)-2-[(S)-2-cyclohexyl-1-((1R,2S,4R)-1,7,7-trimethyl-bicyclo[2.2.1]hept-2-yl-carbamoyl)-ethylsulfamidyl]-propionic acid trifluoroacetate 135 mg of tert-butyl 3-(6-tert-butoxycarbonylamino-pyridin-3-ylmethyl)-2-[(S)-2-cyclohexyl-1-((1R,2S,4R)-1,7,7-trimethyl-bicyclo[2.2.1]hept-2-yl-carbamoyl)-ethylsulfamidyl]propionate (0.19 mmol) were dissolved in 1.0 ml of CH$_2$Cl$_2$ and cooled to 0° C. Then 0.8 ml of TFA was added, and the mixture was stirred at RT. After 1 h, the volatile constituents were evaporated and the residue was purified by RP-HPLC. 70 mg (55% yield) of the title compound were obtained as a colorless solid.

LC-MS: R$_t$(min) 1.61; calc.: [M+H]$^+$ 550.31 found: 550.39 (method B), 1:1 mixture of the diastereomers.

$^1$H-NMR (DMSO-d$_6$) δ 0.67 (s, 3H), 0.69 (s, 3H), 0.82 (s, 6H), 0.79-0.92 (m, 4H), 1.08-1.39 (m, 16H), 1.56-1.78 (m, 16H), 2.01 (t, 1H, J=12.0 Hz), 2.11 (t, 1H, J=12.0 Hz), 2.70 (dd, 1H, J=6.4, 13.9 Hz), 2.79 (dd, 2H, J=7.0, 13.9 Hz), 2.94 (dd, 1H, J=5.5, 14.1 Hz), 3.73-3.90 (m, 2H), 4.01-4.13 (m, 1H), 6.80 (d, 0.5H, J=8.0 Hz), 6.94 (dd, 2H, J=5.3, 8.6 Hz), 7.01 (d, 1H, J=9.1 Hz), 7.11 (d, 1H, J=8.7 Hz), 7.18 (d, 1H, J=9.1 Hz), 7.69-7.74 (m, 3H), 7.79 (d, 2H, J=9.4 Hz), 7.85 (dd, 1H, J=1.9, 9.1 Hz), 7.88-7.99 (br, 4H)

The following examples were prepared in analogy to Example 163:

| 165 | 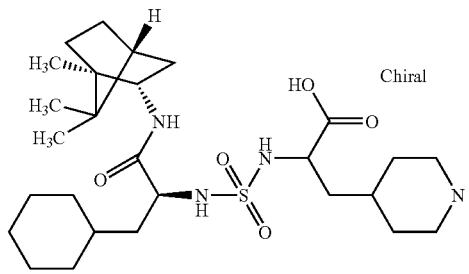 [SMILES: CC1(C)[C@@H]2CC[C@@]1(C)[C@@H](NC(=O)[C@H](CC1CCCCC1)NS(=O)(=O)NC(CC1CCNCC1)C(=O)O)C2] | B | 1.55 | 541.34 | 541.39 |

| 166 | 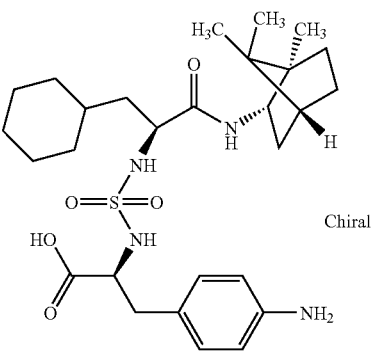 [SMILES: CC1(C)[C@@H]2CC[C@@]1(C)[C@@H](NC(=O)[C@H](CC1CCCCC1)NS(=O)(=O)N[C@@H](Cc1ccc(N)cc1)C(=O)O)C2] | B | 1.50 | 549.31 | 549.35 |

| | | | | | |
|---|---|---|---|---|---|
| 167 | 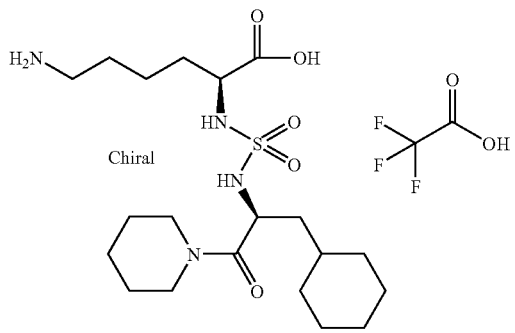 [SMILES: NCCCC[C@H](NS(=O)(=O)N[C@@H](CC1CCCCC1)C(=O)N1CCCCC1)C(=O)O ; O=C(O)C(F)(F)F] | B | 1.28 | 447.26 | 447.25 |
| 168 | 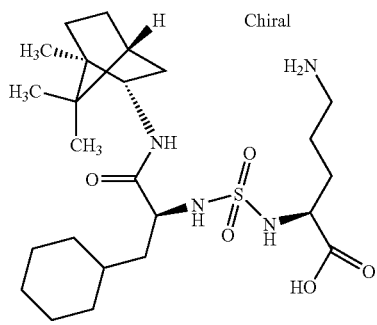 [SMILES: CC1(C)[C@@H]2CC[C@@]1(C)[C@@H](NC(=O)[C@H](CC1CCCCC1)NS(=O)(=O)N[C@@H](CCCN)C(=O)O)C2] | A | 1.20 | 501.71 | 501.25 |
| 169 | 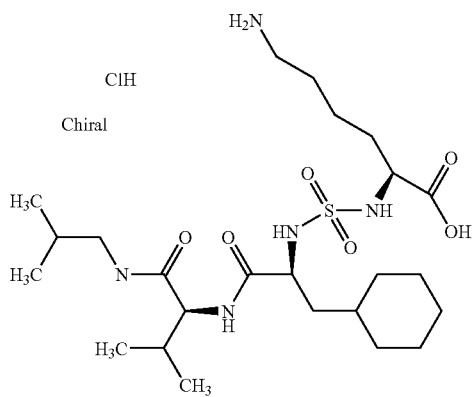 [SMILES: CC(C)CNC(=O)[C@@H](NC(=O)[C@H](CC1CCCCC1)NS(=O)(=O)N[C@@H](CCCCN)C(=O)O)C(C)C ; Cl] | A | 1.00 | 534.74 | 534.35 |
| 170 | 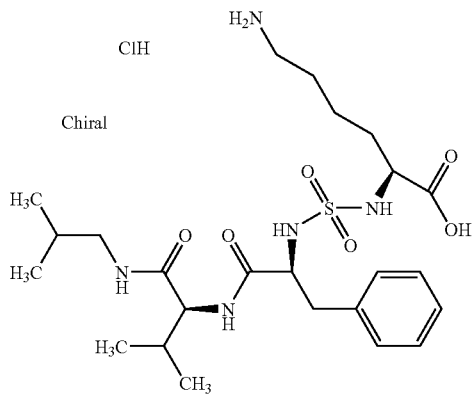 [SMILES: CC(C)CNC(=O)[C@@H](NC(=O)[C@H](Cc1ccccc1)NS(=O)(=O)N[C@@H](CCCCN)C(=O)O)C(C)C ; Cl] | A | 0.94 | 528.70 | 528.25 |

| | | | | | |
|---|---|---|---|---|---|
| 171 | (structure: lysine-sulfamide-cyclohexylalanine-isobutylamide, ClH salt, Chiral) | A | 0.96 | 435.61 | 435.25 |
| 172 | (structure: lysine-sulfamide-cyclohexylalanine-norbornylamide, TFA salt, Chiral) | B | 1.32 | 473.28 | 473.30 |
| 173 | (structure: lysine-sulfamide-cyclohexylalanine-bornylamide, TFA salt, Chiral) | B | 1.51 | 515.33 | 515.33 |
| 174 | (structure: lysine-sulfamide-cyclohexylalanine-norbornylamide, TFA salt, Chiral) | B | 1.33 | 473.30 | 473.28 |
| 175 | (structure: lysine-sulfamide-cyclohexylalanine-tricyclodecylamide, TFA salt) | B | 1.45 | 513.31 | 513.34 |

-continued
| | | | | | |
|---|---|---|---|---|---|
| 176 | 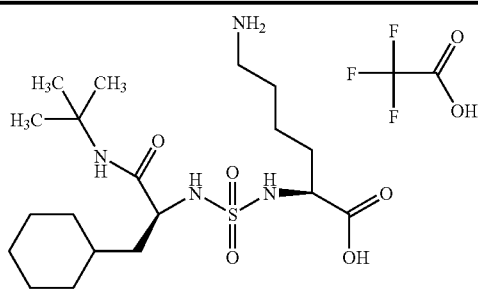 | B | 1.26 | 435.26 | 435.28 |
| 177 | 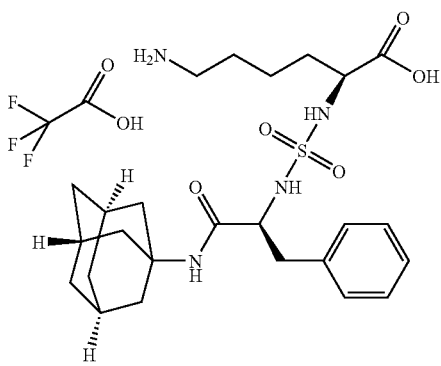 | B | 1.35 | 507.26 | 507.24 |
| 178 | 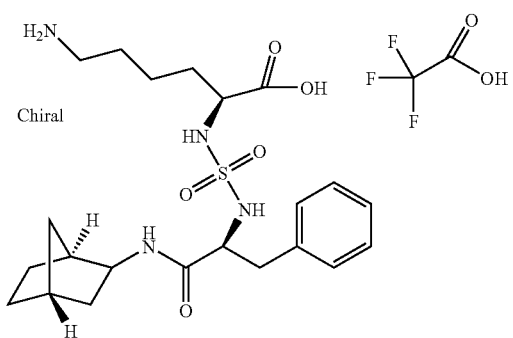 [SMILES: NCCCC[C@H](NS(=O)(=O)N[C@@H](Cc1ccccc1)C(=O)NC1C[C@@H]2CC[C@H]1C2)C(=O)O ; O=C(O)C(F)(F)F] | F | 1.30 | 467.23 | 467.35 |
| 179 | 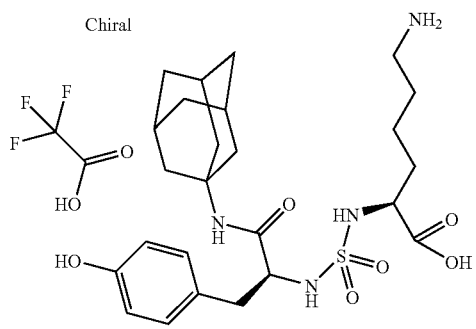 | F | 1.36 | 523.23 | 523.41 |
| 180 | 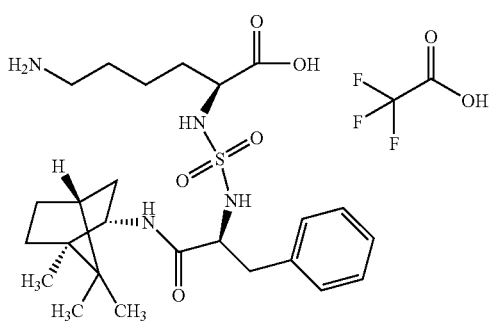 | F | 1.53 | 509.28 | 509.40 |

| 181 | 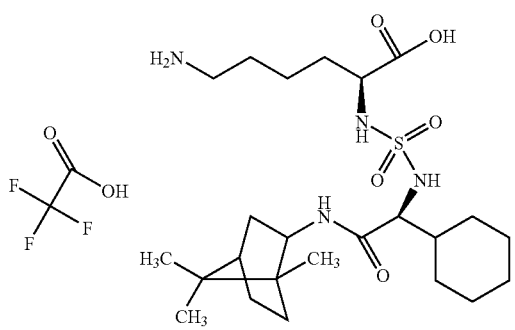 [SMILES: O=C(O)C(F)(F)F ; CC1(C)C2CCC1(C)C(NC(=O)[C@@H](NS(=O)(=O)N[C@@H](CCCCN)C(=O)O)C1CCCCC1)C2] | C | 1.60 | 501.31 | 501.29 |
| 182 | 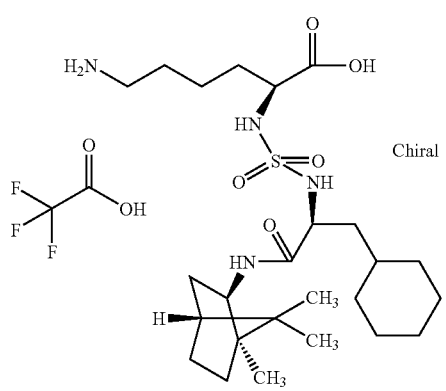 [SMILES: O=C(O)C(F)(F)F ; CC1(C)[C@@H]2CC[C@@]1(C)[C@H](NC(=O)[C@H](CC1CCCCC1)NS(=O)(=O)N[C@@H](CCCCN)C(=O)O)C2] | F | 1.69 | 515.33 | 515.51 |
| 183 | 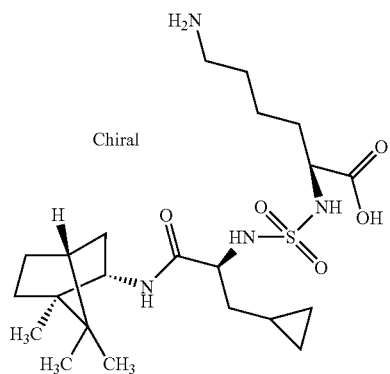 [SMILES: CC1(C)[C@@H]2CC[C@@]1(C)[C@@H](NC(=O)[C@H](CC1CC1)NS(=O)(=O)N[C@@H](CCCCN)C(=O)O)C2] | B | 1.31 | 473.28 | 473.39 |
| 184 | 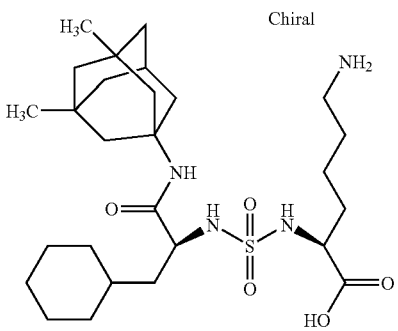 [SMILES: CC12CC3CC(C)(C1)CC(NC(=O)[C@H](CC1CCCCC1)NS(=O)(=O)N[C@@H](CCCCN)C(=O)O)(C3)C2] | B | 1.61 | 541.34 | 541.39 |

| | | | | | | |
|---|---|---|---|---|---|---|
| 185 | 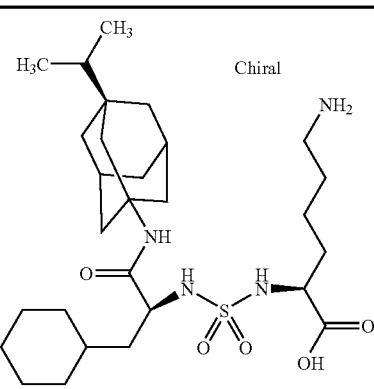 | | B | 1.66 | 555.36 | 555.36 |
| 186 | 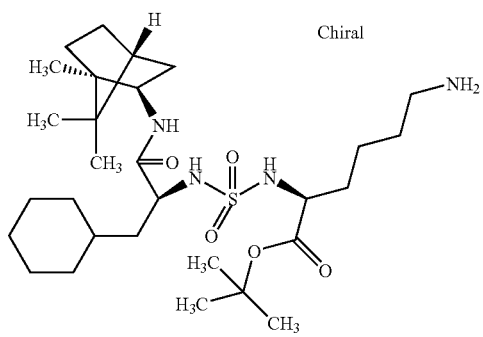 [SMILES: CC(C)(C)OC(=O)[C@H](CCCCN)NS(=O)(=O)N[C@@H](CC1CCCCC1)C(=O)N[C@@H]1C[C@H]2CC[C@]1(C)C2(C)C] | | B | 1.67 | 571.39 | 571.50 |

Pharmacological Examples

The prepared substances were tested for TAFIa inhibition using the Actichrome plasma TAFI activity kit from American Diagnostica (Pr. No. 874). This entailed adding 28 µl of assay buffer (20 mM Hepes, 150 mM NaCl, pH 7.4) and 10 µl of TAFIa (American Diagnostica Pr. No. 874TAFIA; 2.5/ml) to 2 µl of 2.5 mM DMSO solution of the substance and incubating in a 96 half-well microtiter plate at room temperature for 15 minutes. The enzymic reaction was started by adding 10 µl of TAFIa developer (prediluted 1:2 with assay buffer). The time course of the reaction was followed at 420 nm in a microtiter plate reader (SpectraMax plus 384; Molecular Devices) for 15 minutes.

The $IC_{50}$ values were calculated from the averaged values (duplicate determination) of serial dilutions of the substance with the aid of the Softmax Pro software (version 4.8; Molecular Devices).

Table 1 shows the results.

TABLE 1

| Example No. | $IC_{50}$ [µM] |
|---|---|
| 2 | 1.424 |
| 10 | 0.979 |
| 11 | 0.644 |
| 12 | 1.257 |
| 13 | 1.26 |
| 16 | 0.039 |
| 19 | 0.353 |
| 20 | 0.105 |
| 21 | 0.904 |
| 25 | 0.463 |
| 26 | 0.487 |
| 27 | 0.187 |
| 28 | 0.118 |

TABLE 1-continued

| Example No. | $IC_{50}$ [µM] |
|---|---|
| 29 | 0.694 |
| 31 | 0.076 |
| 32 | 0.753 |
| 33 | 0.19 |
| 34 | 1.085 |
| 37 | 0.537 |
| 38 | 0.297 |
| 39 | 1.14 |
| 41 | 0.09 |
| 42 | 0.839 |
| 43 | 0.046 |
| 44 | 0.144 |
| 49 | 0.106 |
| 53 | 0.391 |
| 56 | 0.133 |
| 57 | 0.544 |
| 64 | 0.757 |
| 69 | 1.047 |
| 72 | 0.167 |
| 73 | 0.047 |
| 74 | 0.019 |
| 75 | 0.653 |
| 76 | 0.845 |
| 77 | 0.003 |
| 78 | 0.305 |
| 79 | 0.031 |
| 81 | 0.166 |
| 84 | 0.654 |
| 85 | 0.039 |
| 86 | 0.06 |
| 88 | 0.393 |
| 90 | 0.111 |
| 91 | 0.004 |
| 92 | 0.160 |
| 93 | 1.499 |
| 94 | 109.23 |
| 95 | 41.042 |

TABLE 1-continued

| Example No. | IC$_{50}$ [µM] |
|---|---|
| 96 | 0.015 |
| 97 | 0.462 |
| 98 | 1.036 |
| 99 | 0.057 |
| 100 | 0.111 |
| 103 | 0.015 |
| 107 | 1.10 |
| 108 | 0.007 |
| 109 | 0.009 |
| 110 | 0.006 |
| 111 | 0.004 |
| 113 | 0.747 |
| 114 | 0.519 |
| 115 | 0.239 |
| 118 | 0.267 |
| 119 | 1.302 |
| 120 | 0.615 |
| 121 | 0.370 |
| 122 | 0.525 |
| 124 | 0.018 |
| 126 | 0.204 |
| 127 | 0.693 |
| 128 | 0.391 |
| 129 | 0.608 |
| 133 | 0.636 |
| 134 | 0.532 |
| 135 | 0.522 |
| 137 | 0.14 |
| 139 | 0.376 |
| 140 | 0.318 |
| 142a | 0.0007 |
| 142b | 0.006 |
| 143 | 9.756 |
| 142 | 10.601 |
| 146 | 0.071 |
| 149 | 0.049 |
| 150 | 0.357 |
| 153 | 1.087 |
| 154 | 0.220 |
| 155 | 0.669 |
| 156 | 0.492 |
| 157 | 0.2 |
| 159 | 0.131 |
| 163 | 0.012 |
| 164 | 0.026 |
| 165 | 0.882 |
| 169 | 0.770 |
| 172 | 0.420 |
| 173 | 0.012 |
| 174 | 0.326 |
| 175 | 0.168 |
| 177 | 2.117 |
| 180 | 0.168 |
| 182 | 0.069 |
| 183 | 0.805 |
| 184 | 1.069 |
| 185 | 0.4 |
| 186 | 22.943 |
| 187 | 10.176 |

The invention claimed is:

1. A compound of the formula I

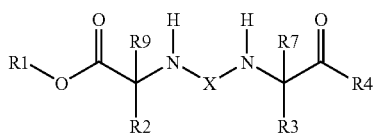

where
X is —S(O)$_2$—,
R1 is 1) hydrogen atom,
2) —(C$_1$-C$_6$)-alkyl,
3) —(C$_0$-C$_4$)-alkylene-(C$_3$-C$_{12}$)-cycloalkyl or
4) —(C$_1$-C$_6$)-alkylene-(C$_6$-C$_{14}$)-aryl,
R2 is a radical of the formula II $$-(A1)_m-A2 \qquad (II)$$

in which
m is the integer zero or 1,
A1 is
1) —(CH$_2$)$_n$— in which n is the integer zero, 1, 2 or 3,
2) —NH—(CH$_2$)$_n$— in which n is the integer zero, 1, 2 or 3,
3) —NH(C$_1$-C$_6$)-alkyl)-(CH$_2$)$_n$— in which n is the integer zero, 1, 2 or 3,
4) —NH((C$_3$-C$_6$)-cycloalkyl)-(CH$_2$)$_n$— in which n is the integer zero, 1, 2 or 3,
5) —O—(CH$_2$)$_n$— in which n is the integer zero, 1, 2 or 3, or
6) —(CH$_2$)$_n$—SO$_x$— in which n is the integer zero, 1, 2 or 3 and x the integer zero, 1 or 2,
A2 is
1) Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, and is unsubstituted or substituted independently of one another once, twice or three times by —(C$_1$-C$_3$)-alkyl, halogen, —NH$_2$, —CF$_3$ or —O—CF$_3$,
2) —(C$_0$-C$_6$)-alkylene-NH$_2$,
3) —(C$_1$-C$_6$)-alkylene-NH—C(=NH)—NH$_2$,
4) —(C$_1$-C$_6$)-alkylene-NH—C(=NH)—(C$_1$-C$_4$)-alkyl,
5) —(C$_0$-C$_4$)-alkylene-O—NH—C(=NH)—NH$_2$,
6) —(C$_0$-C$_4$)-alkylene-NH—C(O)—(C$_1$-C$_6$)-alkyl,
7) —(C$_1$-C$_6$)-alkylene-NH—C(O)—O—(C$_1$-C$_4$)-alkylene-(C6-C14)-aryl, where aryl is unsubstituted or substituted by —NH$_2$ or is substituted by —NH$_2$ and once, twice or three times by R15,
8) —(C$_3$-C$_8$)-cycloalkyl-NH$_2$, or
9) —(C$_0$-C$_4$)-alkylene-(C$_6$-C$_{14}$)-aryl, where aryl is unsubstituted or substituted by —NH$_2$ or is substituted by —NH$_2$ and once, twice or three times by R15,
R3 is
1) —(C$_1$-C$_6$)-alkyl,
2) —(C$_0$-C$_4$)-alkylene-(C$_3$-C$_{12}$)-cycloalkyl,
3) —(C$_1$-C$_6$)-alkylene-(C$_6$-C$_{14}$)-aryl, where aryl is substituted independently of one another once, twice or three times by R15,
4) —(C$_0$-C$_8$)-alkylene-N(R5)-PG1,
5) —(C$_1$-C$_6$)-alkylene-NH—C(O)—O—(C$_1$-C$_4$)-alkylene-(C6-C14)-aryl, where aryl is substituted independently of one another once, twice or three times by R15,
6) —(C$_0$-C$_4$)-alkylene-(C$_6$-C$_{14}$)-aryl-(C$_0$-C$_4$)-alkylene-N(R5)-PG1,
7) —(C$_0$-C$_8$)-alkylene-O-PG2,
8) —(C$_0$-C$_4$)-alkylene-(C$_6$-C$_{14}$)-aryl-(C$_0$-C$_4$)-alkylene-O-PG2,
9) —(C$_0$-C$_8$)-alkylene-C(O)—O-PG3,
10) —(C$_0$-C$_4$)-alkylene-(C$_6$-C$_{14}$)-aryl-(C$_0$-C$_4$)-alkylene-C(O)—O-PG3 or
11) hydrogen atom,
R4 is —N(R6)$_2$,
where R6 are identical or different and are independently of one another 1) hydrogen atom,
2) —($C_1$-$C_6$)-alkyl,
3) —($C_0$-$C_4$)-alkylene-($C_3$-$C_{12}$)-cycloalkyl, where cycloalkyl is unsubstituted or substituted independently of one another once, twice, three or four times by R11, halogen, —C(O)—O—R11, —($C_1$-$C_4$)-alkyl-O—R11 or —O—($C_1$-$C_4$)-alkyl,
4) —($C_0$-$C_6$)-alkylene-($C_6$-$C_{14}$)-aryl, where aryl and alkylene are unsubstituted or substituted independently of one another once, twice, three or four times by R11, halogen, —C(O)—O—R11, —($C_1$-$C_4$)-alkyl-O—R11, —C(O)—N(R8)$_2$ or —O—($C_1$-$C_4$)-alkyl,
5) —($C_0$-$C_8$)-alkylene-N(R5)-PG1,
6) —($C_0$-$C_4$)-alkylene-($C_6$-$C_{14}$)-aryl-($C_0$-$C_4$)-alkyl-N(R5)-PG1,
7) —($C_0$-$C_8$)-alkylene-O-PG2,
8) —($C_0$-$C_4$)-alkylene-($C_6$-$C_{14}$)-aryl-($C_0$-$C_4$)-alkyl-O-PG2,
9) —($C_0$-$C_8$)-alkylene-C(O)—O—R11,
10) —($C_0$-$C_4$)-alkylene-($C_6$-$C_{14}$)-aryl-($C_0$-$C_4$)-alkyl-C(O)—O-PG3,
11) —($C_0$-$C_4$)-alkylene-Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —($C_1$-$C_4$)-alkyl-O—R11 or —O—($C_1$-$C_4$)-alkyl,
12) —($C_1$-$C_3$)-fluoroalkyl,
13) —($C_0$-$C_4$)-alkylene-CH(R11)-C(O)—NH$_2$,
14) —($C_0$-$C_4$)-alkylene-CH(R11)-C(O)—NH—($C_1$-$C_4$)-alkyl,
15) —($C_0$-$C_4$)-alkylene-CH(R11)-C(O)—NH—CH(R12)-R13, or
16) amino acid, where the linkage of the amino acid takes place by a peptide linkage, and the carboxyl radical of the amino acid is unsubstituted or substituted by PG3 or by —N(R5)$_2$,
or the two R6 radicals form together with the N atom to which they are bonded a mono- or bicyclic ring having 4 to 9 ring atoms which is saturated, partly saturated or aromatic, where the ring is unsubstituted or substituted once or twice by —($C_1$-$C_4$)-alkyl, —C(O)—O—R11, halogen, —($C_1$-$C_4$)-alkyl-O—R11 or phenyl,
R5 is hydrogen atom or —($C_1$-$C_6$)-alkyl,
PG1 is a protective group for the amino function,
PG2 is a protective group for the hydroxy function,
PG3 is a protective group for the carboxyl function,
R7 is hydrogen atom or —($C_1$-$C_6$)-alkyl,
R8 is hydrogen atom or —($C_1$-$C_6$)-alkyl,
R9 is hydrogen atom or —($C_1$-$C_6$)-alkyl,
R11 and R12 are identical or different and are independently of one another
1) hydrogen atom,
2) —($C_1$-$C_6$)-alkyl,
3) —($C_0$-$C_4$)-alkylene-phenyl, where phenyl is unsubstituted or substituted independently of one another once, twice or three times by halogen, —OH or —O—($C_1$-$C_4$)-alkyl,
4) —($C_0$-$C_4$)-alkylene-($C_3$-$C_{12}$)-cycloalkyl, where cycloalkyl is unsubstituted or substituted independently of one another once, twice, three or four times by R13, halogen, —C(O)—O—R13, —($C_1$-$C_4$)-alkyl-O—R13, —O—($C_1$-$C_4$)-alkyl or —($C_0$-$C_4$)-alkylene-phenyl,
5) —($C_0$-$C_4$)-alkylene-C(O)—N(R13)$_2$ or
6) —($C_0$-$C_4$)-alkylene-indolyl,
R13 is
1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14,
R14 is hydrogen atom, —($C_1$-$C_4$)-alkyl, —NH$_2$ or —OH, and
R15 is hydrogen atom, —($C_1$-$C_4$)-alkyl, —O—CF$_3$, —NH$_2$, —OH, —CF$_3$ or halogen, or
a stereoisomeric form of the compound of the formula I, or mixture of stereoisomeric forms in any ratio, or a physiologically tolerated salt of the compound of the formula I.

2. A compound of the formula I

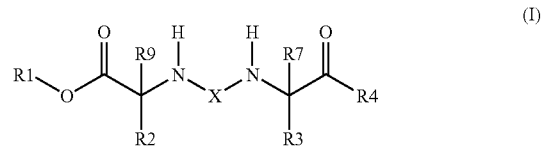

(I)

where
X is —S(O)$_2$—,
R1 is
1) hydrogen atom or
2) —($C_1$-$C_4$)-alkyl,
R2 is
1) —($C_1$-$C_6$)-alkylene-NH$_2$,
2) —($C_0$-$C_4$)-alkylene-pyridyl-NH$_2$,
3) —($C_0$-$C_4$)-alkylene-piperidinyl-NH$_2$,
4) —($C_0$-$C_4$)-alkylene-thiazolyl-NH$_2$,
5) —($C_1$-$C_6$)-alkylene-NH—C(=NH)—NH$_2$,
6) —($C_0$-$C_4$)-alkylene-($C_3$-$C_8$)-cycloalkyl-NH$_2$,
7) —($C_1$-$C_6$)-alkylene-NH—C(=NH)—($C_1$-$C_4$)-alkyl,
8) —($C_0$-$C_4$)-alkylene-O—NH—C(=NH)—NH$_2$,
9) —($C_1$-$C_6$)-alkylene-NH—C(O)—O—($C_1$-$C_4$)-alkylene-(C6-C14)-aryl, where aryl is unsubstituted or substituted by —NH$_2$ or is substituted by —NH$_2$ and once, twice or three times by R15,
10) —($C_0$-$C_4$)-alkylene-NH—C(O)—($C_1$-$C_4$)-alkyl,
11) —($C_0$-$C_4$)-alkylene-($C_6$-$C_{14}$)-aryl, where aryl is unsubstituted or substituted by —NH$_2$ or is substituted by —NH$_2$ and once, twice or three times by R15, or
12) —($C_1$-$C_4$)-alkylene-SO$_x$—($C_1$-$C_4$)-alkylene-NH$_2$ in which x is the integer zero, 1 or 2,
R3 is
1) —($C_1$-$C_4$)-alkyl,
2) —($C_0$-$C_4$)-alkylene-(C3-$C_8$)-cycloalkyl,
3) —($C_1$-$C_6$)-alkylene-($C_6$-$C_{14}$)-aryl, where aryl is substituted independently of one another once, twice or three times by R15,
4) —($C_1$-$C_6$)-alkylene-NH—C(O)—O—($C_1$-$C_4$)-alkylene-($C_6$-$C_{14}$)-aryl, where aryl is substituted independently of one another once, twice or three times by R15,
5) —($C_1$-$C_6$)-alkylene-NH-PG1,
6) —($C_1$-$C_6$)-alkylene-O-PG2,
7) —($C_1$-$C_6$)-alkyl, or
8) hydrogen atom,
where PG1 is t-butyloxycarbonyl or benzyloxycarbonyl, and PG2 is t-butyl-, t-butyloxycarbonyl or benzyloxycarbonyl, R4 is —N(R6)$_2$,
where R6 are identical or different and are independently of one another
1) hydrogen atom,
2) —(C$_1$-C$_6$)-alkyl,
3) —(C$_0$-C$_4$)-alkylene-(C$_3$-C$_{12}$)-cycloalkyl, where cycloalkyl is unsubstituted or substituted independently of one another once, twice, three or four times by R11, halogen, —C(O)—O—R11, —(C$_1$-C$_4$)-alkyl-O—R11 or —O—(C$_1$-C$_4$)-alkyl,
4) —(C$_0$-C$_4$)-alkylene-C(R11)(R12)-(C$_3$-C$_{12}$)-cycloalkyl, where cycloalkyl is unsubstituted or substituted independently of one another once, twice or three times by R11, halogen, —C(O)—O—R11, —(C$_1$-C$_4$)-alkyl-O—R11 or —O—(C$_1$-C$_4$)-alkyl,
5) —(C$_0$-C$_4$)-alkylene-Het, where Het means a 4- to 15-membered heterocyclic ring system having 4 to 15 ring atoms which are present in one, two or three ring systems connected together, and which comprise one, two, three or four identical or different heteroatoms selected from the group consisting of oxygen, nitrogen and sulfur, where Het or alkylene is unsubstituted or substituted independently of one another once, twice or three times by R11, halogen, —C(O)—O—R11, —(C$_1$-C$_4$)-alkyl-O—R11 or —O—(C$_1$-C$_4$)-alkyl,
6) —(C$_0$-C$_6$)-alkylene-(C6-C14)-aryl, where aryl or alkylene is unsubstituted or substituted independently of one another once, twice or three times by R11, halogen, —C(O)—O—R11, —(C$_0$-C$_4$)-alkyl-O—R11 or —O—(C$_1$-C$_4$)-alkyl,
7) —(C$_0$-C$_4$)-alkylene-C(R11)(R12)-aryl, where aryl or alkylene is unsubstituted or substituted independently of one another once, twice or three times by R11, halogen, —C(O)—O—R11, —(C$_0$-C$_4$)-alkyl-O—R11 or —O—(C$_1$-C$_4$)-alkyl,
8) 1,2,3,4-tetrahydronaphthalenyl, 9) —(C$_0$-C$_4$)-alkylene-CH(R11)-C(O)—NH$_2$,
10) —(C$_0$-C$_4$)-alkylene-CH(R11)-C(O)—NH—(C$_1$-C$_4$)-alkyl,
11) —(C$_0$-C$_4$)-alkylene-CH(R11)-C(O)—NH—CH(R12)-R13,
12) —(C$_0$-C$_6$)-alkylene-C(O)—O—R11, where alkylene is unsubstituted or substituted independently of one another once or twice by R11, halogen, —C(O)—O—R11, —(C$_1$-C$_4$)-alkyl-O—R11 or —O—(C$_1$-C$_4$)-alkyl,
13) —(C$_0$-C$_4$)-alkylene-C(R11)(R12)-C(O)—O—R11, or
14) —(C$_1$-C$_3$)-fluoroalkyl,
or the two R6 radicals form together with the N atom to which they are bonded a mono- or bicyclic ring having 4 to 9 ring atoms which is saturated, partly saturated or aromatic, where the ring is unsubstituted or substituted once or twice by —(C$_1$-C$_4$)-alkyl, —C(O)—O—R11, halogen, —(C$_1$-C$_4$)-alkyl-O—R11 or phenyl,
R7 is hydrogen atom or —(C$_1$-C$_4$)-alkyl,
R9 is hydrogen atom or —(C$_1$-C$_4$)-alkyl,
R11 and R12 are identical or different and are independently of one another
1) hydrogen atom,
2) —(C$_1$-C$_4$)-alkyl,
3) —(C$_0$-C$_4$)-alkylene-phenyl, where phenyl is unsubstituted or substituted independently of one another once, twice or three times by halogen, —OH or —O—(C$_1$-C$_4$)-alkyl,
4) —(C$_0$-C$_4$)-alkylene-(C$_3$-C$_{12}$)-cycloalkyl, where cycloalkyl is unsubstituted or substituted independently of one another once, twice, three or four times by R13, halogen, —C(O)—O—R13, —(C$_1$-C$_4$)-alkyl-O—R13, —O—(C$_1$-C$_4$)-alkyl or —(C$_0$-C$_4$)-alkylene-phenyl,
5) —(C$_0$-C$_4$)-alkylene-C(O)—N(R13)$_2$ or
6) —(C$_0$-C$_4$)-alkylene-indolyl,
R13 is
1) hydrogen atom,
2) —(C$_1$-C$_4$)-alkyl,
3) —(C$_0$-C$_4$)-alkylene-C(O)—O—R14,
4) —(C$_0$-C$_4$)-alkylene-C(O)—R14 or
5) —(C$_0$-C$_4$)-alkylene-O—R14,
R14 is hydrogen atom, —(C$_1$-C$_4$)-alkyl, —NH$_2$ or —OH, and
R15 is hydrogen atom, —(C$_1$-C$_4$)-alkyl, —O—CF$_3$, —NH$_2$, —OH, —CF$_3$ or halogen, or
a stereoisomeric form of the compound of the formula I, or mixture of stereoisomeric forms in any ratio, or a physiologically tolerated salt of the compound of the formula I.

3. The compound as claimed in claim 2, where
R1 is
1) hydrogen atom or
2) —(C$_1$-C$_4$)-alkyl,
R2 is
1) —(C$_1$-C$_6$)-alkylene-NH$_2$,
2) —(C$_1$-C$_4$)-alkylene-pyridyl-NH$_2$,
3) —(C$_1$-C$_4$)-alkylene-piperidinyl-NH$_2$,
4) —(C$_1$-C$_6$)-alkylene-NH—C(=NH)—NH$_2$,
5) —(C$_0$-C$_4$)-alkylene-(C$_3$-C$_6$)-cycloalkyl-NH$_2$,
6) —(C$_1$-C$_6$)-alkylene-NH—C(=NH)—(C$_1$-C$_4$)-alkyl,
7) —(C$_1$-C$_4$)-alkylene-O—NH—C(=NH)—NH$_2$,
8) —(C$_1$-C$_6$)-alkylene-NH—C(O)—O—(C$_1$-C$_4$)-alkylene-phenyl, where phenyl is unsubstituted or substituted by —NH$_2$ or is substituted by —NH$_2$ and once, twice or three times by R15,
9) —(C$_1$-C$_4$)-alkylene-NH—C(O)—(C$_1$-C$_4$)-alkyl,
10) —(C$_1$-C$_4$)-alkylene-phenyl, where phenyl is unsubstituted or substituted by —NH$_2$ or is substituted by —NH$_2$ and once, twice or three times by R15,
11) —(C$_1$-C$_4$)-alkylene-SO$_2$—(C$_1$-C$_4$)-alkylene-NH$_2$ or
12) —(C$_1$-C$_4$)-alkylene-S—(C$_1$-C$_4$)-alkylene-NH$_2$,
R3 is
1) —(C$_1$-C$_4$)-alkyl,
2) —(C$_1$-C$_4$)-alkylene-(C$_3$-C$_6$)-cycloalkyl,
3) —(C$_1$-C$_4$)-alkylene-phenyl, where phenyl is substituted independently of one another once, twice or three times by R15,
4) —(C$_1$-C$_6$)-alkylene-NH—C(O)—O—(C$_1$-C$_4$)-alkylene-phenyl, where phenyl is substituted independently of one another once, twice or three times by R15,
5) hydrogen atom,
R4 is —N(R6)$_2$,
where R6 are identical or different and are independently of one another
1) hydrogen atom,
2) —(C$_1$-C$_4$)-alkyl,
3) —(C$_0$-C$_4$)-alkylene-(C$_3$-C$_{12}$)-cycloalkyl, where cycloalkyl is selected from the group consisting of cyclohexyl, cyclopentyl, cyclobutyl, cyclopropyl, adamantanyl, decahydronaphthalenyl, tetrahydronaphthalenyl, octahydro-4,7-methanoindenyl and bicyclo[2.2.1]heptanyl, and in which cycloalkyl is unsubstituted or substituted independently of one another once, twice, three or four times by —(C$_1$-C$_4$)-alkyl, —C(O)—O—R11 or —(C$_1$-C$_4$)-alkylene-phenyl, where phenyl is unsubstituted or substituted by halogen, or 1,7,7-trimethylbicyclo[3.1.1]heptanyl which is unsubstituted or substituted once by —($C_1$-$C_4$)-alkyl, —C(O)—O—R11 or —($C_1$-$C_4$)-alkylene-phenyl, where phenyl is unsubstituted or substituted by halogen, 4) —($C_0$-$C_4$)-alkylene-C(R11)(R12)-($C_3$-$C_{12}$)-cycloalkyl, where cycloalkyl is selected from the group consisting of cyclohexyl, cyclopentyl, cyclobutyl, cyclopropyl, adamantanyl, decahydronaphthalenyl, tetrahydronaphthalenyl, octahydro-4,7-methanoindenyl and bicyclo[2.2.1]heptanyl, and in which cycloalkyl is unsubstituted or substituted independently of one another once, twice, three or four times by —($C_1$-$C_4$)-alkyl, —C(O)—O—R11 or —($C_1$-$C_4$)-alkylene-phenyl, where phenyl is unsubstituted or substituted by halogen, or 1,7,7-trimethylbicyclo[3.1.1]heptanyl which is unsubstituted or substituted once by —($C_1$-$C_4$)-alkyl, —C(O)—O—R11 or —($C_1$-$C_4$)-alkylene-phenyl, where phenyl is unsubstituted or substituted by halogen, 5) —($C_0$-$C_4$)-alkylene-Het, where Het is selected from the group consisting of acridinyl, azepinyl, azetidinyl, aziridinyl, benzimidazalinyl, benzimidazolyl, benzo[1,3]dioxolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiophenyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl, where Het or alkylene is unsubstituted or substituted independently of one another once or twice by —($C_1$-$C_4$)-alkyl, 6) —($C_1$-$C_6$)-alkylene-phenyl, where phenyl or alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl, 7) —($C_0$-$C_4$)-alkylene-C(R11)(R12)-phenyl, where phenyl is unsubstituted or substituted independently of one another once, twice or three times by phenyl or fluorine, 8) 1,2,3,4-tetrahydronaphthalenyl, 9) —($C_0$-$C_4$)-alkylene-CH(R11)-C(O)—NH$_2$, 10) —($C_0$-$C_4$)-alkylene-CH(R11)-C(O)—NH—($C_1$-$C_4$)-alkyl, 11) —($C_0$-$C_4$)-alkylene-CH(R11)-C(O)—NH—CH(R12)-R13, 12) —($C_1$-$C_6$)-alkylene-C(O)—O—R11, where alkylene is unsubstituted or substituted independently of one another once or twice by halogen, phenyl, —C(O)—O—R11, —($C_1$-$C_4$)-alkyl-O—R11, —O—($C_1$-$C_4$)-alkyl or —($C_1$-$C_4$)-alkyl, 13) —($C_0$-$C_4$)-alkylene-C(R11)(R12)-C(O)—O—R11, or 14) —($C_1$-$C_3$)-fluoroalkyl, or the two R6 radicals form together with the N atom to which they are bonded a mono- or bicyclic ring selected from the group consisting of pyrrolidine, piperidine, 2-aza-bicyclo[3.2.2]nonane and 7-aza-bicyclo[2.2.1]heptane, where the ring is unsubstituted or substituted once or twice by —($C_1$-$C_4$)-alkyl, —C(O)—O—R11, —($C_1$-$C_4$)-alkyl-O—R11 or phenyl, R7 is hydrogen atom or —($C_1$-$C_4$)-alkyl, R9 is hydrogen atom or —($C_1$-$C_4$)-alkyl, R11 and R12 are identical or different and are independently of one another 1) hydrogen atom, 2) —($C_1$-$C_4$)-alkyl, 3) —($C_0$-$C_4$)-alkylene-phenyl, where phenyl is unsubstituted or substituted independently of one another once, twice or three times by —OH, halogen or —O—($C_1$-$C_4$)-alkyl, 4) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, decahydronaphthalenyl, tetrahydronaphthalenyl, octahydro-4,7-methanoindenyl and bicyclo[2.2.1]heptanyl, and in which cycloalkyl is unsubstituted or substituted independently of one another once, twice, three or four times by —($C_1$-$C_4$)-alkyl, —C(O)—O—R13 or phenyl, or 1,7,7-trimethylbicyclo[3.1.1]heptanyl which is unsubstituted or substituted once by —($C_1$-$C_4$)-alkyl, —C(O)—O—R13 or phenyl, or 5) —($C_0$-$C_4$)-alkylene-indolyl, R13 is 1) hydrogen atom, 2) —($C_1$-$C_4$)-alkyl, 3) —($C_0$-$C_4$)-alkylene-C(O)—O—R14, 4) —($C_0$-$C_4$)-alkylene-C(O)—R14 or 5) —($C_0$-$C_4$)-alkylene-O—R14, and R14 is hydrogen atom, —($C_1$-$C_4$)-alkyl, —NH$_2$ or —OH and R15 is hydrogen atom, —($C_1$-$C_4$)-alkyl, —O—CF$_3$, —NH$_2$, —OH, —CF$_3$ or halogen, or a stereoisomeric form of the compound of the formula I, or mixture of stereoisomeric forms in any ratio, or a physiologically tolerated salt of the compound of the formula I.

4. A compound of the formula I as claimed in claim 2, where

R1 is 1) hydrogen atom or

2) —($C_1$-$C_4$)-alkyl,

R2 is

1) —($C_1$-$C_6$)-alkylene-NH$_2$,

2) —($C_1$-$C_4$)-alkylene-pyridyl-NH$_2$,

3) —($C_1$-$C_4$)-alkylene-piperidinyl-NH$_2$,

4) —($C_1$-$C_4$)-alkylene-NH—C(=NH)—NH$_2$,

5) —($C_1$-$C_6$)-alkylene-NH—C(=NH)—($C_1$-$C_4$)-alkyl,

6) —($C_1$-$C_4$)-alkylene-($C_3$-$C_6$)-cycloalkyl-$NH_2$,
7) —($C_1$-$C_4$)-alkylene-O—NH—C(=NH)—$NH_2$,
8) —($C_1$-$C_6$)-alkylene-NH—C(O)—O—($C_1$-$C_4$)-alkylene-phenyl,
9) —($C_1$-$C_4$)-alkylene-NH—C(O)—($C_1$-$C_4$)-alkyl,
10) —($C_1$-$C_4$)-alkylene-phenyl-$NH_2$,
11) —($C_1$-$C_4$)-alkylene-$SO_2$—($C_1$-$C_4$)-alkylene-$NH_2$ or,
12) —($C_1$-$C_4$)-alkylene-S—($C_1$-$C_4$)-alkylene-$NH_2$,
R3 is
1) —($C_1$-$C_4$)-alkyl,
2) —($C_1$-$C_4$)-alkylene-($C_3$-$C_6$)-cycloalkyl,
3) —($C_1$-$C_4$)-alkylene-phenyl, where phenyl is unsubstituted or substituted by —OH,
4) —($C_1$-$C_6$)-alkylene-NH—C(O)—O—($C_1$-$C_4$)-alkylene-phenyl,
5) hydrogen atom,
R4 is —N(R6)$_2$,
where R6 are identical or different and are independently of one another
1) hydrogen atom,
2) —($C_1$-$C_6$)-alkyl,
3) —($C_0$-$C_4$)-alkylene-($C_3$-$C_8$)-cycloalkyl, where cycloalkyl is selected from the group consisting of cyclohexyl, cyclopentyl, cyclopropyl, adamantanyl, decahydronaphthalene, octahydro-4,7-methanoindenyl and bicyclo[2.2.1]heptanyl, and in which cycloalkyl is unsubstituted or substituted independently of one another once, twice or three times by —($C_1$-$C_4$)-alkyl or phenyl, or 1,7,7-trimethylbicyclo[3.1.1]heptanyl which is unsubstituted or substituted once by —($C_1$-$C_4$)-alkyl or phenyl,
4) —C(R11)(R12)-adamantanyl,
5) —CH(R11)-C(O)—NH—CH(R12)-R13,
6) —($C_0$-$C_4$)-alkylene-Het, where Het is selected from the group consisting of benzimidazolyl, isoxazolyl, piperidine, pyridine, pyrrolidinyl, thiophenyl and benzo[1,3]dioxol,
7) 1,2,3,4-tetrahydronaphthalenyl,
8) —($C_0$-$C_4$)-alkylene-C(R11)(R12)-phenyl, where phenyl is unsubstituted or substituted independently of one another once, twice or three times by phenyl or fluorine,
9) —CH(R11)-C(O)—$NH_2$,
10) —CH(R11)-C(O)—NH—CH(R12)-$CH_2$—OH,
11) —($C_1$-$C_6$)-alkylene-phenyl, where phenyl or alkylene is unsubstituted or substituted independently of one another once or twice by chlorine, fluorine, —C(O)—O—R11, —($C_1$-$C_4$)-alkyl-O—R11, —O—($C_1$-$C_4$)-alkyl, phenyl or —($C_1$-$C_4$)-alkyl,
12) —CH(R11)-C(O)—NH—($C_1$-$C_4$)-alkyl,
13) —($C_0$-$C_4$)-alkylene-C(R11)(R12)-bicyclo[3.1.1]heptanyl, where bicyclo[3.1.1]heptanyl is unsubstituted or substituted once to four times by —($C_1$-$C_4$)-alkyl,
14) —($C_1$-$C_6$)-alkylene-C(O)—O—R11, where alkylene is unsubstituted or Substituted independently of one another once or twice by chlorine, fluorine, —C(O)—O—R11, —($C_1$-$C_4$)-alkyl-O—R11, —O—($C_1$-$C_4$)-alkyl, phenyl or —($C_1$-$C_4$)-alkyl,
15) —($C_0$-$C_4$)-alkylene-C(R11)(R12)-C(O)—O—R11, or
16) —$CH_2$—$CF_2$—$CF_3$,
or the two R6 radicals form together with the N atom to which they are bonded a mono- or bicyclic ring selected from the group consisting of pyrrolidines, 2-azabicyclo[3.2.2]nonane and 7-aza-bicyclo[2.2.1]heptane, where the ring is unsubstituted or substituted once or twice by —($C_1$-$C_4$)-alkyl, —C(O)—O—R11, —($C_1$-$C_4$)-alkyl-O—R11 or phenyl, R7 is hydrogen atom or —($C_1$-$C_4$)-alkyl,
R9 is hydrogen atom or —($C_1$-$C_4$)-alkyl,
R11 and R12 are identical or different and are independently of one another
1) hydrogen atom,
2) —($C_1$-$C_4$)-alkyl,
3) —($C_0$-$C_4$)-alkylene-phenyl, where phenyl is unsubstituted or substituted independently of one another once, twice or three times by —OH, halogen or —O—($C_1$-$C_4$)-alkyl,
4) —($C_0$-$C_4$)-alkylene-($C_3$-$C_{12}$)-cycloalkyl, where cycloalkyl is selected from the group consisting of cyclohexyl, cyclopentyl, cyclobutyl, cyclopropyl, adamantanyl, decahydronaphthalenyl, octahydro-4,7-methanoindenyl and bicyclo[2.2.1]heptanyl, and in which cycloalkyl is unsubstituted or substituted independently of one another once, twice, three or four times by —($C_1$-$C_4$)-alkyl, —C(O)—O—R13 or phenyl, or 1,7,7-trimethylbicyclo[3.1.1]heptanyl which is unsubstituted or substituted once by —($C_1$-$C_4$)-alkyl, —C(O)—O—R13 or phenyl, or
5) —($C_0$-$C_4$)-alkylene-indolyl,
R13 is
1) hydrogen atom,
2) —($C_1$-$C_4$)-alkyl,
3) —($C_0$-$C_4$)-alkylene-C(O)—O—R14,
4) —($C_0$-$C_4$)-alkylene-C(O)—R14 or
5) —($C_0$-$C_4$)-alkylene-O—R14,
R14 is hydrogen atom, —($C_1$-$C_4$)-alkyl, —$NH_2$ or —OH and
R15 is hydrogen atom, —($C_1$-$C_4$)-alkyl, —O—$CF_3$, —$NH_2$, —OH, —$CF_3$ or halogen, or
a stereoisomeric form of the compound of the formula I, or mixture of stereoisomeric forms in any ratio, or a physiologically tolerated salt of the compound of the formula I.

5. A compound which is (S)-6-amino-2-(3-{(S)-1-[(S)-1-((S)-1-methoxycarbonyl-2-methyl-propylcarbamoyl)-2-methyl-propylcarbamoyl]-2-phenyl-ethyl}-sulfamidyl)-hexanoic acid, (S)-6-amino-2-{3-[(R)-1-(bicyclo[2.2.1]hept-2-ylcarbamoyl)-2-cyclohexyl-ethyl]-sulamidyl}-hexanoic acid, (S)-6-amino-2-[3-((S)-1-cyclohexylcarbamoyl-2-phenyl-ethyl)-sulfamidyl]-hexanoic acid, (S)-6-acetimidoylamino-2-{[(S)-2-cyclohexyl-1-((1R,2S,4R)-1,7,7-trimethyl-bicyclo[2.2.1]hept-2-ylcarbamoyl)-ethylsulfamidyl]}-hexanoic acid, ethyl 3-(6-amino-pyridin-3-yl)-2-[(S)-2-cyclohexyl-1-((1R,2S,4R)-1,7,7-trimethyl-bicyclo[2.2.1]hept-2-ylcarbamoyl)-ethylsulfamidyl]-propionate, (S)-6-amino-2-{[(S)-1-((1R,2S,4R)-1,7,7-trimethyl-bicyclo[2.2.1]hept-2-ylcarbamoyl)-propylsulfamidyl]-}-hexanoic acid, (S)-2-{[(S)-2-cyclohexyl-1-((1R,2S,4R)-1,7,7-trimethyl-bicyclo[2.2.1]hept-2-ylcarbamoyl)-ethylsulfamidyl]-}-5-guanidino-pentanoic acid, (S)-6-amino-2-{[(S)-2-cyclobutyl-1-((1R,2S,4R)-1,7,7-trimethyl-bicyclo[2.2.1]hept-2-ylcarbamoyl)-ethylsulfamidyl]}-hexanoic acid, (S)-5-amino-2-({2-cyclohexyl-1-[(R)-(1,2,3,4-tetrahydro-naphthalen-2-yl)carbamoyl]-ethylsulfamidyl})-pentanoic acid, ethyl(S)-2-{[(S)-2-cyclohexyl-1-((1R,2S,4R)-1,7,7-trimethyl-bicyclo[2.2.1]hept-2-ylcarbamoyl)-ethylsulfamidyl]}-6-hexanoylaminohexanoate, (S)-6-amino-2-{[(S)-1-((1R,2S,4R)-1,7,7-trimethyl-bicyclo[2.2.1]hept-2-ylcarbamoyl)-butylsulfamidyl]}-hexanoic acid, (S)-6-amino-2-{[(S)-3-cyclohexyl-1-((1R,2S,4R)-1,7,7-trimethyl-bicyclo[2.2.1]hept-2-ylcarbamoyl)-propylsulfamidyl]-methyl}-hexanoic acid, (S)-6-amino-2-{[(S)-2-cyclohexyl-1-(decahydro-naphthalen-2-ylcarbamoyl)-ethylsulfamidyl]}-hexanoic acid, (S)-2-{[(S)-1-(adamantan-1-ylcarbamoyl)-2-cyclohexylethylsulfamidyl]}-6-amino-hexanoic acid, (S)-2-[(S)-2-cyclohexyl-1-((1R,2S,4R)-1,7,7-trimethyl-bicyclo[2.2.1]-hept-2-ylcarbamoyl)-ethylsulfamidyl]-3-pyridin-3-yl-propionic acid, (S)-2-[(S)-2-cyclohexyl-1-((1R,2S,4R)-1,7,7-trimethyl-bicyclo[2.2.1]hept-2-ylcarbamoyl)-ethylsulfamidyl]-3-pyridin-4-yl-propionic acid, (S)-6-amino-2-{[(S)-2-cyclohexyl-1-((1S,2S,3S,5R)-2,6,6-trimethyl-bicyclo[3.1.1]hept-3-ylcarbamoyl)-ethylsulfamidyl]}-hexanoic acid, (S)-6-amino-2-{[(S)-2-cyclohexyl-1-(3,3,5-trimethyl-cyclohexylcarbamoyl)-ethylsulfamidyl]}-hexanoic acid, (S)-6-amino-2-{[(S)-1-(4-tert-butyl-cyclohexylcarbamoyl)-2-cyclohexyl-ethylsulfamidyl]}-hexanoic acid, (S)-6-amino-2-{[(S)-2-cyclohexyl-1-(3-methyl-cyclohexylcarbamoyl)-ethylsulfamidyl]}-hexanoic acid, (S)-6-amino-2-{[(S)-2-cyclohexyl-1-((1R,2S,4R)-1,7,7-trimethyl-bicyclo[2.2.1]hept-2-ylcarbamoyl)-ethylsulfamidyl]}-hexanoic acid, 3-(6-amino-pyridin-3-ylmethyl)-2-[(S)-2-cyclohexyl-1-((1R,2S,4R)-1,7,7-trimethyl-bicyclo[2.2.1]hept-2-yl-carbamoyl)-ethylsulfamidyl]-propionic acid, 2-[(S)-2-cyclohexyl-1-((1R,2S,4R)-1,7,7-trimethyl-bicyclo[2.2.1]hept-2-ylcarbamoyl)-ethylsulfamidyl]-3-piperidin-4-yl-propionic acid, (S)-3-(4-amino-phenyl)-2-[(S)-2-cyclohexyl-1-((1R,2S,4R)-1,7,7-trimethyl-bicyclo[2.2.1]hept-2-ylcarbamoyl)-ethylsulfamidyl]-propionic acid, (S)-6-amino-2-[((S)-1-cyclohexylmethyl-2-oxo-2-piperidin-1-yl-ethylsulfamidyl)]-hexanoic acid, (S)-5-amino-2-{[(S)-2-cyclohexyl-1-((1R,2S,4R)-1,7,7-trimethyl-bicyclo[2.2.1]hept-2-ylcarbamoyl)-ethylsulfamidyl]}-pentanoic acid, (S)-6-amino-2-{[(S)-2-cyclohexyl-1-((S)-1-isobutylcarbamoyl-2-methyl-propylcarbamoyl)-ethylsulfamidyl]}-hexanoic acid, (S)-6-amino-2-{[(S)-1-((S)-1-isobutylcarbamoyl-2-methyl-propylcarbamoyl)-2-phenyl-ethylsulfamidyl]}-hexanoic acid, (S)-6-amino-2-[((S)-2-cyclohexyl-1-isobutylcarbamoyl-ethylsulfamidyl)]-hexanoic acid, (S)-6-amino-2-{[(S)-1-((1R,2R,4S)-bicyclo[2.2.1]hept-2-ylcarbamoyl)-2-cyclohexyl-ethylsulfamidyl]}-hexanoic acid, (S)-6-amino-2-{[(S)-2-cyclohexyl-1-((1R,2S,4R)-1,7,7-trimethyl-bicyclo[2.2.1]hept-2-ylcarbamoyl)-ethylsulfamidyl]}-hexanoic acid, (S)-6-amino-2-{[(S)-1-((1S,4R)-bicyclo[2.2.1]hept-2-ylcarbamoyl)-2-cyclohexyl-ethylsulfamidyl]}-hexanoic acid, (S)-6-amino-2-{[(S)-2-cyclohexyl-1-(octahydro-4,7-methano-inden-5-ylcarbamoyl)-ethylsulfamidyl]}-hexanoic acid, (S)-6-amino-2-[((S)-1-tert-butylcarbamoyl-2-cyclohexyl-ethylsulfamidyl)]-hexanoic acid, (S)-2-{[(S)-1-(adamantan-1-ylcarbamoyl)-2-phenyl-ethylsulfamidyl]}-6-amino-hexanoic acid, (S)-6-amino-2-{[(S)-1-((1S,4R)-bicyclo[2.2.1]hept-2-ylcarbamoyl)-2-phenyl-ethylsulfamidyl]}-hexanoic acid, (S)-2-{[(S)-1-(adamantan-1-ylcarbamoyl)-2-(4-hydroxy-phenyl)-ethylsulfamidyl]}-6-amino-hexanoic acid, (S)-6-amino-2-{[(S)-2-phenyl-1-((1R,2S,4R)-1,7,7-trimethyl-bicyclo[2.2.1]hept-2-ylcarbamoyl)-ethylsulfamidyl]}-hexanoic acid, (S)-6-amino-2-({[(S)-cyclohexyl-(1,7,7-trimethyl-bicyclo[2.2.1]hept-2-ylcarbamoyl)-methyl]-sulfamidyl})-hexanoic acid, (S)-6-amino-2-{[(S)-2-cyclohexyl-1-((1R,2R,4R)-1,7,7-trimethyl-bicyclo[2.2.1]hept-2-ylcarbamoyl)-ethylsulfamidyl]}-hexanoic acid, (S)-6-amino-2-{[(S)-2-cyclopropyl-1-((1R,2R,4R)-1,7,7-trimethyl-bicyclo[2.2.1]hept-2-ylcarbamoyl)-ethylsulfamidyl]}-hexanoic acid, (S)-6-amino-2-{[(S)-2-cyclohexyl-1-(3,5-dimethyl-adamantan-1-ylcarbamoyl)-ethylsulfamidyl]}-hexanoic acid, (S)-6-amino-2-{[(S)-2-cyclohexyl-1-(3-isopropyl-adamantan-1-ylcarbamoyl)-ethylsulfamidyl]}-hexanoic acid, tert-butyl (S)-6-amino-2-{[(S)-2-cyclohexyl-1-((1R,2R,4R)-1,7,7-trimethyl-bicyclo[2.2.1]hept-2-ylcarbamoyl)-ethylsulfamidyl]}-hexanoate or (S)-2-{[(S)-1-(adamantan-1-ylcarbamoyl)-3-methyl-butylsulfamidyl]}-6-amino-hexanoic acid or
a stereoisomeric form of the compound of the formula I, or mixture of stereoisomeric forms in any ratio, or a physiologically tolerated salt of the compound of the formula I.

6. A compound of the Formula (I),

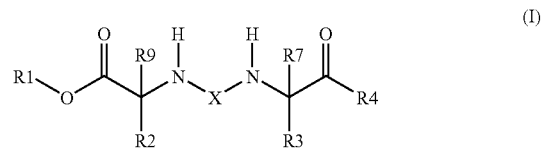

and/or a stereoisomeric form of the compound of Formula I, and/or a mixture of stereoisomeric forms in any ratio, and/or a physiologically tolerated salt of the compound of the formula I, wherein:

X is —C(O)—
R1 is
1) hydrogen atom or
2) —($C_1$-$C_4$)-alkyl,
R2 is
1) —($C_1$-$C_6$)-alkylene-$NH_2$,
2) —($C_1$-$C_4$)-alkylene-pyridyl-$NH_2$,
3) —($C_1$-$C_4$)-alkylene-piperidinyl-$NH_2$,
4) —($C_1$-$C_4$)-alkylene-NH—C(=NH)—$NH_2$,
5) —($C_1$-$C_6$)-alkylene-NH—C(=NH)—($C_1$-$C_4$)-alkyl,
6) —($C_1$-$C_4$)-alkylene-($C_3$-$C_6$)-cycloalkyl-$NH_2$,
7) —($C_1$-$C_4$)-alkylene-O—NH—C(=NH)—$NH_2$,
8) —($C_1$-$C_6$)-alkylene-NH—C(O)—O—($C_1$-$C_4$)-alkylene-phenyl,
9) —($C_1$-$C_4$)-alkylene-NH—C(O)—($C_1$-$C_4$)-alkyl,
10) —($C_1$-$C_4$)-alkylene-phenyl-$NH_2$,
11) —($C_1$-$C_2$)-alkylene-$SO_2$—($C_1$-$C_4$)-alkylene-$NH_2$ or
12) —($C_1$-$C_2$)-alkylene-S—($C_1$-$C_4$)-alkylene-$NH_2$
R3 is 1) —($C_1$-$C_4$)-alkyl,
2) —($C_1$-$C_4$)-alkylene-($C_3$-$C_6$)-cycloalkyl,
3) —($C_1$-$C_4$)-alkylene-phenyl, where phenyl is unsubstituted or substituted by —OH,
4) —($C_1$-$C_6$)-alkylene-NH—C(O)—O—($C_1$-$C_4$)-alkylene-phenyl,
5) hydrogen atom,
R4 is —N($R6$)$_2$,
where R6 are identical or different and are independently of one another
1) hydrogen atom,
2) —($C_1$-$C_6$)-alkyl,
3) —($C_0$-$C_4$)-alkylene-($C_3$-$C_8$)-cycloalkyl, where cycloalkyl is selected from the group consisting of cyclohexyl, cyclopentyl, cyclopropyl, adamantyl, 1,7,7-trimethylbicyclo[3.1.1]heptanyl, decahydronaphthalenyl, octahydro-4,7-methanoindenyl and bicyclo[2.2.1]heptanyl, and in which cycloalkyl is unsubstituted or substituted independently of one another once, twice or three times by —($C_1$-$C_4$)-alkyl or phenyl, or 1,7,7-trimethylbicyclo[3.1.1]heptanyl is unsubstituted,
4) —C(R11)(R12)-adamantyl,
5) —CH(R11)-C(O)—NH—CH(R12)-R13,
6) —($C_0$-$C_4$)-alkylene-Het, where Het is selected from the group consisting of benzimidazolyl, isoxazolyl, piperidinyl, pyridyl, pyrrolidinyl, thiophenyl and benzo[1,3]dioxolyl,
7) 1,2,3,4-tetrahydronaphthalenyl, 8) —(C$_0$-C$_4$)-alkylene-C(R11)(R12)-phenyl, where phenyl is unsubstituted or substituted independently of one another once, twice or three times by phenyl or fluorine,
9) —CH(R11)-C(O)—NH$_2$,
10) —CH(R11)-C(O)—NH—CH(R12)-CH$_2$—OH,
11) —(C$_1$-C$_6$)-alkylene-phenyl, where phenyl is unsubstituted or substituted independently of one another once or twice by chlorine, fluorine, —C(O)—O—R11, —(C$_1$-C$_4$)-alkyl-O—R11, —O—(C$_1$-C$_4$)-alkyl, phenyl or —(C$_1$-C$_4$)-alkyl, and alkylene is unsubstituted or substituted independently of one another once or twice by chlorine, fluorine, —(C$_1$-C$_4$)-alkyl-O—R11, —O—(C$_1$-C$_4$)-alkyl, phenyl or —(C$_1$-C$_4$)-alkyl,
12) —CH(R11)-C(O)—NH—(C$_1$-C$_4$)-alkyl,
13) —(C$_0$-C$_4$)-alkylene-C(R11)(R12)-bicyclo[3.1.1]heptanyl, where bicyclo[3.1.1]heptanyl is unsubstituted or substituted once to four times by —(C$_1$-C$_4$)-alkyl,
14) —CH$_2$—CF$_2$—CF$_3$,
or the two R6 radicals form together with the N atom to which they are bonded a mono- or bicyclic ring selected from the group consisting of pyrrolidines, 2-azabicyclo[3.2.2]nonane and 7-aza-bicyclo[2.2.1]heptane, where the ring is unsubstituted or substituted once or twice by —(C$_1$-C$_4$)-alkyl, —C(O)—O—R11, —(C$_1$-C$_4$)-alkyl-O—R11 or phenyl,
R7 is hydrogen atom or —(C$_1$-C$_4$)-alkyl,
R9 is hydrogen atom or —(C$_1$-C$_4$)-alkyl,
R11 and R12 are identical or different and are independently of one another
1) hydrogen atom,
2) —(C$_1$-C$_4$)-alkyl,
3) —(C$_0$-C$_4$)-alkylene-phenyl, where phenyl is unsubstituted or substituted independently of one another once, twice or three times by —OH, halogen or —O—(C$_1$-C$_4$)-alkyl,
4) —(C$_0$-C$_4$)-alkylene-(C$_3$-C$_{12}$)-cycloalkyl, where cycloalkyl is selected from the group consisting of cyclohexyl, cyclopentyl, cyclobutyl, cyclopropyl, adamantanyl, decahydronaphthalenyl, octahydro-4,7-methanoindenyl and bicyclo[2.2.1]heptanyl, and in which cycloalkyl is unsubstituted or substituted independently of one another once, twice, three or four times by —(C$_1$-C$_4$)-alkyl, —C(O)—O—R13 or phenyl, or 1,7,7-trimethylbicyclo[3.1.1]heptanyl is unsubstituted or substituted once by -(—(C$_1$-C$_4$)-alkyl, —C(O)—O—R13 or phenyl, or
5) —(C$_0$-C$_4$)-alkylene-indolyl,
R13 is
1) hydrogen atom,
2) —(C$_1$-C$_4$)-alkyl,
3) —(C$_0$-C$_4$)-alkylene-C(O)—O—R14,
4) —(C$_0$-C$_4$)-alkylene-C(O)—R14 or
5) —(C$_0$-C$_4$)-alkylene-O—R14,
R14 is hydrogen atom, —(C$_1$-C$_4$)-alkyl, —NH$_2$ or —OH and
R15 is hydrogen atom, —(C$_1$-C$_4$)-alkyl, —O—CF$_3$, —NH$_2$, —OH, —CF$_3$ or halogen, or
a stereoisomeric form of the compound of the formula I, or mixture of stereoisomeric forms in any ratio, or a physiologically tolerated salt of the compound of the formula I.

7. A compound of claim 6 selected from:
(S)-6-amino-2-{3-[(R)-1-(3-methyl-butylcarbamoyl)-2-phenyl-ethyl]-ureido}-hexanoic acid hydrochloride, (S)-6-amino-2-{3-[(R)-5-benzyloxycarbonylamino-1-(3-methyl-butylcarbamoyl)-pentyl]-ureido}-hexanoic acid, (S)-6-amino-2-{3-[(R)-1-(3-methyl-butylcarbamoyl)-ethyl]-ureido}-hexanoic acid, (S)-6-amino-2-{3-[(R)-3-methyl- 1-(3-methyl-butylcarbamoyl)-butyl]-ureido}-hexanoic acid, (S)-6-amino-2-{3-[(R)-1-(3-methyl-butylcarbamoyl)-butyl]-ureido}-hexanoic acid, (S)-6-amino-2-{3-[(R)-1-(3-methyl-butylcarbamoyl)-pentyl]-ureidol-hexanoic acid, (S)-6-amino-2-{3-[(R)-1-(3-methyl-butylcarbamoyl)-2-phenyl-ethyl]-ureido}-hexanoic acid, (S)-6-amino-2-[3-((R)-1-isobutylcarbamoyl-2-phenyl-ethyl)-ureido]-hexanoic acid, (S)-6-amino-2-{3-[(R)-5-benzyloxy-carbonylamino-1-((S)-1-ethylcarbamoyl-2-methyl-propylcarbamoyl)-pentyl]-ureido}-hexanoic acid, (S)-6-amino-2-{3-[(R)-2-cyclohexyl-1-((S)-1-ethylcarbamoyl-2-methyl-propylcarb-amoyl)-ethyl]-ureido}-hexanoic acid, (S)-6-amino-2-{3-[(R)-2-cyclohexyl-1-(2,4-difluoro-benzylcarbamoyl)-ethyl]-ureido}-hexanoic acid, (S)-6-amino-2-{3-[(R)-2-cyclohexyl-1-(2-phenyl-propylcarbamoyl)-ethyl]-ureido}-hexanoic acid, (S)-6-amino-2-{3-[(R)-2-cyclohexyl-1-(2-o-tolyl-ethylcarbamoyl)-ethyl]-ureido}-hexanoic acid, (S)-6-amino-2-{3-[(R)-1-(4-chloro-benzylcarbamoyl)-2-cyclohexyl-ethyl]-ureido}-hexanoic acid, (S)-6-amino-2-{3-[(R)-2-cyclohexyl-1-((R)-1-phenyl-ethylcarbamoyl)-ethyl]-ureido}-hexanoic acid, (S)-6-amino-2-{3-[(R)-1-(bicyclo[2.2.1]hept-2-ylcarbamoyl)-2-cyclohexyl-ethyl]-ureido}-hexanoic acid, (S)-6-amino-2-{3-[(R)-2-cyclohexyl-1-(3-phenyl-propylcarbamoyl)-ethyl]-ureido}-hexanoic acid, (S)-6-amino-2-{3-[(R)-2-cyclohexyl-1-(2-methyl-cyclohexylcarbamoyl)-ethyl]-ureido}-hexanoic acid, (S)-6-amino-2-(3-{(R)-1-[(S)-1-(4-chloro-phenyl)-ethylcarbamoyl]-2-cyclohexyl-ethyl}-ureido)-hexanoic acid, (S)-6-amino-2-{3-[(R)-2-cyclohexyl-1-(4-methoxy-benzylcarbamoyl)-ethyl]-ureido}-hexanoic acid, (S)-6-amino-2-(3-{(R)-2-cyclohexyl-1-[(3-methyl-isoxazol-5-ylmethyl)-carbamoyl]-ethyl}-ureido)-hexanoic acid, (S)-6-amino-2-{3-[(R)-2-cyclohexyl-1-((R)-1-phenyl-ethylcarbamoyl)-ethyl]-ureido}-hexanoic acid, (S)-6-amino-2-{3-[2-(7-aza-bicyclo[2.2.1]hept-7-yl)-1-cyclohexylmethyl-2-oxo-ethyl]-ureido}-hexanoic acid, (S)-6-amino-2-{3-[(R)-2-cyclohexyl-1-(2,3 -dimethyl-benzylcarbamoyl)-ethyl]-ureido}-hexanoic acid, (S)-6-amino-2-{3-[(R)-2-cyclohexyl-1-(1,2-dimethyl-butylcarbamoyl)-ethyl]-ureido}-hexanoic acid, (S)-6-amino-2-{3-[(R)-2-cyclohexyl-1-(2,2-diphenyl-ethylcarbamoyl)-ethyl]-ureido}-hexanoic acid, (S)-6-amino-2-{3-[(R)-2-cyclohexyl-1-(2,2-dimethyl-propylcarbamoyl)-ethyl]-ureido}-hexanoic acid, (S)-6-amino-2-{3-[(R)-1-(2-benzo[1,3]dioxol-5 -yl-ethylcarb-amoyl)-2-cyclohexyl-ethyl]-ureido}-hexanoic acid, (S)-6-amino-2-{3-[(R)-2-cyclohexyl-1-(4-methyl-cyclohexylcarbamoyl)-ethyl]-ureido}-hexanoic acid, ethyl (1R,2S)-2-{(R)-2-[3-((S)-5-amino-1-carboxy-pentyl)-ureido]-6-benzyloxycarbonylamino-hexanoylamino}-cyclohexane-carboxylate, (S)-6-amino-2-{3-[(R)-5-benzyloxycarbonylamino-1-(2-phenyl-propylcarbamoyl)-pentyl]-ureido}-hexanoic acid, (S)-6-amino-2-(3-{(R)-5-benzyloxycarbonylamino-1-[(biphenyl-2-ylmethyl)-carbamoyl]-pentyl}-ureido)-hexanoic acid, (S)-6-amino-2-{3-[(R)-5-benzyloxycarbonyl-amino-1-((1S,2S)-1-methoxycarbonyl-2-methyl-butylcarbamoyl)-pentyl]-ureido}-hexanoic acid, (S)-2-(3-{(R)-1-[(S)-1-((S)-1-benzyl-2-hydroxy-ethylcarbamoyl)-2-methyl-propylcarbamoyl]-2-cyclohexyl-ethyl}-ureido)-5-benzyloxycarbonylamino-pentanoic acid, (S)-6-amino- 2-{3-[(R)-2-cyclohexyl-1-(3-methyl-cyclohexylcarbamoyl)-ethyl]-ureido}-hexanoic acid, (S)-6-amino-2-{3-[(R)-5-benzyloxycarbonylamino-1-(2-methyl-cyclohexylcarbamoyl)-pentyl]-ureido}-hexanoic acid, (S)-6-amino-2-{3-[(R)-5-benzyloxycarbonylamino-1-((1S,4R)-bicyclo[2.2.1]hept-2-ylcarbamoyl)-pentyl]-ureido}-hexanoic acid, (S)-6-amino-2-(3-{(R)-5-benzyloxycarbonyl-amino-1-[(S)-1-(4-chloro-phenyl)-ethylcarbamoyl]-pentyl}-ureido)-hexanoic acid, (S)-6-amino-2-(3-(R)-5-benzyloxycarbonylamino-1-[(3-methyl-isoxazol-5-ylmethyl)-carbamoyl]-pentyl}-ureido)-hexanoic acid, (S)-6-amino-2-{3-[(R)-5-benzyloxycarbonylamino-1-((R)-1-phenyl-ethylcarbamoyl)-pentyl]-ureido}-hexanoic acid, (S)-6-amino-2-{3-[(R)-5-benzyloxycarbonylamino-1-(3-phenyl-propylcarbamoyl)-pentyl]-ureido}-hexanoic acid, (S)-6-amino-2-(3-{(R)-2-cyclohexyl-1-[(thiophen-2-ylmethyl)-carbamoyl]-ethyl}-ureido)-hexanoic acid, (S)-6-amino-2-[3-((R)-2-cyclohexyl-1-cyclopropylcarbamoyl-ethyl)-ureido]-hexanoic acid, (S)-6-amino-2-{3-[(R)-2-cyclohexyl-1-((R)-1,2-dimethyl-propylcarbamoyl)-ethyl]-ureido}-hexanoic acid, (S)-6-amino-2-{3-[(R)-2-cyclohexyl-1-(1-ethyl-propylcarbamoyl)-ethyl]-ureido}-hexanoic acid, (S)-6-amino-2-{3-[(R)-1-cyclohexylmethyl-2-(2-methyl-pyrrolidin-1-yl)-2-oxo-ethyl]-ureido}-hexanoic acid, (S)-6-amino-2-{3-[(R)-2-cyclohexyl-1-((S)-1-cyclohexyl-ethylcarbamoyl)-ethyl]-ureido}-hexanoic acid, (S)-6-amino-2-{3-[(R)-5-benzyloxycarbonylamino-1-(4-chloro-benzylcarbamoyl)-pentyl]-ureido}-hexanoic acid, (S)-6-amino-2-(3-{(R)-2-cyclohexyl-1-[(thiophen-3-ylmethyl)-carbamoyl]-ethyl}-ureido)-hexanoic acid, (S)-6-amino-2-(3-{(R)-2-cyclohexyl-1-[(R)-1-(4-fluoro-phenyl)-ethylcarbamoyl]-ethyl}-ureido)-hexanoic acid, (S)-6-amino-2-{3-[(R)-2-cyclohexyl-1-(1,2,3,4-tetrahydro-naphthalen-1-ylcarbamoyl)-ethyl]-ureido}-hexanoic acid, (S)-6-amino-2-[3-((R)-2-cyclohexyl-1-propylcarbamoyl-ethyl)-ureido]-hexanoic acid, (S)-6-amino-2-{3-(R)-1-[(biphenyl-2-ylmethyl)-carbamoyl]-2-cyclohexyl-ethyl}-ureido)-hexanoic acid, (S)-6-amino-2-{3-[(R)-2-cyclohexyl-1-((R)-2-phenyl-cyclopropylcarbamoyl)-ethyl]-ureido}-hexanoic acid, (S)-6-amino-2-(3-{(R)-2-cyclohexyl-1-[(pyridin-3-ylmethyl)-carbamoyl]-ethyl}-ureido)-hexanoic acid, (S)-6-amino-2-(3-{(R)-2-cyclohexyl-1-[(pyridin-2-ylmethyl)-carbamoyl]-ethyl}-ureido)-hexanoic acid, (S)-6-amino-2-{3-[(R)-2-cyclohexyl-1-(1-methyl-piperidin-4-ylcarbamoyl)-ethyl]-ureido}-hexanoic acid, (S)-6-amino-2-{3-[(R)-2-cyclohexyl-1-(3,3,3-trifluoro-propylcarbamoyl)-ethyl]-ureido}-hexanoic acid, (S)-6-amino-2-{3-[(R)-2-cyclohexyl-1-(2-methyl-butylcarbamoyl)-ethyl]-ureido}-hexanoic acid, (S)-6-amino-2-{3-[(R)-2-cyclohexyl-1-(cyclopropylmethyl-carbamoyl)-ethyl]-ureido}-hexanoic acid, (S)-6-amino-2-{3-[(R)-2-cyclohexyl-1-(3,5-difluoro-benzylcarbamoyl)-ethyl]-ureido}-hexanoic acid, (S)-6-amino-2-{3-[(R)-2-cyclohexyl-1-(2,3-dimethyl-cyclohexylcarbamoyl)-ethyl]-ureido}-hexanoic acid, (S)-6-amino-2-{3-[(R)-2-cyclohexyl-1-(1,2,3,4-tetrahydro-naphthalen-2-ylcarbamoyl)-ethyl]-ureido}-hexanoic acid, (S)-2-{3-[(R)-1-(adamantan-2-ylcarbamoyl)-2-cyclohexyl-ethyl]-ureido}-6-amino-hexanoic acid, (S)-6-amino-2-{3-[(R)-2-cyclohexyl-1-(1,3-dimethyl-butylcarbamoyl)-ethyl]-ureido}-hexanoic acid, (S)-6-amino-2-[3-((R)-2-cyclohexyl-1-isobutylcarbamoyl-ethyl)-ureido]-hexanoic acid, (S)-6-amino-2-{3-[(R)-2-cyclohexyl-1-((S)-1,7,7-trimethyl-bicyclo[2.2.1]hept-2-ylcarbamoyl)-ethyl]-ureido}-hexanoic acid, (S)-2-(3-{(R)-1-[(adamantan-1-ylmethyl)-carbamoyl]-2-cyclohexyl-ethyl}-ureido)-6-amino-hexanoic acid, (S)-2-{3-[(R)-1-(adamantan-1-ylcarbamoyl)-2-cyclohexyl-ethyl]-ureido}-6-amino-hexanoic acid, (S)-6-amino-2-[3-((R)-2-cyclohexyl-1-cyclohexylcarbamoyl-ethyl)-ureido]-hexanoic acid, (S)-6-amino-2-(3-{(R)-2-cyclohexyl-1-[(pyridin-4-ylmethyl)-carbamoyl]-ethyl}-ureido)-hexanoic acid, (S)-6-amino-2-(3-{(R)-2-cyclohexyl-1-[((1S,2S)-2,6,6-trimethyl-bicyclo[3.1.1]hept-3-ylmethyl)-carbamoyl]-ethyl}-ureido)-hexanoic acid, (S)-6-amino-2-(3-{(R)-2-cyclohexyl-1-[(S)-(1,2,3,4-tetrahydro-naphthalen-2-yl)carbamoyl]-ethyl}-ureido)-hexanoic acid, S)-6-amino-2-{3-[(R)-1-(4-tert-butyl-cyclohexylcarbamoyl)-2-cyclohexyl-ethyl]-ureido}-hexanoic acid, (S)-6-amino-2-[3-((R)-1-cyclohexylmethyl-2-oxo-2-pyrrolidin-1-yl-ethyl)-ureido]-hexanoic acid, 3-(6-amino-pyridin-3-yl)-2-{3-[(R)-1-(bicyclo[2.2.1]hept-2-ylcarbamoyl)-2-cyclohexyl-ethyl]-ureido}-propanoic acid, (S)-6-amino-2-(3-{(R)-2-cyclohexyl-1-[(1-methyl-1H-benzoimidazol-2-ylmethyl)-carbamoyl]-ethyl}-ureido)-hexanoic acid, 3-(3-amino-cyclobutyl)-2-{3-[(R)-1-(bicyclo[2.2.1]hept-2-ylcarbamoyl)-2-cyclohexyl-ethyl]-ureido}-propanoic acid, (S)-6-amino-2-{3-[(R)-1-((1S,2R)-1-carbamoyl-2-methyl-butylcarbamoyl)-2-cyclohexyl-ethyl]-ureido}-hexanoic acid, (S)-6-amino-2-{3-[(R)-5-benzyloxycarbonylamino-1-((1S,2R)-1-carbamoyl-2-methyl-butylcarbamoyl)-pentyl]-ureido}-hexanoic acid, (S)-6-amino-2-(3-{(R)-1-[1-((S)-1-benzyl-2-hydroxy-ethylcarbamoyl)-2-methyl-propylcarbamoyl]-2-cyclohexyl-ethyl}-ureido)-hexanoic acid, (S)-6-amino-2-(3-{(R)-1-[(S)-1-((S)-1-carbamoyl-2-methyl-propylcarbamoyl)-2-methyl-propylcarbamoyl]-2-cyclohexyl-ethyl}-ureido)-hexanoic acid, (S)-2-{3-[(R)-5-benzyloxycarbonylamino-1-((1S,2R)-1-carbamoyl-2-methyl-butylcarbamoyl)-pentyl]-ureido}-5-guanidino-pentanoic acid, (S)-2-(3-{(R)-5-benzyloxycarbonylamino-1-[1-(1-carbamoyl-2-methyl-propylcarbamoyl)-2-methyl-propylcarbamoyl]-pentyl}-ureido)-5-guanidino-pentanoic acid, (S)-6-amino-2-(3-{(R)-5-benzyloxycarbonylamino-1-[(S)-1-((S)-1-carbamoyl-2-methyl-propylcarbamoyl)-2-methyl-propylcarbamoyl]-pentyl}-ureido)-hexanoic acid, S)-6-amino-2-{3-[(R)-5-benzyloxy-carbonylamino-1-((R)-1-carbamoyl-2-methyl-butylcarbamoyl)-pentyl]-ureido}-hexanoic acid, 2-{(S)-3-[(R)-2-cyclohexyl-1-((1R,2S,4R)-1,7,7-trimethyl-bicyclo[2.2.1]hept-2-ylcarbamoyl)-ethyl]-ureido}-5-guanidino-pentanoic acid, (S)-6-amino-2-{3-[(R)-2-cyclohexyl-1-(decahydro-naphthalen-2-ylcarbamoyl)-ethyl]-ureido}-hexanoic acid, (S)-3-(6-amino-pyridin-3-yl)-2-{3-[(R)-2-cyclohexyl-1-((1R,2S,4R)-1,7,7-trimethyl-bicyclo[2.2.1]hept-2-ylcarbamoyl)-ethyl]-ureido}-propionic acid, (R)-3-(6-amino-pyridin-3-yl)-2-{3-[(R)-2-cyclohexyl-1-((1R,2S,4R)-1,7,7-trimethyl-bicyclo[2.2.1]hept-2-ylcarbamoyl)-ethyl]-ureido}-propionic acid, (S)-5-amino-2-(3-{2-cyclohexyl-1-[((1R,2S,4R)-1,7,7-trimethyl-bicyclo[2.2.1]hept-2-ylcarbamoyl)-methyl]-ethyl}-ureido)-pentanoic acid, 6-amino-2-{3-[(R)-2-phenyl-1-((1R,2S,4R)-1,7,7-trimethyl-bicyclo[2.2.1]hept-2-ylcarbamoyl)-ethyl]-ureido}-hexanoic acid, 6-amino-2-{3-[2-methyl-1-((R)-(1R,2S,4R)-1,7,7-trimethylbicyclo[2.2.1]hept-2-ylcarbamoyl)-propyl]-ureido}-hexanoic acid, 6-amino-2-{3-[(R)-cyclohexyl-((1R,2S,4R)-1,7,7-trimethyl-bicyclo[2.2.1]hept-2-ylcarbamoyl)-methyl]-ureido}-hexanoic acid, 6-amino-2-{3-[3-methyl-1-((R)-(1R,2S,4R)-1,7,7-trimethyl-bicyclo[2.2.1]hept-2-ylcarbamoyl)-butyl]-ureido}-hexanoic acid, 3-(3-amino-cyclobutyl)-2-{3-[(R)-1-(bicyclo[2.2.1]-hept-2-ylcarbamoyl)-2-cyclohexyl-ethyl]-ureido }-propionic acid trifluoroacetate, 6-amino-2-{3-[((1R,2S,4R)-1,7,7-trimethyl-bicyclo[2.2.1]hept-2-ylcarbamoyl)-methyl]-ureido}-hexanoic acid, 6-amino-2-{3-[1-methyl-1-((1R,2S,4R)-1,7,7-trimethyl-bicyclo[2.2.1]hept-2-ylcarbamoyl)-ethyl]-ureido}-hexanoic acid, 6-amino-2-{3-[1-((R)-(1R,2S,4R)-1,7,7-trimethyl-bicyclo[2.2.1]-hept-2-ylcarbamoyl)-butyl]-ureido}-hexanoic acid, (S)-6-amino-2-{3-[(S)-2-cyclohexyl-1-(3-methyl-cyclohexylcarbamoyl)-ethyl]-ureido}-hexanoic acid, (S)-6-amino-2-{3-[(S)-1-(4-tert-butyl-cyclohexylcarbamoyl)-2-cyclohexyl-ethyl]-ureido}-hexanoic acid, (S)-6-amino-2-{3-[(S)-2-cyclohexyl-1-(3,3,5-trimethyl-cyclohexylcarbamoyl)-ethyl]-ureido}-hexanoic acid, (S)-4-guanidino-oxy-2-{3-[(R)-2-cyclohexyl-1-((1R,2S)-1,7,7-trimethyl-bicyclo[2.2.1 ]hept-2-ylcarbamoyl)-ethyl]-ureido}-butanoic acid, 6-amino-2-{3-[(R)-2-cyclopropyl-1-((1R,2S,4R)-1,7,7-trimethyl-bicyclo[2.2.1]hept-2-ylcarbamoyl)-ethyl]-ureido}-hexanoic acid, 6-amino-2-{3-[(R)-2-cyclobutyl-1-((1R,2S,4R)-1,7,7-trimethyl-bicyclo[2.2.1]hept-2-ylcarbamoyl)-ethyl]-ureido}-hexanoic acid, 3-(6-amino-pyridin-3-yl)-2-{3-[(R)-2-cyclohexyl-1-((1R,2S,4R)-1,7,7-trimethyl-bicyclo[2.2.1]hept-2-ylcarbamoyl)-ethyl]-ureido}-propionic acid, 6-amino-2-{3-[2-cyclopentyl-1-((1R,2S,4R)-1,7,7-trimethyl-bicyclo[2.2.1]hept-2-ylcarbamoyl)-ethyl]-ureido}-hexanoic acid, (S)-6-amino-2-(3-{(R)-5-benzyloxycarbonylamino-1-[(S)-2-methyl-1-(3-phenyl-propylcarbamoyl)-propylcarbamoyl]-pentyl}-ureido)-hexanoic acid, (S)-6-amino-2-(3-{(R)-5-benzyloxycarbonylamino-1-[(S)-1-((1R,2R,4S)-bicyclo[2.2.1]hept-2-ylcarbamoyl)-2-methyl-propylcarbamoyl]-pentyl}-ureido)-hexanoic acid, (S)-6-amino-2-(3-{(R)-5-benzyloxycarbonyl-amino-1-[(S)-1-((1S,4R)-bicyclo[2.2.1]hept-2-ylcarbamoyl)-2-methyl-propylcarbamoyl]-pentyl}-ureido)-hexanoic acid, (S)-6 -amino-2-{3-[(R)-5-benzyloxycarbonylamino-1-((S)-1-cyclopropylcarbamoyl-2-methyl-propylcarbamoyl)-pentyl]-ureido}-hexanoic acid, (S)-6-amino-2-[3-((R)-5-benzyloxycarbonylamino-1-{(S)-1-[(S)-1-(4-chloro-phenyl)-ethylcarbamoyl]-2-methyl-propylcarbamoyl}-pentyl)-ureido]-hexanoic acid, (S)-6-amino-2-(3-{(R)-5-benzyloxycarbonylamino-1-[(S)-2-methyl-1-(3-methyl-cyclohexylcarbamoyl)-propylcarbamoyl]-pentyl}-ureido)-hexanoic acid, (S)-6-amino-2-(3-{(R)-5-benzyloxycarbonylamino-1-[(S)-1-(2,2-dimethyl-propylcarbamoyl)-2-methyl-propylcarbamoyl]-pentyl}-ureido)-hexanoic acid, (S)-6-amino-2-(3-(R)-5-benzyloxycarbonylamino-1-[(S)-2-methyl-1-{(R)-1-phenyl-ethylcarbamoyl)-propylcarbamoyl]-pentyl}-ureido)-hexanoic acid, (S)-5-amino-2-{3-[(R)-2-cyclohexyl-1-(3-methyl-butylcarbamoyl)-ethyl]-ureido}-pentanoic acid hydrochloride, (S)-5-amino-2-{3-[(R)-2-cyclohexyl-1-((1R,2S,4R)-1,7,7-trimethyl-bicyclo[2.2.1]hept-2-ylcarbamoye-ethyl]-ureido }-pentanoic acid, (S)-6-amino-2-(3-{(R)-5-benzyloxycarbonylamino-1-[(S)-1-((S)-1-cyclohexyl-ethylcarbamoyl)-2-methyl-propylcarbamoyl]-pentyl}-ureido)-hexanoic acid, (S)-6-amino-2-(3-{(R)-5-benzyloxycarbonylamino-1-[(S)-2-methyl-1-(1,2,2-trimethyl-propylcarbamoyl)-propylcarbamoyl]-pentyl}-ureido)-hexanoic acid, (S)-6-amino-2-(3-{(R)-5-benzyloxycarbonylamino-1-[(S)-2-methyl-1-((1R,2S)-2-phenyl-cyclopropylcarbamoyl-propylcarbamoyl]-pentyl}-ureido)-hexanoic acid, (S)-6-amino-2-(3-{(R)-5-benzyloxycarbonylamino-1-[(S)-2-methyl-1-(2-methyl-cyclohexylcarbamoyl)-propylcarbamoyl]-pentyl}-ureido)-hexanoic acid, (S)-6-amino-2-(3-{(R)-5-benzyloxycarbonylamino-1-[(S)-1-(4-chloro-benzylcarbamoyl)-2-methyl-propylcarbamoyl]-pentyl}-ureido)-hexanoid acid, (S)-6-amino-2-{3-[(R)-5 -benzyloxycarbonylamino-1-((S)-1-carbamoyl-2-methyl-propylcarbamoyl)-pentyl]-ureido}-hexanoic acid, (R)-3-(2-amino-ethanesulfonyl)-2-{3-[(R)-2-cyclohexyl-1-((1R,2S,4R)-1,7,7-trimethyl-bicyclo[2.2.1]hept-2-ylcarbamoyl)-ethyl]-ureido}propionic acid or (R)-3-(2-amino-ethylsulfanyl)-2-{3-[(R)-2-cyclohexyl-1-((1R,2S,4R)-1,7,7-trimethyl-bicyclo[2.2.1]hept-2-ylcarbamoyl)-ethyl]-ureido}propionic acid, or a stereoisomeric form of the compound of the formula I, or mixture of stereoisomeric forms in any ratio, or a physiologically tolerated salt of the compound of the formula I.

* * * * *